United States Patent
Kubota et al.

(10) Patent No.: US 12,225,812 B2
(45) Date of Patent: Feb. 11, 2025

(54) ORGANIC COMPOUND, LIGHT-EMITTING DEVICE, LIGHT-EMITTING APPARATUS, ELECTRONIC DEVICE, AND LIGHTING DEVICE

(71) Applicant: SEMICONDUCTOR ENERGY LABORATORY CO., LTD., Atsugi (JP)

(72) Inventors: Tomohiro Kubota, Kanagawa (JP); Takao Tosu, Kanagawa (JP); Takeyoshi Watabe, Kanagawa (JP); Airi Ueda, Kanagawa (JP); Yuta Kawano, Kanagawa (JP); Nobuharu Ohsawa, Kanagawa (JP); Satoshi Seo, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 0 days.

(21) Appl. No.: 17/696,019

(22) Filed: Mar. 16, 2022

(65) Prior Publication Data
US 2022/0328763 A1  Oct. 13, 2022

(30) Foreign Application Priority Data
Mar. 31, 2021 (JP) .................................. 2021-060448

(51) Int. Cl.
| | | |
|---|---|---|
| *H01L 51/00* | (2006.01) | |
| *C07C 211/61* | (2006.01) | |
| *C09K 11/06* | (2006.01) | |
| *H10K 85/60* | (2023.01) | |
| *H10K 50/15* | (2023.01) | |
| *H10K 50/17* | (2023.01) | |
| *H10K 59/12* | (2023.01) | |
| *H10K 101/30* | (2023.01) | |

(52) U.S. Cl.
CPC .......... *H10K 85/633* (2023.02); *C07C 211/61* (2013.01); *C09K 11/06* (2013.01); *C07C 2603/18* (2017.05); *C09K 2211/1007* (2013.01); *C09K 2211/1011* (2013.01); *C09K 2211/1014* (2013.01); *H10K 50/15* (2023.02); *H10K 50/17* (2023.02); *H10K 59/12* (2023.02); *H10K 85/626* (2023.02); *H10K 2101/30* (2023.02)

(58) Field of Classification Search
CPC ........ C07C 2603/18; C09K 2211/1011; C09K 2211/1014; C09K 11/06; H10K 85/633; H10K 50/17
See application file for complete search history.

(56) References Cited

U.S. PATENT DOCUMENTS

| | | |
|---|---|---|
| 8,642,190 B2 | 2/2014 | Ogita et al. |
| 9,051,239 B2 | 6/2015 | Osaka et al. |
| 9,496,503 B2 | 11/2016 | Takeda et al. |

(Continued)

FOREIGN PATENT DOCUMENTS

| | | | |
|---|---|---|---|
| CN | 109485577 A | | 3/2019 |
| CN | 112778139 A | * | 5/2021 |

(Continued)

OTHER PUBLICATIONS

J. Reis et al., 11 ChemPhysChem, 3722-3733 (2010) (Year: 2010).*

(Continued)

*Primary Examiner* — Alexander R Pagano
(74) *Attorney, Agent, or Firm* — Fish & Richardson P.C.

(57) ABSTRACT

An organic compound having a hole-transport property and a low refractive index is provided. An organic compound represented by General Formula (G1) shown below is provided. In General Formula (G1), $Ar^1$ represents a substituted or unsubstituted arylene group having 6 to 13 carbon atoms in a ring, n represents an integer of 0 or 1, and $Ar^2$ represents an aryl group having 6 to 10 carbon atoms in a ring and includes at least one branched-chain or cyclic alkyl group having 3 to 12 carbon atoms. The total number of carbon atoms of the branched-chain or cyclic alkyl group in $Ar^2$ is more than or equal to 6. $R^1$ to $R^4$ each independently represent an alkyl group having 1 to 6 carbon atoms. $R^{11}$ to $R^{14}$ and $R^{21}$ to $R^{24}$ each independently represent a hydrogen atom or an alkyl group having 1 to 4 carbon atoms. Any one of $R^{15}$ to $R^{18}$ and any one of $R^{25}$ to $R^{28}$ each represent a bond directly bonded to a nitrogen atom, and the others each independently represent a hydrogen atom or an alkyl group having 1 to 4 carbon atoms.

(G1)

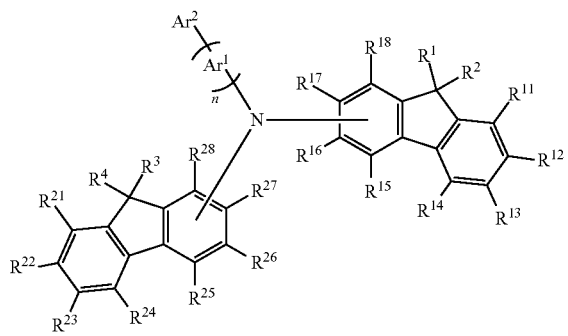

17 Claims, 33 Drawing Sheets

(56) References Cited

U.S. PATENT DOCUMENTS

| | | |
|---|---|---|
| 9,634,263 B2 | 4/2017 | Ogita et al. |
| 10,553,796 B2 | 2/2020 | Ha |
| 10,553,797 B2 | 2/2020 | Osaka et al. |
| 10,950,805 B2 | 3/2021 | Watabe et al. |
| 2009/0153039 A1* | 6/2009 | Kim ................. C09K 11/06 556/424 |
| 2015/0228899 A1 | 8/2015 | Kato et al. |
| 2019/0016666 A1* | 1/2019 | Jeong ................. H01L 51/0073 |
| 2020/0335698 A1 | 10/2020 | Park et al. |
| 2021/0005814 A1 | 1/2021 | Watabe et al. |
| 2021/0202843 A1* | 7/2021 | Qian ................. H01L 51/0061 |
| 2021/0257562 A1 | 8/2021 | Watabe et al. |
| 2021/0317069 A1 | 10/2021 | Seo et al. |
| 2022/0278292 A1* | 9/2022 | Watabe ............. H10K 50/156 |

FOREIGN PATENT DOCUMENTS

| | | | | |
|---|---|---|---|---|
| EP | 2067766 A1 | * | 6/2009 | ......... C07C 211/61 |
| JP | 3838766 B2 | * | 10/2006 | |
| KR | 2015121626 A | * | 10/2015 | ......... C07D 209/56 |
| KR | 2016066308 A | * | 6/2016 | |
| KR | 2017137603 A | * | 12/2017 | ....... G02F 1/133305 |
| WO | WO-2014/034791 | | 3/2014 | |

OTHER PUBLICATIONS

N. An et al., 8 The Journal of Physical Chemistry, 10701-10709 (2015) (Year: 2015).*

CAS Abstract, M. Nakatsuka et al., JP 3838766 (2006) (Year: 2006).*

CAS/CAPLUS Abstract and Indexed Compounds, B. Kim et al., EP 2067766 (2009) (Year: 2009).*

International Union of Pure and Applied Chemistry, Compendium of Chemical Terminology (IUPAC), Gold Book, p. 60 (2014) (Year: 2014).*

Lee.J et al., "Synergetic electrode architecture for efficient graphene-based flexible organic light-emitting diodes", Nature Communications, Jun. 2, 2016, vol. 7, pp. 11791-1-11791-9.

* cited by examiner

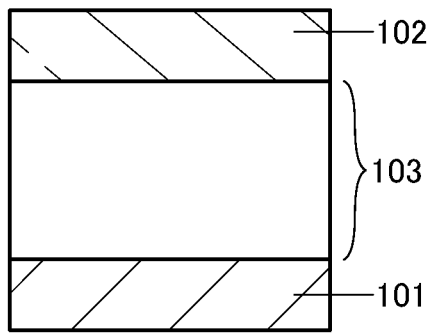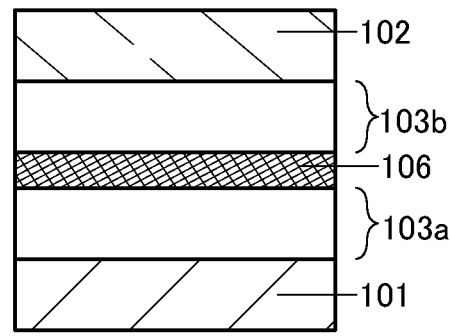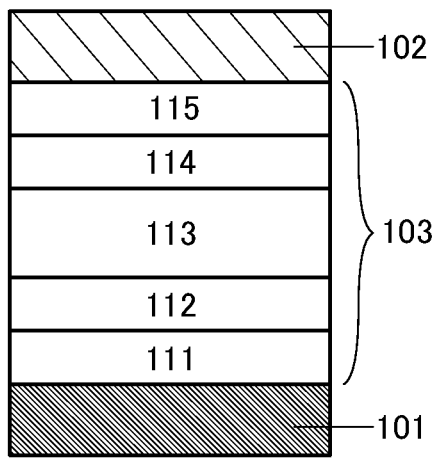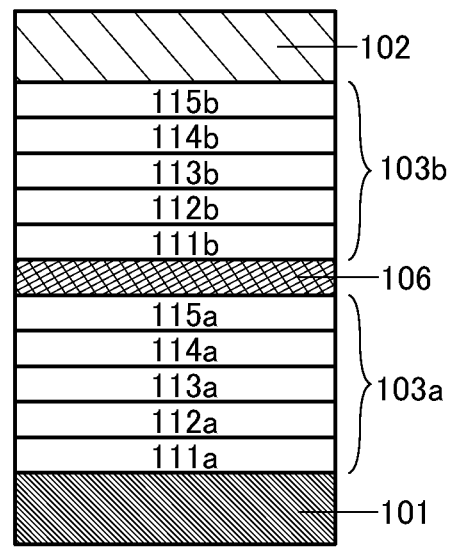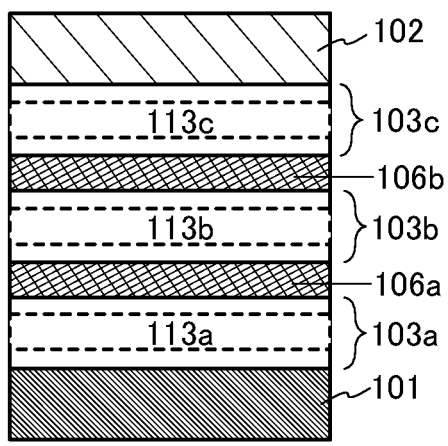

ORGANIC COMPOUND, LIGHT-EMITTING DEVICE, LIGHT-EMITTING APPARATUS, ELECTRONIC DEVICE, AND LIGHTING DEVICE

BACKGROUND OF THE INVENTION

1. Field of the Invention

One embodiment of the present invention relates to an organic compound, a light-emitting element, a light-emitting device, a display module, a lighting module, a display device, a light-emitting apparatus, an electronic appliance, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

2. Description of the Related Art

Light-emitting devices (organic EL devices) including organic compounds and utilizing electroluminescence (EL) have been put to more practical use. In the basic structure of such light-emitting devices, an organic compound layer containing a light-emitting material (an EL layer) is interposed between a pair of electrodes. Carriers (holes and electrons) are injected by application of voltage to the device, and recombination energy of the carriers is used, whereby light emission can be obtained from the light-emitting material.

Such light-emitting devices are of self-luminous type and thus have advantages over liquid crystal devices, such as high visibility and no need for backlight when used in pixels of a display, and are suitable as flat panel display devices. Displays including such light-emitting devices are also highly advantageous in that they can be thin and lightweight. Moreover, such light-emitting devices also have a feature that response speed is extremely fast.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the organic EL devices also have great potential as planar light sources, which can be used for lighting devices and the like.

Displays and lighting devices including light-emitting devices are suitable for a variety of electronic devices as described above, and research and development of light-emitting devices have progressed for more favorable characteristics.

Low outcoupling efficiency is often a problem in an organic EL device. In particular, the attenuation due to reflection which is caused by a difference in refractive index between adjacent layers is a main cause of a reduction in device efficiency. In order to reduce this effect, a structure including a layer formed using a low refractive index material in an EL layer (see Non-Patent Document 1, for example) has been proposed.

A light-emitting device having this structure can have higher outcoupling efficiency and higher external quantum efficiency than a light-emitting device having a conventional structure; however, it is not easy to form such a layer with a low refractive index in an EL layer without adversely affecting other critical characteristics of the light-emitting device. This is because a low refractive index is in a trade-off relationship with a high carrier-transport property or high reliability of a light-emitting device including a layer with a low refractive index. This problem is caused because the carrier-transport property and reliability of an organic compound largely depend on an unsaturated bond, and an organic compound having many unsaturated bonds tends to have a high refractive index.

REFERENCE

Non-Patent Document

[Non-Patent Document 1] Jaeho Lee et al., "Synergetic electrode architecture for efficient graphene-based flexible organic light-emitting diodes", Nature COMMUNICATIONS, Jun. 2, 2016, DOI: 10.1038/ncomms 11791.

SUMMARY OF THE INVENTION

An object of one embodiment of the present invention is to provide a novel organic compound. Another object of one embodiment of the present invention is to provide a novel organic compound having a carrier-transport property. Another object of one embodiment of the present invention is to provide a novel organic compound having a hole-transport property. Another object of one embodiment of the present invention is to provide an organic compound with a low refractive index. Another object of one embodiment of the present invention is to provide an organic compound with a low refractive index and a carrier-transport property. Another object of one embodiment of the present invention is to provide an organic compound with a low refractive index and a hole-transport property. Another object of one embodiment of the present invention is to provide an organic compound with a low refractive index and a hole-injection property.

Another object of one embodiment of the present invention is to provide a light-emitting device having high emission efficiency. Another object of one embodiment of the present invention is to provide a light-emitting device, a light-emitting apparatus, an electronic appliance, a display device, and an electronic device each having low power consumption.

Note that the description of these objects does not preclude the existence of other objects. One embodiment of the present invention does not necessarily achieve all the objects listed above. Other objects will be apparent from and can be derived from the description of the specification, the drawings, the claims, and the like.

It is only necessary that at least one of the above-described objects be achieved in one embodiment of the present invention.

One embodiment of the present invention is an organic compound represented by General Formula (G1).

[Chemical Formula 1]

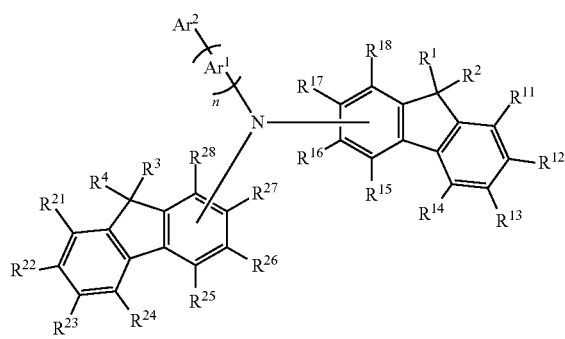

(G1)

In General Formula (G1), Ar$^1$ represents a substituted or unsubstituted arylene group having 6 to 13 carbon atoms in a ring, n represents an integer of 0 or 1, and Ar$^2$ represents an aryl group having 6 to 10 carbon atoms in a ring and includes at least one branched-chain or cyclic alkyl group having 3 to 12 carbon atoms. The total number of carbon atoms of the branched-chain or cyclic alkyl group in Ar$^2$ is more than or equal to 6. R$^1$ to R$^4$ each independently represent an alkyl group having 1 to 6 carbon atoms. R$^{11}$ to R$^{14}$ each independently represent a hydrogen atom or an alkyl group having 1 to 4 carbon atoms. Any one of R$^{15}$ to R$^{18}$ represents a bond directly bonded to a nitrogen atom, and the others each independently represent a hydrogen atom or an alkyl group having 1 to 4 carbon atoms. R$^{21}$ to R$^{24}$ each independently represent a hydrogen atom or an alkyl group having 1 to 4 carbon atoms. Any one of R$^{25}$ to R$^{28}$ represents a bond directly bonded to a nitrogen atom, and the others each independently represent a hydrogen atom or an alkyl group having 1 to 4 carbon atoms.

One embodiment of the present invention is an organic compound represented by General Formula (G2).

[Chemical Formula 2]

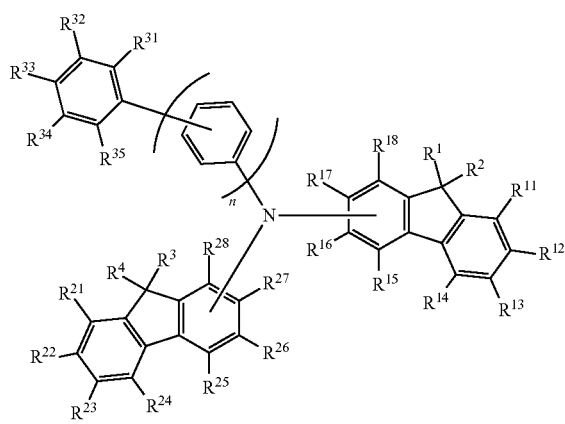

(G2)

In General Formula (G2), R$^1$ to R$^4$ each independently represent an alkyl group having 1 to 6 carbon atoms. R$^{11}$ to R$^{14}$ each independently represent a hydrogen atom or an alkyl group having 1 to 4 carbon atoms. Any one of R$^{15}$ to R$^{18}$ represents a bond directly bonded to a nitrogen atom, and the others each independently represent a hydrogen atom or an alkyl group having 1 to 4 carbon atoms. R$^{21}$ to R$^{24}$ each independently represent a hydrogen atom or an alkyl group having 1 to 4 carbon atoms. Any one of R$^{25}$ to R$^{28}$ represents a bond directly bonded to a nitrogen atom, and the others each independently represent a hydrogen atom or an alkyl group having 1 to 4 carbon atoms. R$^{31}$ to R$^{35}$ each independently represent a hydrogen atom or a branched-chain or cyclic alkyl group having 3 to 12 carbon atoms. The total number of carbon atoms in R$^{31}$ to R$^{35}$ is more than or equal to 6, and n represents an integer of 0 or 1.

One embodiment of the present invention is an organic compound represented by General Formula (G3).

[Chemical Formula 3]

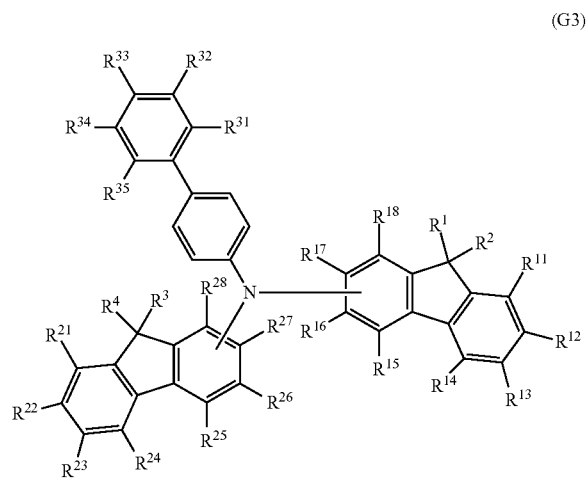

(G3)

In General Formula (G3), R$^1$ to R$^4$ each independently represent an alkyl group having 1 to 6 carbon atoms. R$^{11}$ to R$^{14}$ each independently represent a hydrogen atom or an alkyl group having 1 to 4 carbon atoms. Any one of R$^{15}$ to R$^{18}$ represents a bond directly bonded to a nitrogen atom, and the others each independently represent a hydrogen atom or an alkyl group having 1 to 4 carbon atoms. R$^{21}$ to R$^{24}$ each independently represent a hydrogen atom or an alkyl group having 1 to 4 carbon atoms. Any one of R$^{25}$ to R$^{28}$ represents a bond directly bonded to a nitrogen atom, and the others each independently represent a hydrogen atom or an alkyl group having 1 to 4 carbon atoms. R$^{31}$ to R$^{35}$ each independently represent a hydrogen atom or a branched-chain or cyclic alkyl group having 3 to 12 carbon atoms. The total number of carbon atoms in R$^{31}$ to R$^{35}$ is more than or equal to 6.

One embodiment of the present invention is the organic compound having any of the above structures, in which R$^{11}$ to R$^{14}$ and R$^{21}$ to R$^{24}$ each represent a hydrogen atom, any one of R$^{15}$ to R$^{18}$ represents a bond directly bonded to a nitrogen atom, the others each represent a hydrogen atom, any one of R$^{25}$ to R$^{28}$ represents a bond directly bonded to a nitrogen atom, and the others each represent a hydrogen atom.

One embodiment of the present invention is an organic compound represented by General Formula (G4).

[Chemical Formula 4]

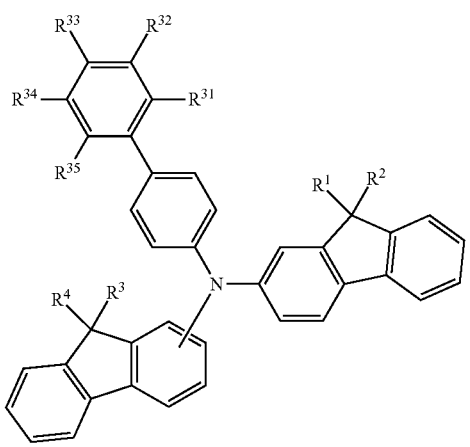

(G4)

In General Formula (G4), $R^1$ to $R^4$ each independently represent an alkyl group having 1 to 6 carbon atoms. $R^{31}$ to $R^{35}$ each independently represent a hydrogen atom or a branched-chain or cyclic alkyl group having 3 to 12 carbon atoms. The total number of carbon atoms in $R^{31}$ to $R^{35}$ is more than or equal to 6.

Another embodiment of the present invention is the organic compound having any of the above structures, in which at least one of $R^{31}$ to $R^{35}$ represents a tert-butyl group or a cyclohexyl group.

Another embodiment of the present invention is the organic compound having any of the above structures, in which $R^{31}$, $R^{33}$, and $R^{35}$ each represent a hydrogen atom, and $R^{32}$ and $R^{34}$ each represent a tert-butyl group or a cyclohexyl group.

Another embodiment of the present invention is the organic compound having any of the above structures, in which $R^{31}$, $R^{32}$, $R^{34}$, and $R^{35}$ each represent a hydrogen atom, and $R^{33}$ represents a tert-butyl group or a cyclohexyl group.

Another embodiment of the present invention is the organic compound having any of the above structures, in which an ordinary refractive index of a layer containing the organic compound with respect to light with a wavelength of 465 nm is higher than or equal to 1.45 and lower than or equal to 1.80.

Another embodiment of the present invention is the organic compound having any of the above structures, in which an ordinary refractive index of a layer containing the organic compound with respect to light with a wavelength of 465 nm is higher than or equal to 1.50 and lower than or equal to 1.75.

Another embodiment of the present invention is the organic compound having any of the above structures, in which an ordinary refractive index of a layer containing the organic compound with respect to light with a wavelength of 520 nm is higher than or equal to 1.45 and lower than or equal to 1.75.

Another embodiment of the present invention is the organic compound having any of the above structures, in which an ordinary refractive index of a layer containing the organic compound with respect to light with a wavelength of 520 nm is higher than or equal to 1.50 and lower than or equal to 1.70.

Another embodiment of the present invention is the organic compound having any of the above structures, in which an ordinary refractive index of a layer containing the organic compound with respect to light with a wavelength of 633 nm is higher than or equal to 1.40 and lower than or equal to 1.75.

Another embodiment of the present invention is the organic compound having any of the above structures, in which an ordinary refractive index of a layer containing the organic compound with respect to light with a wavelength of 633 nm is higher than or equal to 1.45 and lower than or equal to 1.70.

Another embodiment of the present invention is an organic compound represented by Structural Formula (100) or (101).

[Chemical Formulae 5]

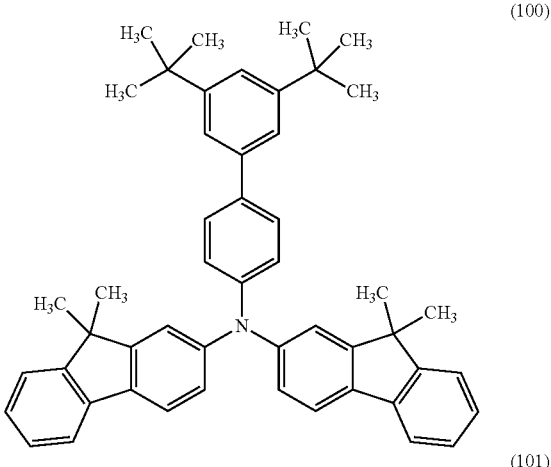

(100)

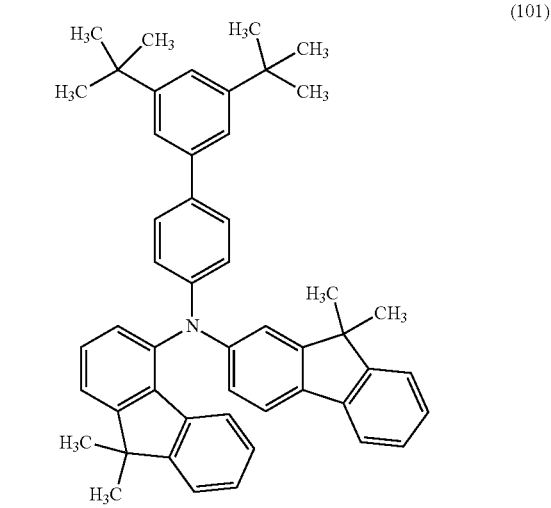

(101)

Another embodiment of the present invention is a light-emitting device including the organic compound having any of the above structures.

Another embodiment of the present invention is an electronic device including the light-emitting device having the above structure, and at least one of a sensor unit, an input unit, and a communication unit.

Another embodiment of the present invention is a light-emitting apparatus including the light-emitting device having the above structure, and at least one of a transistor and a substrate.

Another embodiment of the present invention is a lighting device including the light-emitting device having the above structure and a housing.

Note that the light-emitting apparatus in this specification includes, in its category, an image display device that uses a light-emitting device. The light-emitting apparatus may also include a module in which a light-emitting device over a substrate is provided with a connector such as an anisotropic conductive film or a tape carrier package (TCP), a module in which a printed wiring board is provided at the end of a TCP, and a module in which an integrated circuit (IC) is directly mounted on a light-emitting device by a chip on glass (COG) method. Furthermore, a lighting device or the like may include the light-emitting apparatus.

According to one embodiment of the present invention, a novel organic compound can be provided. According to another embodiment of the present invention, a novel organic compound having a carrier-transport property can be provided. According to another embodiment of the present invention, a novel organic compound having a hole-transport property can be provided. According to another embodiment of the present invention, an organic compound with a low refractive index can be provided. According to another embodiment of the present invention, an organic compound with a low refractive index and a carrier-transport property can be provided. According to another embodiment of the present invention, an organic compound with a low refractive index and a hole-transport property can be provided. According to another embodiment of the present invention, an organic compound with a low refractive index and a hole-injection property can be provided.

According to another embodiment of the present invention, a light-emitting device having high emission efficiency can be provided. According to another embodiment of the present invention, a light-emitting device, a light-emitting apparatus, an electronic appliance, a display device, and an electronic device each having low power consumption can be provided.

Note that the description of these effects does not preclude the existence of other effects. One embodiment of the present invention does not necessarily have all the effects listed above. Other effects will be apparent from and can be derived from the description of the specification, the drawings, the claims, and the like.

BRIEF DESCRIPTION OF THE DRAWINGS

In the accompanying drawings:

FIGS. 1A to 1E illustrate structures of light-emitting devices of an embodiment;

DETAILED DESCRIPTION OF THE INVENTION

Figure 2A:
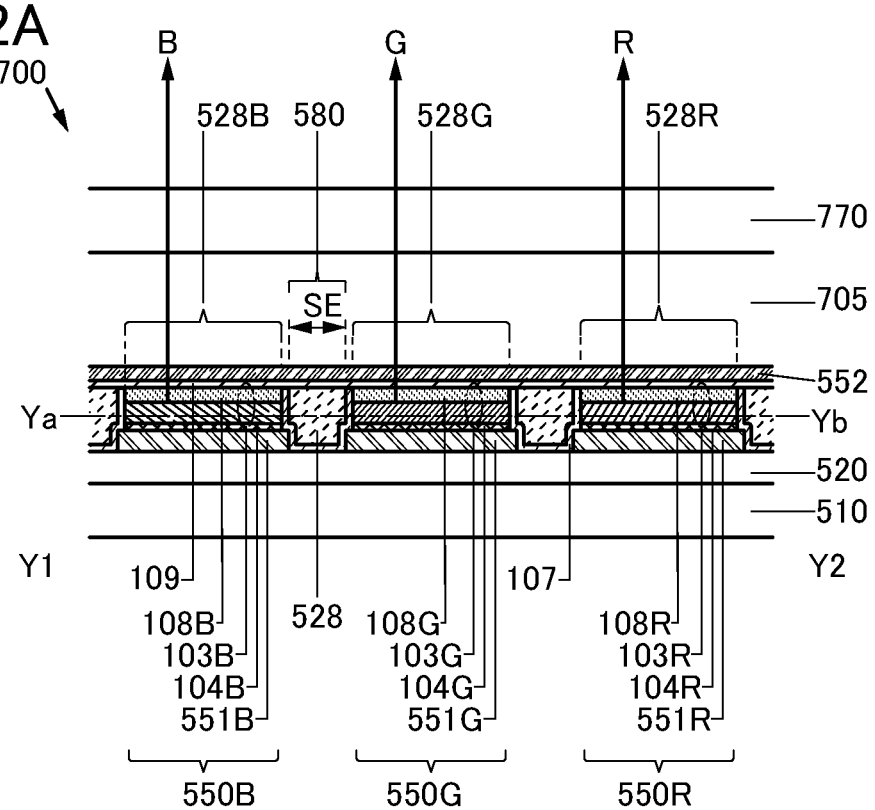
FIGS. 2A to 2C illustrate a light-emitting apparatus of an embodiment.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be construed as being limited to the description in the following embodiments.

Embodiment 1

Among organic compounds having a carrier-transport property that can be used for an organic EL device, di-[4-(N,N-ditolyl-amino)-phenyl]cyclohexane (abbreviation: TAPC) is one of materials with a low refractive index. The use of such a material with a low refractive index for an EL layer enables a light-emitting device to have high external quantum efficiency; thus, with TAPC, a light-emitting device with high external quantum efficiency can be obtained.

In general, a high carrier-transport property and a low refractive index have a trade-off relationship. This is because the carrier-transport property of an organic compound largely depends on an unsaturated bond, and an organic compound having many unsaturated bonds tends to have a high refractive index. TAPC has a perfect balance of a hole-transport property and a low refractive index; however, in a compound including 1,1-disubstituted cyclohexane, such as TAPC, two bulky substituents are bonded to a carbon atom of cyclohexane; thus, steric repulsion becomes larger and instability of the molecule itself is induced. This causes a reliability problem. In addition, TAPC has a skeleton structure including cyclohexane and simple benzene rings and thus has a low glass transition temperature (Tg) and a heat resistance problem.

One of the possible methods for obtaining a hole-transport material with high heat resistance and high reliability is introducing an unsaturated hydrocarbon group, particularly a cyclic unsaturated hydrocarbon group, into a molecule. Meanwhile, in order to obtain a low refractive index material, a substituent that can lower a refractive index of a molecule is preferably introduced. Examples of the substituent include a saturated hydrocarbon group and a cyclic saturated hydrocarbon group.

A material used as a carrier-transport material for an organic EL device preferably has a skeleton with a high carrier-transport property, and an aromatic amine skeleton is particularly preferable because of its high hole-transport property. For a higher hole-transport property, two amine skeletons can be introduced as another method. However, as in the above-described TAPC, the diamine structure sometimes adversely affects the reliability depending on the substituents arranged around the amine skeletons.

The present inventors have found, as an organic compound that overcomes the trade-off and has a carrier-transport property, a carrier-injection property, a low refractive index, and high reliability, a triarylamine compound that includes two fluorenyl groups and an aryl group having a branched-chain or cyclic alkyl group as a substituent. The triarylamine compound has high reliability equivalent to those of conventional materials for a hole-transport layer with a normal refractive index. Adjusting the number of alkyl groups and the substitution sites in the triarylamine compound allows the material to have more excellent properties.

The triarylamine compound including a fluorenyl group tends to have a high hole-transport property. Two fluorenyl groups included in the molecular structure further increase a hole-transport property, and a light-emitting device formed using the triarylamine compound as a material for a hole-transport layer can have low driving voltage. In addition, it is preferable that a fluorenyl group be directly bonded to a nitrogen atom of amine because this contributes to a shallower highest occupied molecular orbital (HOMO) level of the molecule and thus facilitates hole transfer.

In general, a compound to which a straight-chain alkyl group is introduced tends to have lower Tg and/or melting point than a compound to which a branched-chain or cyclic alkyl group corresponding to (e.g., with substantially the same number of carbon atoms as) the straight-chain alkyl group is introduced. The lower Tg sometimes leads to lower heat resistance of an organic EL material. An EL device formed using the organic EL material is desired to show stable physical properties under various circumstances in our life; thus, a material with higher Tg is preferably selected from materials having substantially the same properties. The triarylamine compound of one embodiment of the present invention including a branched-chain or cyclic alkyl group can keep high Tg and have high heat resistance as compared with the case where a straight-chain alkyl group is introduced.

That is, one embodiment of the present invention is an organic compound represented by General Formula (G1).

[Chemical Formula 6]

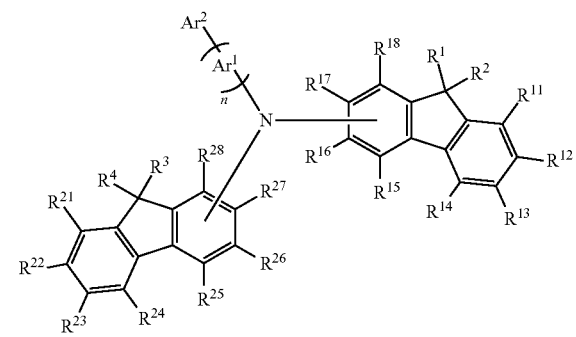

(G1)

In General Formula (G1), $Ar^1$ represents a substituted or unsubstituted arylene group having 6 to 13 carbon atoms in a ring, n represents an integer of 0 or 1, and $Ar^2$ represents an aryl group having 6 to 10 carbon atoms in a ring and includes at least one branched-chain or cyclic alkyl group having 3 to 12 carbon atoms. The total number of carbon atoms of the branched-chain or cyclic alkyl group in $Ar^2$ is more than or equal to 6. $R^1$ to $R^4$ each independently represent an alkyl group having 1 to 6 carbon atoms. $R^{11}$ to $R^{14}$ each independently represent a hydrogen atom or an alkyl group having 1 to 4 carbon atoms. Any one of $R^{15}$ to $R^{18}$ represents a bond directly bonded to a nitrogen atom, and the others each independently represent a hydrogen atom or an alkyl group having 1 to 4 carbon atoms. $R^{21}$ to $R^{24}$ each independently represent a hydrogen atom or an alkyl group having 1 to 4 carbon atoms. Any one of $R^{25}$ to $R^{28}$ represents a bond directly bonded to a nitrogen atom, and the others each independently represent a hydrogen atom or an alkyl group having 1 to 4 carbon atoms.

Specific examples of the arylene group having 6 to 13 carbon atoms in a ring that can be used as $Ar^1$ in General Formula (G1) include a phenylene group, a naphthylene group, and a fluorenediyl group. In the case where the arylene group having 6 to 13 carbon atoms in a ring has a substituent, the substituent is an alkyl group having 1 to 4 carbon atoms.

Specific examples of the aryl group having 6 to 10 carbon atoms in a ring that can be used as $Ar^2$ include a phenyl group and a naphthyl group.

Examples of the branched-chain alkyl group having 3 to 12 carbon atoms that is included in $Ar^2$ include an isopropyl group, an isobutyl group, a sec-butyl group, a tert-butyl group, an isopentyl group, a sec-pentyl group, a tert-pentyl group, a neo-pentyl group, an isohexyl group, a sec-hexyl group, a tert-hexyl group, an isoheptyl group, a sec-heptyl group, a tert-heptyl group, a neo-heptyl group, an isooctyl group, a sec-octyl group, a tert-octyl group, a neo-octyl group, an isononyl group, a sec-nonyl group, a tert-nonyl group, a neo-nonyl group, an isodecyl group, a sec-decyl group, a tert-decyl group, an isoundecyl group, a sec-undecyl group, a tert-undecyl group, an isododecyl group, a sec-dodecyl group, and a tert-dodecyl group, and a tert-butyl group is particularly preferable.

As the cyclic alkyl group having 3 to 12 carbon atoms that is included in $Ar^2$, specifically, a cyclopropyl group, a methylisopropyl group, a cyclobutyl group, a methylcyclobutyl group, a cyclopentyl group, a methylcyclopentyl group, an isopropylcyclopentyl group, a tert-butylcyclopropyl group, a cyclohexyl group, a methylcyclohexyl group, an isopropylcyclohexyl group, a tert-butylcyclohexyl group, a cycloheptyl group, a methylcycloheptyl group, an isopropylcycloheptyl group, a tert-butylcycloheptyl group, a cyclooctyl group, a methylcyclooctyl group, an isopropylcyclohexyl group, a tert-butylcyclooctyl group, a cyclononyl group, a methylcyclononyl group, an isopropylcyclononyl group, a cyclodecyl group, a methylcyclodecyl group, a cycloundecyl group, a methylcycloundecyl group, a cyclododecyl group, or the like can be used. For a lower refractive index, a cycloalkyl group having 6 or more carbon atoms is preferable, and a cyclohexyl group is particularly preferable.

One embodiment of the present invention is an organic compound represented by General Formula (G2).

[Chemical Formula 7]

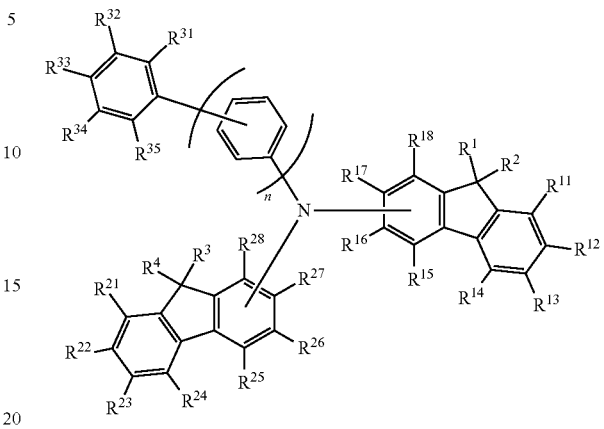

(G2)

In General Formula (G2), $R^1$ to $R^4$ each independently represent an alkyl group having 1 to 6 carbon atoms. $R^{11}$ to $R^{14}$ each independently represent a hydrogen atom or an alkyl group having 1 to 4 carbon atoms. Any one of $R^{15}$ to $R^{18}$ represents a bond directly bonded to a nitrogen atom, and the others each independently represent a hydrogen atom or an alkyl group having 1 to 4 carbon atoms. $R^{21}$ to $R^{24}$ each independently represent a hydrogen atom or an alkyl group having 1 to 4 carbon atoms. Any one of $R^{25}$ to $R^{28}$ represents a bond directly bonded to a nitrogen atom, and the others each independently represent a hydrogen atom or an alkyl group having 1 to 4 carbon atoms. $R^{31}$ to $R^{35}$ each independently represent a hydrogen atom or a branched-chain or cyclic alkyl group having 3 to 12 carbon atoms. The total number of carbon atoms in $R^{31}$ to $R^{35}$ is more than or equal to 6, and n represents an integer of 0 or 1.

Examples of the branched-chain alkyl group having 3 to 12 carbon atoms in General Formula (G2) include an isopropyl group, an isobutyl group, a sec-butyl group, a tert-butyl group, an isopentyl group, a sec-pentyl group, a tert-pentyl group, a neo-pentyl group, an isohexyl group, a sec-hexyl group, a tert-hexyl group, an isoheptyl group, a sec-heptyl group, a tert-heptyl group, a neo-heptyl group, an isooctyl group, a sec-octyl group, a tert-octyl group, a neo-octyl group, an isononyl group, a sec-nonyl group, a tert-nonyl group, a neo-nonyl group, an isodecyl group, a sec-decyl group, a tert-decyl group, an isoundecyl group, a sec-undecyl group, a tert-undecyl group, an isododecyl group, a sec-dodecyl group, and a tert-dodecyl group, and a tert-butyl group is particularly preferable.

As the cyclic alkyl group having 3 to 12 carbon atoms that is included in $Ar^2$, specifically, a cyclopropyl group, a methylisopropyl group, a cyclobutyl group, a methylcyclobutyl group, a cyclopentyl group, a methylcyclopentyl group, an isopropylcyclopentyl group, a tert-butylcyclopropyl group, a cyclohexyl group, a methylcyclohexyl group, an isopropylcyclohexyl group, a tert-butylcyclohexyl group, a cycloheptyl group, a methylcycloheptyl group, an isopropylcycloheptyl group, a tert-butylcycloheptyl group, a cyclooctyl group, a methylcyclooctyl group, an isopropylcyclohexyl group, a tert-butylcyclooctyl group, a cyclononyl group, a methylcyclononyl group, an isopropylcyclononyl group, a cyclodecyl group, a methylcyclodecyl group, a cycloundecyl group, a methylcycloundecyl group, a cyclododecyl group, or the like can be used. For a lower refractive index, a cycloalkyl group having 6 or more carbon atoms is preferable, and a cyclohexyl group is particularly preferable.

One embodiment of the present invention is an organic compound represented by General Formula (G3).

[Chemical Formula 8]

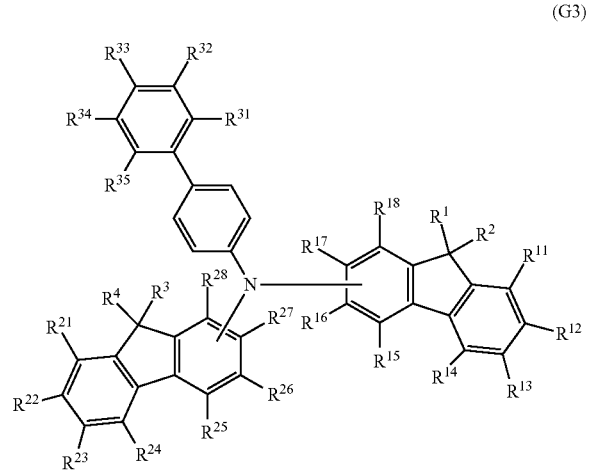

(G3)

In General Formula (G3), $R^1$ to $R^4$ each independently represent an alkyl group having 1 to 6 carbon atoms. $R^{11}$ to $R^{14}$ each independently represent a hydrogen atom or an alkyl group having 1 to 4 carbon atoms. Any one of $R^{15}$ to $R^{18}$ represents a bond directly bonded to a nitrogen atom, and the others each independently represent a hydrogen atom or an alkyl group having 1 to 4 carbon atoms. $R^{21}$ to $R^{24}$ each independently represent a hydrogen atom or an alkyl group having 1 to 4 carbon atoms. Any one of $R^{25}$ to $R^{28}$ represents a bond directly bonded to a nitrogen atom, and the others each independently represent a hydrogen atom or an alkyl group having 1 to 4 carbon atoms. $R^{31}$ to $R^{35}$ each independently represent a hydrogen atom or a branched-chain or cyclic alkyl group having 3 to 12 carbon atoms. The total number of carbon atoms in $R^{31}$ to $R^{35}$ is more than or equal to 6.

Examples of the branched-chain alkyl group having 3 to 12 carbon atoms in General Formula (G3) include an isopropyl group, an isobutyl group, a sec-butyl group, a tert-butyl group, an isopentyl group, a sec-pentyl group, a tert-pentyl group, a neo-pentyl group, an isohexyl group, a sec-hexyl group, a tert-hexyl group, an isoheptyl group, a sec-heptyl group, a tert-heptyl group, a neo-heptyl group, an isooctyl group, a sec-octyl group, a tert-octyl group, a neo-octyl group, an isononyl group, a sec-nonyl group, a tert-nonyl group, a neo-nonyl group, an isodecyl group, a sec-decyl group, a tert-decyl group, an isoundecyl group, a sec-undecyl group, a tert-undecyl group, an isododecyl group, a sec-dodecyl group, and a tert-dodecyl group, and a tert-butyl group is particularly preferable.

As the cyclic alkyl group having 3 to 12 carbon atoms that is included in $Ar^2$, specifically, a cyclopropyl group, a methylisopropyl group, a cyclobutyl group, a methylcyclobutyl group, a cyclopentyl group, a methylcyclopentyl group, an isopropylcyclopentyl group, a tert-butylcyclopropyl group, a cyclohexyl group, a methylcyclohexyl group, an isopropylcyclohexyl group, a tert-butylcyclohexyl group, a cycloheptyl group, a methylcycloheptyl group, an isopropylcycloheptyl group, a tert-butylcycloheptyl group, a cyclooctyl group, a methylcyclooctyl group, an isopropylcyclohexyl group, a tert-butylcyclooctyl group, a cyclononyl group, a methylcyclononyl group, an isopropylcyclononyl group, a cyclodecyl group, a methylcyclodecyl group, a cycloundecyl group, a methylcycloundecyl group, a cyclododecyl group, or the like can be used. For a lower refractive index, a cycloalkyl group having 6 or more carbon atoms is preferable, and a cyclohexyl group is particularly preferable.

One embodiment of the present invention is the organic compound represented by any of General Formulae (G1), (G2), and (G3), in which $R^{11}$ to $R^{14}$ and $R^{21}$ to $R^{24}$ each represent a hydrogen atom, any one of $R^{15}$ to $R^{18}$ represents a bond directly bonded to a nitrogen atom, the others each represent a hydrogen atom, any one of $R^{25}$ to $R^{28}$ represents a bond directly bonded to a nitrogen atom, and the others each represent a hydrogen atom.

One embodiment of the present invention is an organic compound represented by General Formula (G4).

[Chemical Formula 9]

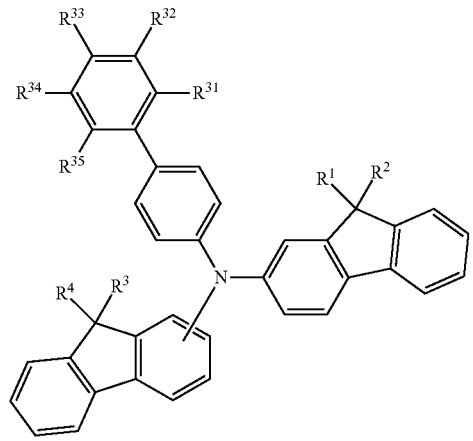

(G4)

In General Formula (G4), $R^1$ to $R^4$ each independently represent an alkyl group having 1 to 6 carbon atoms. $R^{31}$ to $R^{35}$ each independently represent a hydrogen atom or a branched-chain or cyclic alkyl group having 3 to 12 carbon atoms. The total number of carbon atoms in $R^{31}$ to $R^{35}$ is more than or equal to 6.

Examples of the branched-chain alkyl group having 3 to 12 carbon atoms in General Formula (G4) include an isopropyl group, an isobutyl group, a sec-butyl group, a tert-butyl group, an isopentyl group, a sec-pentyl group, a tert-pentyl group, a neo-pentyl group, an isohexyl group, a sec-hexyl group, a tert-hexyl group, an isoheptyl group, a sec-heptyl group, a tert-heptyl group, a neo-heptyl group, an isooctyl group, a sec-octyl group, a tert-octyl group, a neo-octyl group, an isononyl group, a sec-nonyl group, a tert-nonyl group, a neo-nonyl group, an isodecyl group, a sec-decyl group, a tert-decyl group, an isoundecyl group, a sec-undecyl group, a tert-undecyl group, an isododecyl group, a sec-dodecyl group, and a tert-dodecyl group, and a tert-butyl group is particularly preferable.

As the cyclic alkyl group having 3 to 12 carbon atoms that is included in $Ar^2$, specifically, a cyclopropyl group, a methylisopropyl group, a cyclobutyl group, a methylcyclobutyl group, a cyclopentyl group, a methylcyclopentyl group, an isopropylcyclopentyl group, a tert-butylcyclopropyl group, a cyclohexyl group, a methylcyclohexyl group, an isopropylcyclohexyl group, a tert-butylcyclohexyl group, a cycloheptyl group, a methylcycloheptyl group, an isopropylcycloheptyl group, a tert-butylcycloheptyl group, a cyclooctyl group, a methylcyclooctyl group, an isopropylcyclohexyl group, a tert-butylcyclooctyl group, a cyclononyl group, a methylcyclononyl group, an isopropylcyclononyl group, a cyclodecyl group, a methylcyclodecyl group, a cycloundecyl group, a methylcycloundecyl group, a cyclododecyl group, or the like can be used. For a lower refractive index, a cycloalkyl group having 6 or more carbon atoms is preferable, and a cyclohexyl group is particularly preferable.

One embodiment of the present invention is the organic compound represented by any of General Formulae (G2), (G3), and (G4), in which at least one of $R^{31}$ to $R^{35}$ represents a tert-butyl group or a cyclohexyl group.

One embodiment of the present invention is the organic compound represented by any of General Formulae (G2), (G3), and (G4), in which $R^{31}$, $R^{33}$, and $R^{35}$ each represent a hydrogen atom, and $R^{32}$ and $R^{34}$ each represent a tert-butyl group or a cyclohexyl group.

One embodiment of the present invention is the organic compound represented by any of General Formulae (G2), (G3), and (G4), in which $R^{31}$, $R^{32}$, $R^{34}$, and $R^{35}$ each represent a hydrogen atom, and $R^{33}$ represents a tert-butyl group or a cyclohexyl group.

The organic compound of one embodiment of the present invention having the above-described structure can have an extremely low refractive index, and the range of the refractive index is as follows: the ordinary refractive index of a layer formed of the organic compound with respect to light with a wavelength of 465 nm is higher than or equal to 1.45 and lower than or equal to 1.80, preferably higher than or equal to 1.50 and lower than or equal to 1.75; the ordinary refractive index of the layer with respect to light with a wavelength of 520 nm is higher than or equal to 1.45 and lower than or equal to 1.75, preferably higher than or equal to 1.50 and lower than or equal to 1.70; and the ordinary refractive index of the layer with respect to light with a wavelength of 633 nm is higher than or equal to 1.40 and lower than or equal to 1.75, preferably higher than or equal to 1.45 and lower than or equal to 1.70.

In the case where the material has anisotropy, the refractive index with respect to an ordinary ray might differ from that with respect to an extraordinary ray. When a thin film to be measured is in such a state, anisotropy analysis can be performed to separately calculate the ordinary refractive index and the extraordinary refractive index. In this specification, when the measured material has both the ordinary refractive index and the extraordinary refractive index, the ordinary refractive index is used as an indicator.

The organic compound of one embodiment of the present invention having the above-described structure has a favorable hole-transport property and a low refractive index and thus can be suitably used as a material for a hole-transport layer or a hole-injection layer of an organic EL device. Since an organic EL device formed using the material for a hole-transport layer or a hole-injection layer includes a hole-transport layer or a hole-injection layer with a low refractive index, a light-emitting device having high emission efficiency, i.e., high external quantum efficiency, high current efficiency, and a high blue index, can be obtained.

The organic compound of one embodiment of the present invention having the above-described structure has a relatively shallow HOMO level. In general, the HOMO levels of materials for a hole-injection layer and a layer adjacent to a light-emitting layer, such as a hole-transport layer, are close to the HOMO level of a material for the light-emitting layer and become shallow in an appropriate range; thus, a property of accepting holes from these layers to the light-emitting layer is improved. Meanwhile, using a material with a shallow HOMO level as a material for a hole-transport layer in contact with a light-emitting layer in an organic EL device results in formation of an exciplex with a low energy level between the HOMO level of the material for the hole-transport layer and the lowest unoccupied molecular orbital (LUMO) level of a material for the light-emitting layer, so that the emission efficiency sometimes decreases.

However, the organic compound of one embodiment of the present invention includes a bulky alkyl group. Thus, when the organic compound of one embodiment of the present invention is used as a material for a hole-transport layer in contact with a light-emitting layer in an organic EL device, the interaction between the materials for the light-emitting layer and the hole-transport layer adjacent to each other can be lower than that in a typical organic EL device owing to a steric effect of the bulky alkyl group. This inhibits formation of an exciplex by the HOMO level of the material for the hole-transport layer and the LUMO level of the material for the light-emitting layer, producing an effect of preventing an emission efficiency decrease due to the formation of the exciplex. Accordingly, with the use of the organic compound of one embodiment of the present invention, an organic EL device with low driving voltage and high efficiency can be manufactured.

The range of the HOMO level of the organic compound of one embodiment of the present invention is preferably higher than or equal to −5.50 eV and lower than or equal to −5.30 eV, further preferably higher than or equal to −5.40 eV and lower than or equal to −5.30 eV. Thus, the organic compound of one embodiment of the present invention can be suitably used as a material for a hole-transport layer in contact with a light-emitting layer in an organic EL device.

The organic compound of one embodiment of the present invention having the above-described structure can have a high giant surface potential (GSP); the range of GSP of a layer formed of the organic compound is higher than or equal to 20 mV/nm.

The giant surface potential refers to a phenomenon in which a surface potential of an evaporated film increases in proportion to a film thickness. In order to treat the surface potential as a value independent of a film thickness, a value obtained by dividing the surface potential of an evaporated film by the film thickness, that is, the potential gradient (slope) of a surface potential of an evaporated film, is used. In this specification, the potential gradient of a surface potential of an evaporated film is denoted by GSP (mV/nm).

In an organic semiconductor device including at least two layers (a first hole-transport layer and a second hole-transport layer) stacked in contact with each other, when holes flow from the first hole-transport layer side to the second hole-transport layer side and the difference between GSP of an organic compound in the first hole-transport layer (GSP1) and GSP of an organic compound in the second hole-transport layer (GSP2), i.e., AGSP (GSP2-GSP1), is a positive value, hole injection is facilitated and the organic semiconductor device can have low driving voltage. Accordingly, in such a case, the organic compound of one embodiment of the present invention can be suitably used for the first hole-transport layer.

The organic compound of one embodiment of the present invention preferably satisfies at least two of the above-described ranges of the refractive index, the HOMO level, and the GSP, and further preferably satisfies all of them.
Next, specific examples of the organic compounds of one embodiment of the present invention having the above structures are shown below.
[Chemical Formulae 10]
(100)
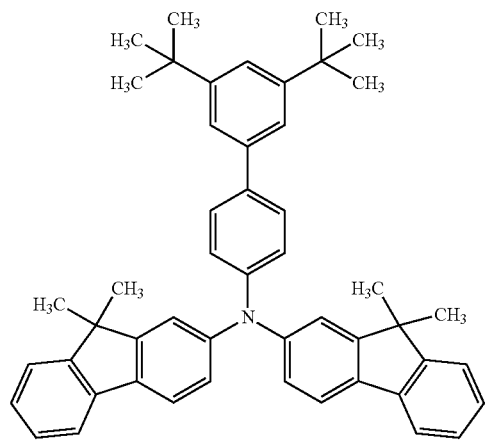
(102)
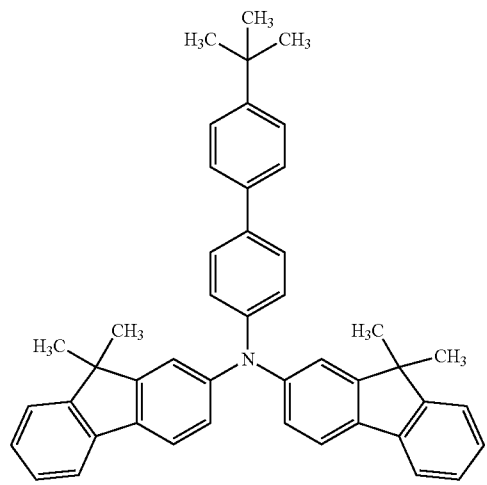
(103)
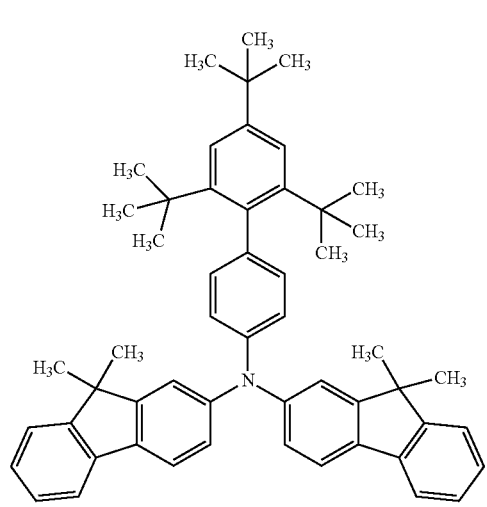
(104)
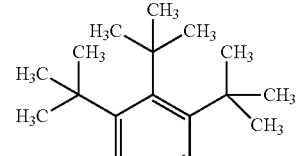
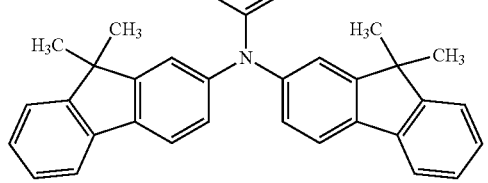
(105)
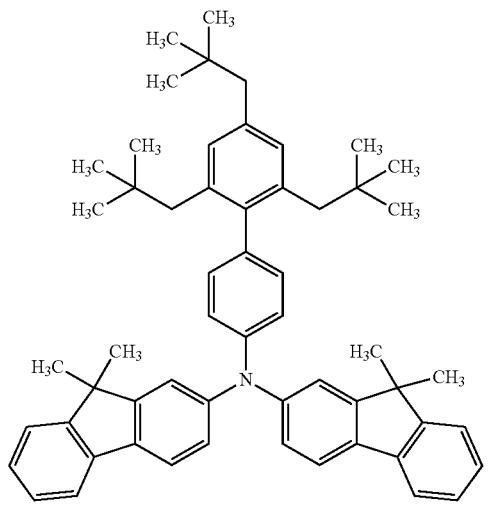
(106)
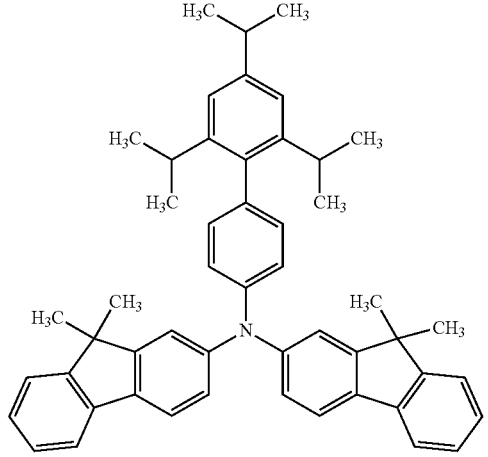

[Chemical Formulae 11]
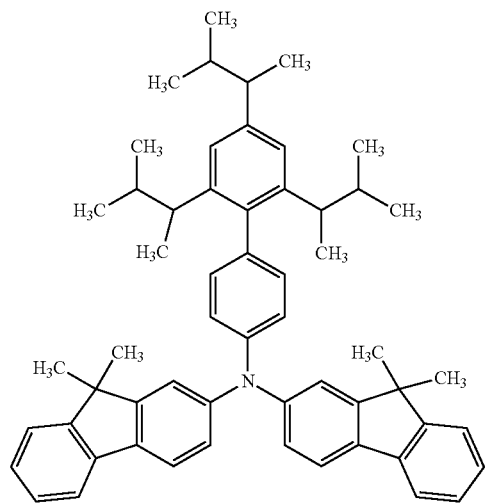
(107)
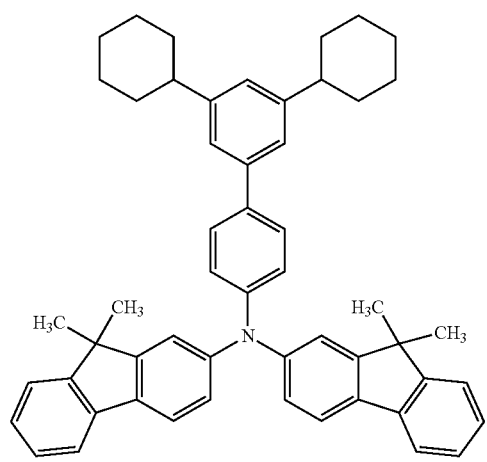
(108)
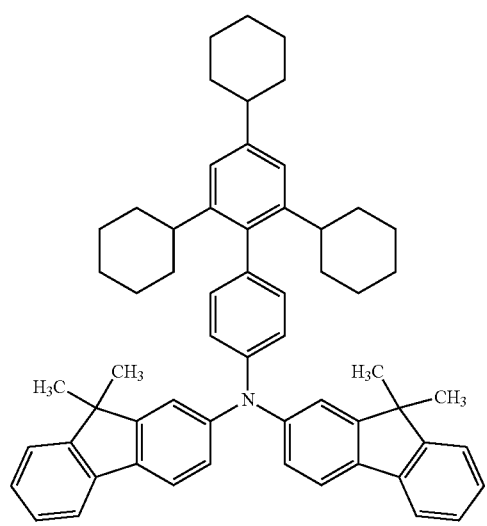
(109)
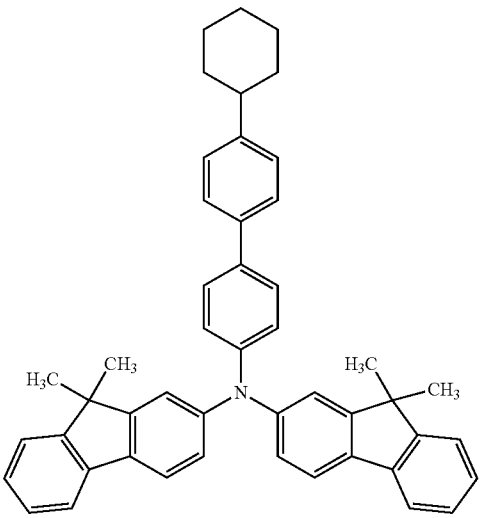
(110)
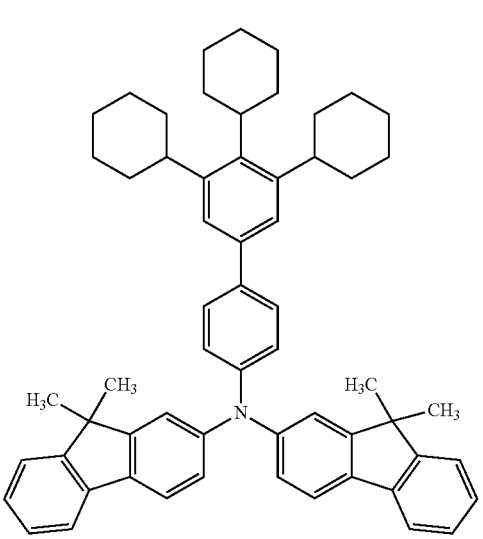
(111)
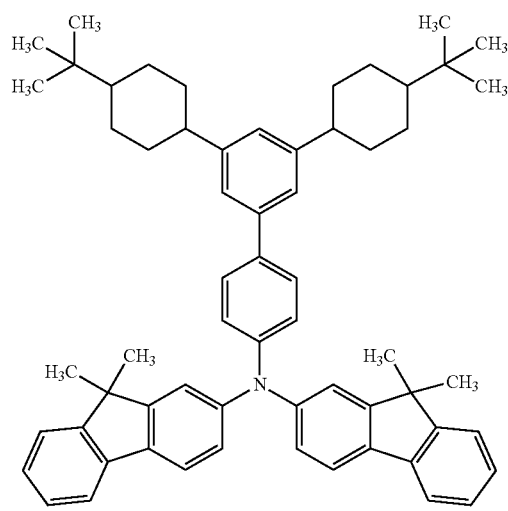
(112)

(113)
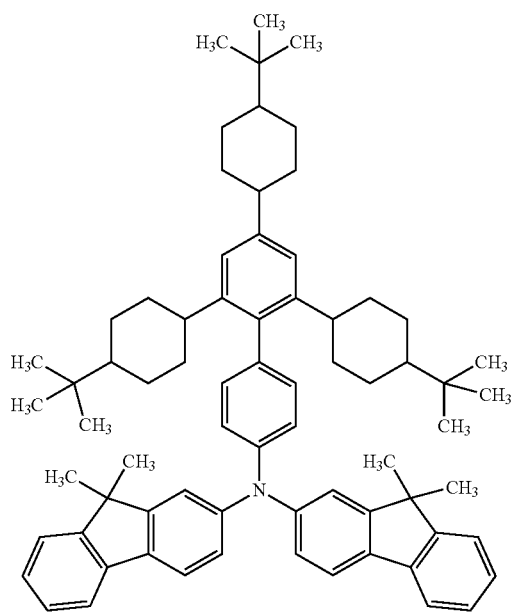
(114)
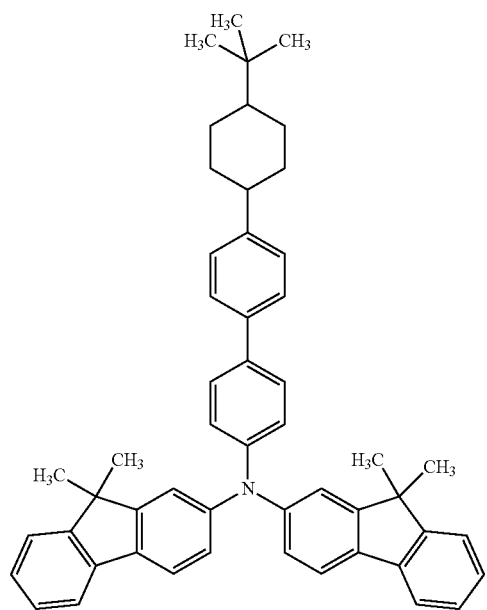
(115)
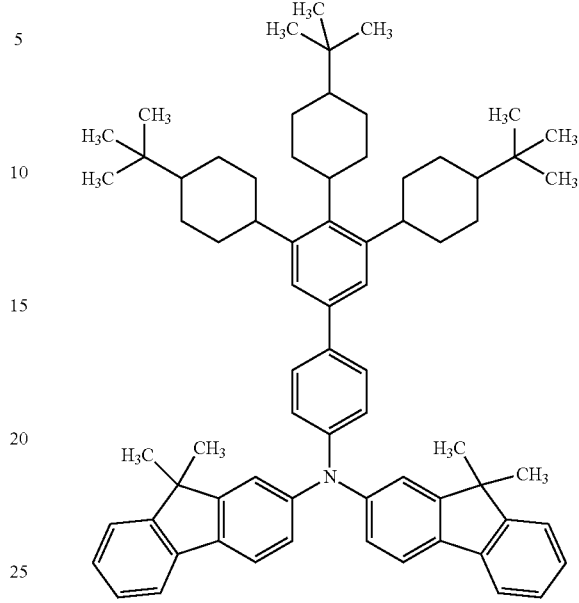
(116)
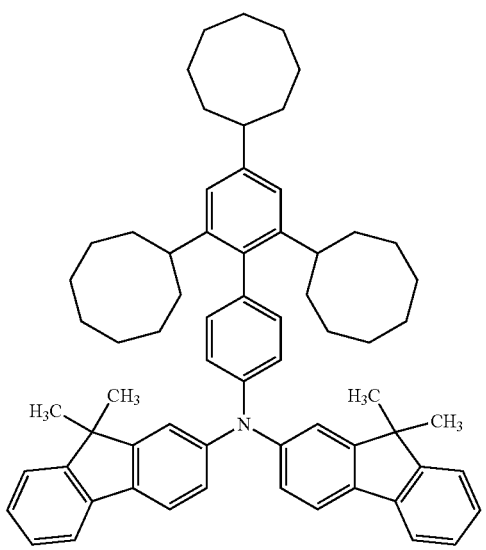

[Chemical Formulae 12]
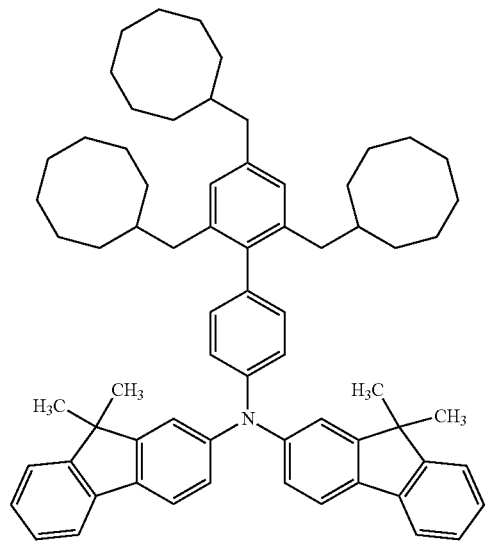
(117)
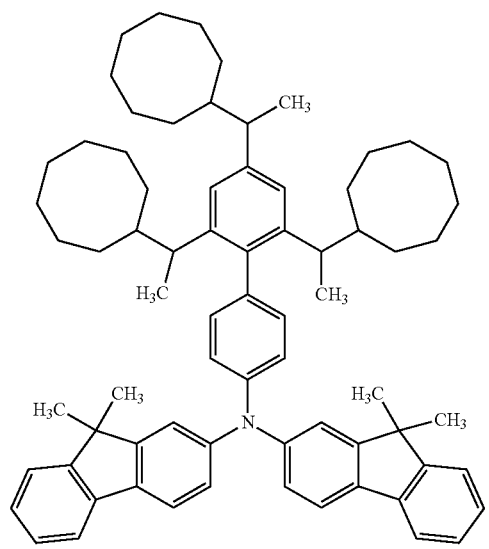
(118)
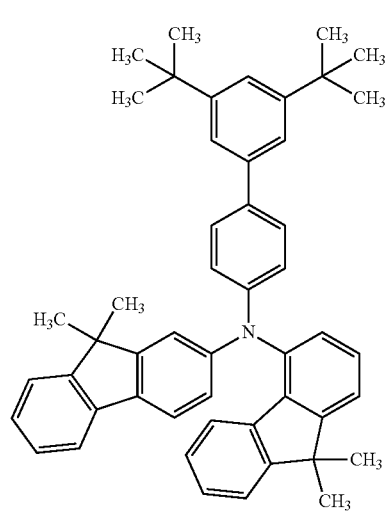
(101)
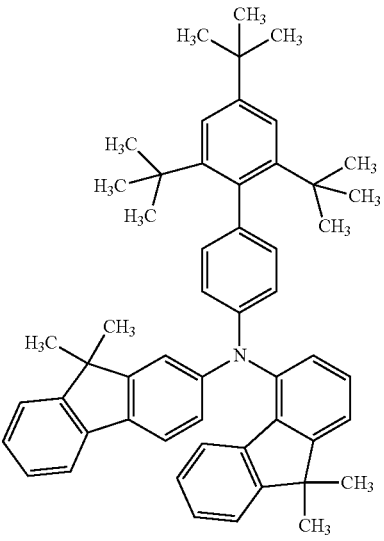
(119)
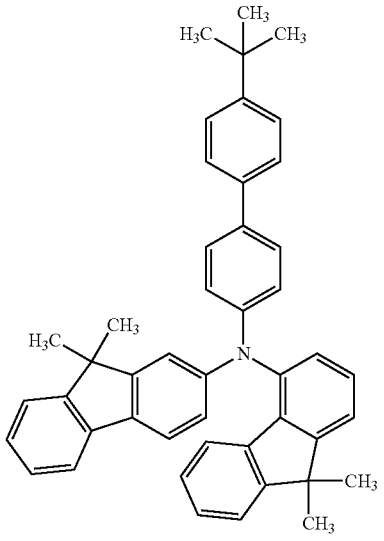
(120)
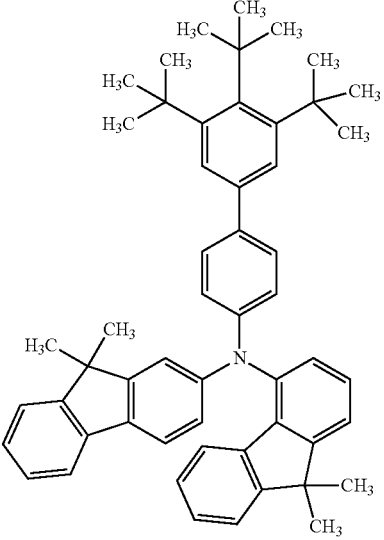
(121)

(122)
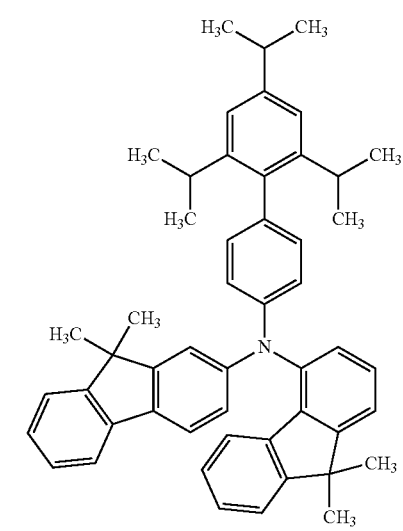
(125)
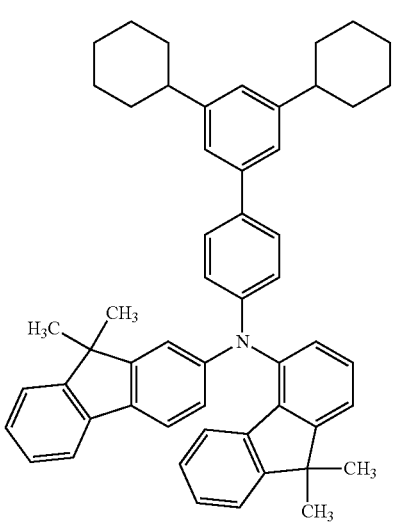
(123)
(124)
(126)
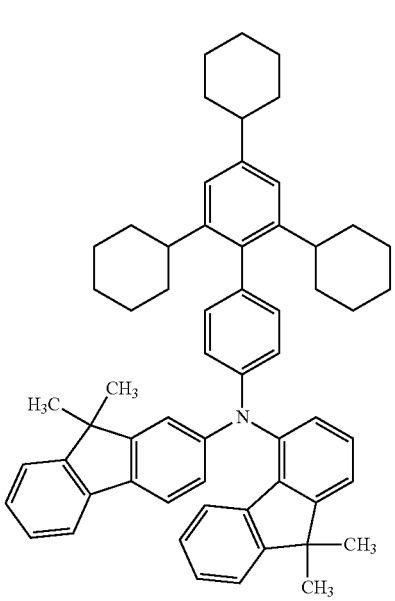

[Chemical Formulae 13]
(127)
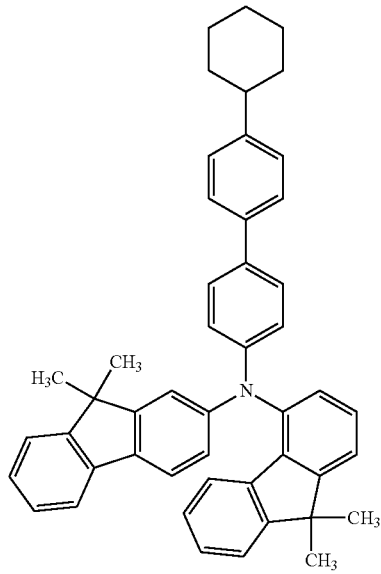
(128)
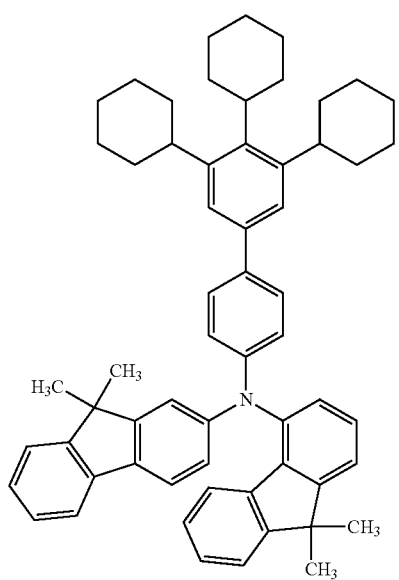
(129)
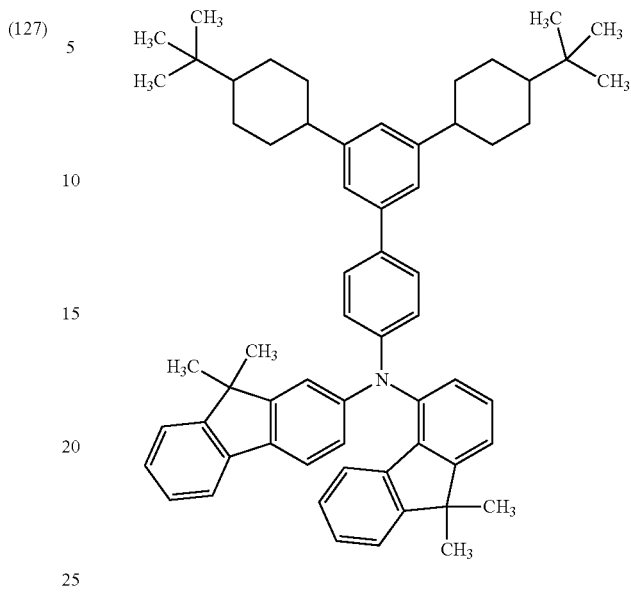
(130)
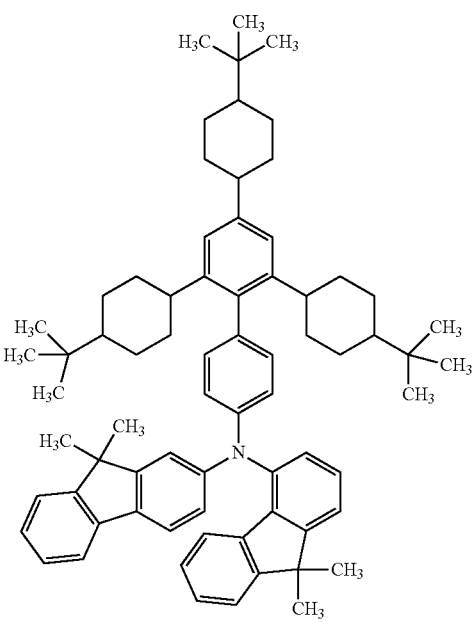

-continued
(131)
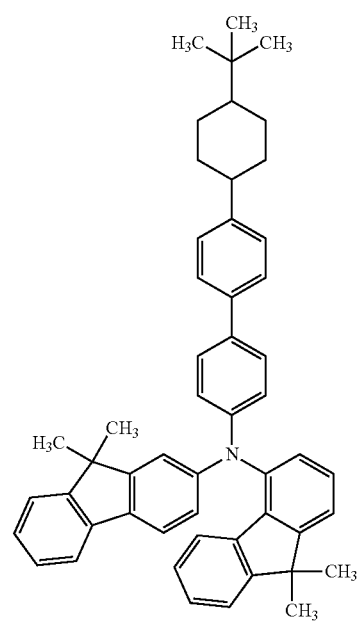
(133)
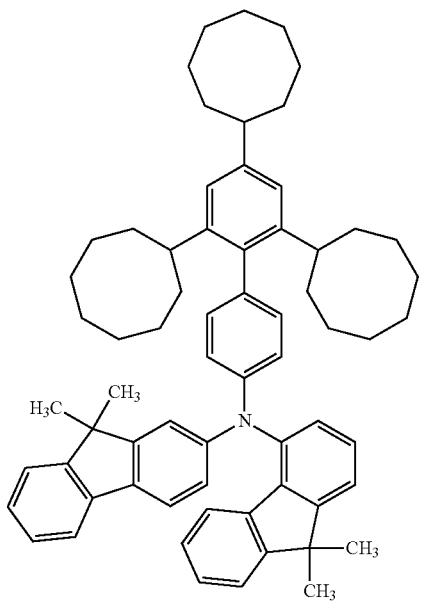
(132)
(134)
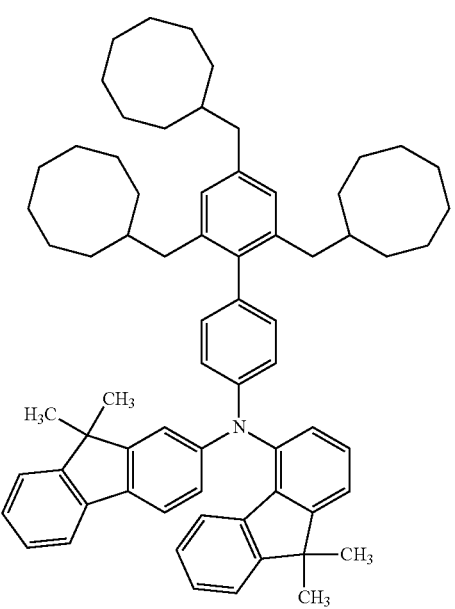

-continued (135)

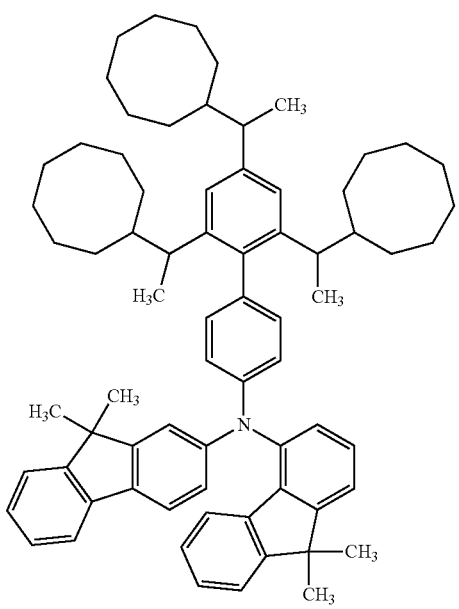

The organic compounds represented by Structural Formulae (100) to (135) are examples of the organic compounds represented by General Formulae (G1) to (G4). The organic compound of one embodiment of the present invention is not limited thereto.

Next, a method for synthesizing the organic compound of one embodiment of the present invention represented by General Formula (G1) will be described.

[Chemical Formula 14]

(G1)

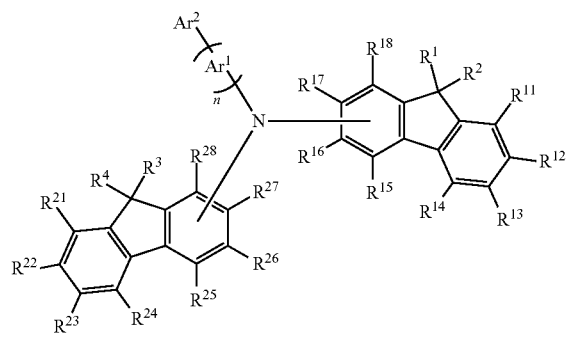

In General Formula (G1), $Ar^1$ represents a substituted or unsubstituted arylene group having 6 to 13 carbon atoms in a ring, n represents an integer of 0 or 1, and $Ar^2$ represents an aryl group having 6 to 10 carbon atoms in a ring and includes at least one branched-chain or cyclic alkyl group having 3 to 12 carbon atoms. The total number of carbon atoms of the branched-chain or cyclic alkyl group in $Ar^2$ is more than or equal to 6. $R^1$ to $R^4$ each independently represent an alkyl group having 1 to 6 carbon atoms. $R^{11}$ to $R^{14}$ each independently represent a hydrogen atom or an alkyl group having 1 to 4 carbon atoms. Any one of $R^{15}$ to $R^{18}$ represents a bond directly bonded to a nitrogen atom, and the others each independently represent a hydrogen atom or an alkyl group having 1 to 4 carbon atoms. $R^{21}$ to $R^{24}$ each independently represent a hydrogen atom or an alkyl group having 1 to 4 carbon atoms. Any one of $R^{25}$ to $R^{28}$ represents a bond directly bonded to a nitrogen atom, and the others each independently represent a hydrogen atom or an alkyl group having 1 to 4 carbon atoms.

As shown in the following synthesis scheme, difluorenylamine and an organic halide are coupled using a metal catalyst, a metal, or a metal compound in the presence of a base, so that the organic compound represented by General Formula (G1) can be obtained.

[Chemical Formula 15]

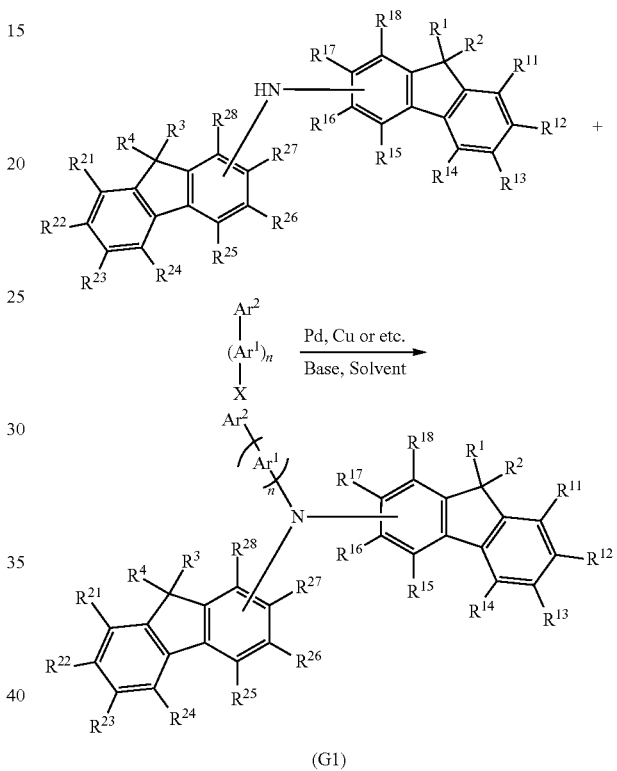

(G1)

In the above scheme, $Ar^1$ represents a substituted or unsubstituted arylene group having 6 to 13 carbon atoms in a ring, n represents an integer of 0 or 1, and $Ar^2$ represents an aryl group having 6 to 10 carbon atoms in a ring and includes at least one branched-chain or cyclic alkyl group having 3 to 12 carbon atoms. The total number of carbon atoms of the branched-chain or cyclic alkyl group in $Ar^2$ is more than or equal to 6. $R^1$ to $R^4$ each independently represent an alkyl group having 1 to 6 carbon atoms. $R^{11}$ to $R^{14}$ each independently represent a hydrogen atom or an alkyl group having 1 to 4 carbon atoms. Any one of $R^{15}$ to $R^{18}$ represents a bond directly bonded to a nitrogen atom, and the others each independently represent a hydrogen atom or an alkyl group having 1 to 4 carbon atoms. $R^{21}$ to $R^{24}$ each independently represent a hydrogen atom or an alkyl group having 1 to 4 carbon atoms. Any one of $R^{25}$ to $R^{28}$ represents a bond directly bonded to a nitrogen atom, and the others each independently represent a hydrogen atom or an alkyl group having 1 to 4 carbon atoms.

In the case where a Buchwald-Hartwig reaction is performed in the above synthesis scheme, X represents halogen or a triflate group. As the halogen, iodine, bromine, or chlorine is preferred. In this reaction, a palladium catalyst including a palladium complex or a palladium compound such as bis(dibenzylideneacetone)palladium(0) or allylpalladium(II) chloride dimer and a ligand that coordinates to the palladium complex or the palladium compound, such as tri(tert-butyl)phosphine, di-tert-butyl(1-methyl-2,2-diphenylcyclopropyl)phosphine, or tricyclohexylphosphine, can be used. Specific examples of the base include organic bases such as sodium tert-butoxide and inorganic bases such as potassium carbonate. In the case where a solvent is used, toluene, xylene, 1,3,5-trimethylbenzene, or the like can be used.

In the case where an Ullmann reaction is performed in the above synthesis scheme, X represents halogen. As the halogen, iodine, bromine, or chlorine is preferred. As a catalyst, copper or a copper compound can be used. Note that copper(I) iodide or copper(II) acetate is preferably used. Examples of the base to be used include an inorganic base such as potassium carbonate. As a solvent, 1,3-dimethyl-3,4,5,6-tetrahydro-2(1H)-pyrimidinone (DMPU), N-methyl-2-pyrrolidone (NMP), toluene, xylene, 1,3,5-trimethylbenzene, or the like is used. However, the solvent that can be used is not limited to these solvents. In the Ullmann reaction, the target substance can be obtained in a shorter time and in a higher yield when the reaction temperature is 100° C. or higher; therefore, it is preferable to use DMPU, NMP, or 1,3,5-trimethylbenzene each having a high boiling point. In addition, the reaction temperature is further preferably 150° C. or higher; therefore, DMPU is further preferably used.

Although an example of a method for synthesizing the organic compound of one embodiment of the present invention is described above, the present invention is not limited thereto and any other synthesis method may be employed.

The structures described in this embodiment can be used in appropriate combination with any of the structures described in the other embodiments.

Embodiment 2

In this embodiment, light-emitting devices including any of the organic compounds described in Embodiment 1 are described with reference to FIGS. 1A to 1E.

<<Basic Structure of Light-Emitting Device>>

Basic structures of the light-emitting device are described. FIG. 1A illustrates a light-emitting device including, between a pair of electrodes, an EL layer including a light-emitting layer. Specifically, an EL layer 103 is positioned between a first electrode 101 and a second electrode 102.

FIG. 1B illustrates a light-emitting device that has a stacked-layer structure (tandem structure) in which a plurality of EL layers (two EL layers 103a and 103b in FIG. 1B) are provided between a pair of electrodes and a charge-generation layer 106 is provided between the EL layers. A light-emitting device having a tandem structure enables fabrication of a light-emitting apparatus that can be driven at low voltage and has low power consumption.

The charge-generation layer 106 has a function of injecting electrons into one of the EL layers 103a and 103b and injecting holes into the other of the EL layers 103a and 103b when a potential difference is caused between the first electrode 101 and the second electrode 102. Thus, when voltage is applied in FIG. 1B such that the potential of the first electrode 101 is higher than that of the second electrode 102, the charge-generation layer 106 injects electrons into the EL layer 103a and injects holes into the EL layer 103b.

Note that in terms of light extraction efficiency, the charge-generation layer 106 preferably has a property of transmitting visible light (specifically, the charge-generation layer 106 preferably has a visible light transmittance of 40% or more). The charge-generation layer 106 functions even if it has lower conductivity than the first electrode 101 or the second electrode 102.

FIG. 1C illustrates a stacked-layer structure of the EL layer 103 in the light-emitting device of one embodiment of the present invention. In this case, the first electrode 101 is regarded as functioning as an anode and the second electrode 102 is regarded as functioning as a cathode. The EL layer 103 has a structure in which a hole-injection layer 111, a hole-transport layer 112, a light-emitting layer 113, an electron-transport layer 114, and an electron-injection layer 115 are stacked in this order over the first electrode 101. Note that the light-emitting layer 113 may have a stacked-layer structure of a plurality of light-emitting layers that emit light of different colors. For example, a light-emitting layer containing a light-emitting substance that emits red light, a light-emitting layer containing a light-emitting substance that emits green light, and a light-emitting layer containing a light-emitting substance that emits blue light may be stacked with or without a layer containing a carrier-transport material therebetween. Alternatively, a light-emitting layer containing a light-emitting substance that emits yellow light and a light-emitting layer containing a light-emitting substance that emits blue light may be used in combination. Note that the stacked-layer structure of the light-emitting layer 113 is not limited to the above. For example, the light-emitting layer 113 may have a stacked-layer structure of a plurality of light-emitting layers that emit light of the same color. For example, a first light-emitting layer containing a light-emitting substance that emits blue light and a second light-emitting layer containing a light-emitting substance that emits blue light may be stacked with or without a layer containing a carrier-transport material therebetween. The structure in which a plurality of light-emitting layers that emit light of the same color are stacked can sometimes achieve higher reliability than a single-layer structure. In the case where a plurality of EL layers are provided as in the tandem structure illustrated in FIG. 1B, the layers in each EL layer are sequentially stacked from the anode side as described above. When the first electrode 101 is the cathode and the second electrode 102 is the anode, the stacking order of the layers in the EL layer 103 is reversed. Specifically, the layer 111 over the first electrode 101 serving as the cathode is an electron-injection layer; the layer 112 is an electron-transport layer; the layer 113 is a light-emitting layer; the layer 114 is a hole-transport layer; and the layer 115 is a hole-injection layer.

The light-emitting layer 113 included in the EL layers (103, 103a, and 103b) contains an appropriate combination of a light-emitting substance and a plurality of substances, so that fluorescent or phosphorescent light of a desired emission color can be obtained. The light-emitting layer 113 may have a stacked-layer structure having different emission colors. In that case, light-emitting substances and other substances are different between the stacked light-emitting layers. Alternatively, the plurality of EL layers (103a and 103b) in FIG. 1B may exhibit their respective emission colors. Also in that case, the light-emitting substances and other substances are different between the stacked light-emitting layers.

The light-emitting device of one embodiment of the present invention can have a micro optical resonator (microcavity) structure when, for example, the first electrode 101 is a reflective electrode and the second electrode 102 is a transflective electrode in FIG. 1C. Thus, light from the light-emitting layer 113 in the EL layer 103 can be resonated between the electrodes and light obtained through the second electrode 102 can be intensified.

Note that when the first electrode 101 of the light-emitting device is a reflective electrode having a stacked structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is λ, the optical path length between the first electrode 101 and the second electrode 102 (the product of the thickness and the refractive index) is preferably adjusted to be mλ/2 (m is a natural number) or close to mλ/2.

To amplify desired light (wavelength: λ) obtained from the light-emitting layer 113, it is preferable to adjust each of the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) to be (2m'+1)λ/4 (m' is a natural number) or close to (2m'+1)λ/4. Here, the light-emitting region means a region where holes and electrons are recombined in the light-emitting layer 113.

By such optical adjustment, the spectrum of specific monochromatic light obtained from the light-emitting layer 113 can be narrowed and light emission with high color purity can be obtained.

In the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

The light-emitting device illustrated in FIG. 1D is a light-emitting device having a tandem structure. Owing to a microcavity structure of the light-emitting device, light (monochromatic light) with different wavelengths from the EL layers (103a and 103b) can be extracted. Thus, separate coloring for obtaining a plurality of emission colors (e.g., R, G, and B) is not necessary. Therefore, high definition can be easily achieved. A combination with coloring layers (color filters) is also possible. Furthermore, the emission intensity of light with a specific wavelength in the front direction can be increased, whereby power consumption can be reduced.

The light-emitting device illustrated in FIG. 1E is an example of the light-emitting device having the tandem structure illustrated in FIG. 1B, and includes three EL layers (103a, 103b, and 103c) stacked with charge-generation layers (106a and 106b) positioned therebetween, as illustrated in FIG. 1E. The three EL layers (103a, 103b, and 103c) include respective light-emitting layers (113a, 113b, and 113c), and the emission colors of the light-emitting layers can be selected freely. For example, each of the light-emitting layer 113a and the light-emitting layer 113c can emit blue light, and the light-emitting layer 113b can emit red light, green light, or yellow light. For another example, the light-emitting layer 113a can emit red light, the light-emitting layer 113b can emit blue light, green light, or yellow light, and the light-emitting layer 113c can emit red light.

In the light-emitting device of one embodiment of the present invention, at least one of the first electrode 101 and the second electrode 102 is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode, the transflective electrode has a visible light reflectance higher than or equal to 20% and lower than or equal to 80%, preferably higher than or equal to 40% and lower than or equal to 70%. These electrodes preferably have a resistivity of $1\times10^{-2}$ Ωcm or less.

When one of the first electrode 101 and the second electrode 102 is a reflective electrode in the light-emitting device of one embodiment of the present invention, the visible light reflectance of the reflective electrode is higher than or equal to 40% and lower than or equal to 100%, preferably higher than or equal to 70% and lower than or equal to 100%. This electrode preferably has a resistivity of $1\times10^{-2}$ Ωcm or less.

<<Specific Structure of Light-Emitting Device>>

Next, a specific structure of the light-emitting device of one embodiment of the present invention will be described. Here, the description is made using FIG. 1D showing the tandem structure. Note that the structure of the EL layer applies also to the structure of the light-emitting devices having a single structure in FIG. TA and FIG. 1C. When the light-emitting device in FIG. 1D has a microcavity structure, the first electrode 101 is formed as a reflective electrode and the second electrode 102 is formed as a transflective electrode. Thus, a single-layer structure or a stacked-layer structure can be formed using one or more kinds of desired electrode materials. Note that the second electrode 102 is formed after formation of the EL layer 103b, with the use of a material selected as described above.

<First Electrode and Second Electrode>

As materials for the first electrode 101 and the second electrode 102, any of the following materials can be used in an appropriate combination as long as the above functions of the electrodes can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, or an In—W—Zn oxide can be used. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table that is not described above (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

In the light-emitting device in FIG. 1D, when the first electrode 101 is the anode, a hole-injection layer 111a and a hole-transport layer 112a of the EL layer 103a are sequentially stacked over the first electrode 101 by a vacuum evaporation method. After the EL layer 103a and the charge-generation layer 106 are formed, a hole-injection layer 111b and a hole-transport layer 112b of the EL layer 103b are sequentially stacked over the charge-generation layer 106 in a similar manner.

<Hole-Injection Layer>

The hole-injection layers (111, 111a, and 111b) inject holes from the first electrode 101 serving as the anode or the charge-generation layers (106, 106a, and 106b) to the EL layers (103, 103a, and 103b) and contain an organic acceptor material or a material having a high hole-injection property.

The organic acceptor material allows holes to be generated in another organic compound whose HOMO level is close to the LUMO level of the organic acceptor material when charge separation is caused between the organic acceptor material and the organic compound. Thus, as the organic acceptor material, a compound having an electron-withdrawing group (e.g., a halogen group or a cyano group), such as a quinodimethane derivative, a chloranil derivative, and a hexaazatriphenylene derivative, can be used. Examples of the organic acceptor material include 7,7,8,8-tetracyano-2,3,5,6-tetrafluoroquinodimethane (abbreviation: $F_4$-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and 2-(7-dicyanomethylene-1,3,4,5,6,8,9,10-octafluoro-7H-pyren-2-ylidene)malononitrile. Note that among organic acceptor materials, a compound in which electron-withdrawing groups are bonded to fused aromatic rings each having a plurality of heteroatoms, such as HAT-CN, is particularly preferred because it has a high acceptor property and stable film quality against heat. Besides, a [3]radialene derivative having an electron-withdrawing group (particularly a cyano group or a halogen group such as a fluoro group), which has a very high electron-accepting property, is preferred; specific examples include α,α,α"-1,2,3-cyclopropanetriylidenetris[4-cyano-2,3,5,6-tetrafluorobenzeneacetonitrile], α,α,α"-1,2,3-cyclopropanetriylidenetris[2,6-dichloro-3,5-difluoro-4-(trifluoromethyl)benzeneacetonitrile], and α,α,α"-1,2,3-cyclopropanetriylidenetris[2,3,4,5,6-pentafluorobenzeneacetonitrile].

As the material having a high hole-injection property, an oxide of a metal belonging to Group 4 to Group 8 in the periodic table (e.g., a transition metal oxide such as molybdenum oxide, vanadium oxide, ruthenium oxide, tungsten oxide, or manganese oxide) can be used. Specific examples include molybdenum oxide, vanadium oxide, niobium oxide, tantalum oxide, chromium oxide, tungsten oxide, manganese oxide, and rhenium oxide. Among these oxides, molybdenum oxide is preferable because it is stable in the air, has a low hygroscopic property, and is easily handled. Other examples include phthalocyanine (abbreviation: $H_2Pc$) and a phthalocyanine-based compound such as copper phthalocyanine (abbreviation: CuPc).

Other examples include aromatic amine compounds, which are low molecular compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), N,N-bis{4-[bis(3-methylphenyl)amino]phenyl}-N,N-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Other examples include high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-V-phenylamino}phenyl)methacrylamide] (abbreviation: PTPDMA), and poly[N,N-bis(4-butylphenyl)-N,N-bis(phenyl)benzidine] (abbreviation: Poly-TPD). Alternatively, it is possible to use a high-molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), for example.

As the material having a high hole-injection property, a mixed material containing a hole-transport material and the above-described organic acceptor material (electron-accepting material) can be used. In that case, the organic acceptor material extracts electrons from the hole-transport material, so that holes are generated in the hole-injection layer 111 and the holes are injected into the light-emitting layer 113 through the hole-transport layer 112. Note that the hole-injection layer 111 may be formed to have a single-layer structure using a mixed material containing a hole-transport material and an organic acceptor material (electron-accepting material), or a stacked-layer structure of a layer containing a hole-transport material and a layer containing an organic acceptor material (electron-accepting material).

As the hole-transport material, the organic compound described in Embodiment 1 is preferably used. The hole-transport material preferably has a hole mobility higher than or equal to $1\times10^{-6}$ cm$^2$/Vs in the case where the square root of the electric field strength [V/cm] is 600. Note that any other substance can also be used as long as the substance has a hole-transport property higher than an electron-transport property.

As the hole-transport material, materials having a high hole-transport property, such as a compound having a π-electron rich heteroaromatic ring (e.g., a carbazole derivative, a furan derivative, or a thiophene derivative) and an aromatic amine (an organic compound having an aromatic amine skeleton), are preferable.

Examples of the carbazole derivative (an organic compound having a carbazole ring) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) include 3,3'-bis(9-phenyl-9H-carbazole) (abbreviation: PCCP), 9,9'-bis(biphenyl-4-yl)-3,3'-bi-9H-carbazole (abbreviation: BisBPCz), 9,9'-bis(1,1'-biphenyl-3-yl)-3,3'-bi-9H-carbazole (abbreviation: BismBPCz), 9-(1,1'-biphenyl-3-yl)-9'-(1,1'-biphenyl-4-yl)-9H,9'H-3,3'-bicarbazole (abbreviation: mBPCCBP), and 9-(2-naphthyl)-9'-phenyl-9H,9'H-3,3'-bicarbazole (abbreviation: PNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,V-bis(9-phenylcarbazol-3-yl)-N,V-diphenylbenzene-1,3-diamine (abbreviation: PCA2B), N,V,N'-triphenyl-N,N,N'-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenyl-carbazole (abbreviation: PCzPCA1), 3,6-bis[N-(9-phenyl-carbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N-bis[4-(carbazol-9-yl)phenyl]-N,NV-diphenyl-9,9-dimethylfluorene-2,7-diamine (abbreviation: YGA2F), and 4,4',4"-tris(carbazol-9-yl)triphenylamine (abbreviation: TCTA).

Other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the furan derivative (an organic compound having a furan ring) include 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Specific examples of the thiophene derivative (an organic compound having a thiophene ring) include organic compounds having a thiophene ring, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV).

Specific examples of the aromatic amine include 4,4'-bis[N-(1-naphthyl)-N-phenylamino]biphenyl (abbreviation: NPB or a-NPD), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4"-tris[N-(1-naphthyl)-N-phenylamino]triphenylamine (abbreviation: 1'-TNATA), 4,4',4"-tris(N,N-diphenylamino)triphenylamine (abbreviation: TDATA), 4,4',4"-tris[N-(3-methylphenyl)-N-phenylamino]triphenylamine (abbreviation: m-MTDATA), N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), DNTPD, 1,3,5-tris[N-(4-diphenylaminophenyl)-N-phenylamino]benzene (abbreviation: DPA3B), N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenyl-benzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf (6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yltriphenylamine (abbreviation: BBAPβNB-03), 4,4'-diphenyl-4"-(6;2'-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBiTBP-02), 4-[4'-(carbazol-9-yl)biphenyl-4-yl]-4'-(2-naphthyl)-4"-phenyltriphenylamine (abbreviation: YGTBij3NB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis([1,1'-biphenyl]--4-yl)-9,9'-spirobi[9H-fluoren]-2-amine (abbreviation: BBASF), N,N-bis([1,1'-biphenyl]-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi[9H-fluoren]-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-[4-(9-phenylfluoren-9-yl)phenyl]triphenylamine (abbreviation: BPAFLBi), N,N- bis(9,9-dimethyl-9H-fluoren-2-yl)-9,9'-spirobi-9H-fluoren-4-amine, N,N-bis(9,9-dimethyl-9H-fluoren-2-yl)-9,9'-spirobi-9H-fluoren-3-amine, N,N-bis(9,9-dimethyl-9H-fluoren-2-yl)-9,9'-spirobi-9H-fluoren-2-amine, and N,N-bis(9,9-dimethyl-9H-fluoren-2-yl)-9,9'-spirobi-9H-fluoren-1-amine.

Other examples of the hole-transport material include high-molecular compounds (e.g., oligomers, dendrimers, and polymers) such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide](abbreviation: PTPDMA), and poly[N,N-bis(4-butylphenyl)-N,N-bis(phenyl)benzidine](abbreviation: Poly-TPD). Alternatively, it is possible to use a high-molecular compound to which acid is added, such as poly(3,4-ethylenedioxythiophene)/poly(styrenesulfonic acid) (abbreviation: PEDOT/PSS) or polyaniline/poly(styrenesulfonic acid) (abbreviation: PAni/PSS), for example.

Note that the hole-transport material is not limited to the above examples, and any of a variety of known materials may be used alone or in combination as the hole-transport material.

The hole-injection layers (111, 111a, and 111b) can be formed by any of known film formation methods such as a vacuum evaporation method.

<Hole-Transport Layer>

The hole-transport layers (112, 112a, and 112b) transport the holes, which are injected from the first electrode 101 by the hole-injection layers (111, 111a, and 111b), to the light-emitting layers (113, 113b, and 113b). Note that the hole-transport layers (112, 112a, and 112b) contain a hole-transport material. Thus, the hole-transport layers (112, 112a, and 112b) can be formed using a hole-transport material that can be used for the hole-injection layers (111, 111a, and 111b).

Note that in the light-emitting device described in this embodiment, the organic compound used for the hole-transport layers (112, 112a, and 112b) can also be used for the light-emitting layers (113, 113b, and 113b). The use of the same organic compound for the hole-transport layers (112, 112a, and 112b) and the light-emitting layers (113, 113b, and 113b) is preferable, in which case holes can be efficiently transported from the hole-transport layers (112, 112a, and 112b) to the light-emitting layers (113, 113b, and 113b).

<Light-Emitting Layer>

The light-emitting layers (113, 113b, and 113b) contain a light-emitting substance. Note that as a light-emitting substance that can be used in the light-emitting layers (113, 113b, and 113b), a substance whose emission color is blue, violet, bluish violet, green, yellowish green, yellow, orange, red, or the like can be used as appropriate. When a plurality of light-emitting layers are provided, the use of different light-emitting substances for the light-emitting layers enables a structure that exhibits different emission colors (e.g., white light emission obtained by a combination of complementary emission colors). Furthermore, one light-emitting layer may have a stacked-layer structure of layers containing different light-emitting substances.

The light-emitting layers (113, 113b, and 113b) may each contain one or more kinds of organic compounds (e.g., a host material) in addition to a light-emitting substance (guest material).

In the case where a plurality of host materials are used in the light-emitting layers (113, 113b, and 113b), a second host material that is additionally used is preferably a substance having a larger energy gap than a known guest material and a first host material. Preferably, the lowest singlet excitation energy level (Si level) of the second host material is higher than that of the first host material, and the lowest triplet excitation energy level (T1 level) of the second host material is higher than that of the guest material. Preferably, the lowest triplet excitation energy level (T1 level) of the second host material is higher than that of the first host material. With such a structure, an exciplex can be formed by the two kinds of host materials. To form an exciplex efficiently, it is particularly preferable to combine a compound that easily accepts holes (hole-transport material) and a compound that easily accepts electrons (electron-transport material). With the above structure, high efficiency, low voltage, and a long lifetime can be achieved at the same time.

As an organic compound used as the host material (including the first host material and the second host material), organic compounds such as the hole-transport materials usable in the hole-transport layers (112, 112a, and 112b) and electron-transport materials usable in electron-transport layers (114, 114a, and 114b) described later can be used as long as they satisfy requirements for the host material used in the light-emitting layer. Another example is an exciplex formed by two or more kinds of organic compounds (the first host material and the second host material). An exciplex whose excited state is formed by two or more kinds of organic compounds has an extremely small difference between the S1 level and the T1 level and functions as a TADF material capable of converting triplet excitation energy into singlet excitation energy. In an example of a preferred combination of two or more kinds of organic compounds forming an exciplex, one of the two or more kinds of organic compounds has a π-electron deficient heteroaromatic ring and the other has a π-electron rich heteroaromatic ring. A phosphorescent substance such as an iridium-, rhodium-, or platinum-based organometallic complex or a metal complex may be used as one component of the combination for forming an exciplex.

There is no particular limitation on the light-emitting substances that can be used for the light-emitting layers (113, 113b, and 113b), and a light-emitting substance that converts singlet excitation energy into light in the visible light range or a light-emitting substance that converts triplet excitation energy into light in the visible light range can be used.

<<Light-emitting substance that converts singlet excitation energy into light>>

The following substances that exhibit fluorescent light (fluorescent substances) can be given as examples of the light-emitting substance that converts singlet excitation energy into light and can be used in the light-emitting layer 113: a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of pyrene derivatives include N,N-bis(3-methylphenyl)-N,N-bis[3-(9-phenyl-9H-fluoren-9-yl)phenyl]pyrene-1,6-diamine (abbreviation: 1,6mMemFLPAPm), (N,V-diphenyl-N,N-bis[4-(9-phenyl-9H-fluoren-9-yl)phenyl]pyrene-1,6-diamine) (abbreviation: 1,6FLPAPrn), N,V-bis(dibenzofuran-2-yl)-N,V-diphenylpyrene-1,6-diamine (abbreviation: 1,6FrAPm), N,V-bis(dibenzothiophen-2-yl)-N,V-diphenylpyrene-1,6-diamine (abbreviation: 1,6ThAPm), N,N-(pyrene-1,6-diyl)bis

[(N-phenylbenzo[b]naphtho[1,2-d]furan)-6-amine] (abbreviation: 1,6BnfAPm), N,V-(pyrene-1,6-diyl)bis[(N-phenylbenzo[b]naphtho[1,2-d]furan)-8-amine] (abbreviation: 1,6BnfAPrn-02), and N,V-(pyrene-1,6-diyl)bis[(6,N-diphenylbenzo[b]naphtho[1,2-d]furan)-8-amine] (abbreviation: 1,6BnfAPm-03).

In addition, it is possible to use, for example, 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,V,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), and N-[4-(9,10-diphenyl-2-anthryl)phenyl]-N,N,V-triphenyl-1,4-phenylenediamine (abbreviation: 2DPAPPA).

It is also possible to use, for example, N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N'-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N,N-tetrakis(4-methylphenyl)tetracene-5,11-diamine (abbreviation: p-mPhTD), 7,14-diphenyl-N,N,V,V-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), 1,6BnfAPm-03,3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). In particular, pyrenediamine compounds such as 1,6FLPAPm, 1,6mMemFLPAPm, and 1,6BnfAPm-03 can be used, for example.

<<Light-Emitting Substance that Converts Triplet Excitation Energy into Light>>

Examples of the light-emitting substance that converts triplet excitation energy into light and can be used in the light-emitting layer 113 include substances that emit phosphorescent light (phosphorescent substances) and thermally activated delayed fluorescent (TADF) materials that exhibit thermally activated delayed fluorescence.

A phosphorescent substance is a compound that exhibits phosphorescent light but does not exhibit fluorescent light at a temperature higher than or equal to a low temperature (e.g., 77 K) and lower than or equal to room temperature (i.e., higher than or equal to 77 K and lower than or equal to 313 K). The phosphorescent substance preferably contains a metal element with large spin-orbit interaction, and can be an organometallic complex, a metal complex (platinum complex), or a rare earth metal complex, for example. Specifically, the phosphorescent substance preferably contains a transition metal element. It is particularly preferable that the phosphorescent substance contain a platinum group element (ruthenium (Ru), rhodium (Rh), palladium (Pd), osmium (Os), iridium (Ir), or platinum (Pt)), especially iridium, in which case the probability of direct transition between the singlet ground state and the triplet excited state can be increased.

<<Phosphorescent Substance (from 450 nm to 570 nm, Blue or Green)>>

As examples of a phosphorescent substance which emits blue or green light and whose emission spectrum has a peak wavelength of greater than or equal to 450 nm and less than or equal to 570 nm, the following substances can be given.

Examples include organometallic complexes having a 4H-triazole ring, such as tris{ 2-[5-(2-methylphenyl)-4-(2,6-dimethylphenyl)-4H-1,2,4-triazol-3-yl-κN$^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole ring, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-TH-1,2,4-triazolato)iridium(III) (abbreviation: [Ir(Prptzl-Me)$_3$]); organometallic complexes having an imidazole ring, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic complexes in which a phenylpyridine derivative having an electron-withdrawing group is a ligand, such as bis[2-(4',6'-difluorophenyl)pyridinato-N,C$^2$]iridium(III) tetrakis(1-pyrazolyl)borate (abbreviation: FIr6), bis[2-(4',6'-difluorophenyl)pyridinato-N,C$^2$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)).

<<Phosphorescent Substance (from 495 nm to 590 nm, Green or Yellow)>>

As examples of a phosphorescent substance which emits green or yellow light and whose emission spectrum has a peak wavelength of greater than or equal to 495 nm and less than or equal to 590 nm, the following substances can be given.

Examples include organometallic iridium complexes having a pyrimidine ring, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κN$^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine ring, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine ring, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), bis(2-phenylquinolinato-N,C$^{2'}$)iridium(III) acetylacetonate (abbreviation: [Ir(pq)$_2$(acac)]), bis[2-(2-pyridinyl-N)phenyl-κC][2-(4-phenyl-2-pyridinyl-κN)phenyl-κC]iridium(III) (abbreviation: [Ir(ppy)$_2$(4dppy)]), bis[2-(2-pyridinyl-N)phenyl-κC][2-(4-methyl-5-phenyl-2-pyridinyl-K)phenyl-κC], [2-d$_3$-methyl-8-(2-pyridinyl-κN)benzofuro[2,3-b]pyridine-κC]bis[2-(5-d$_3$-methyl-2-pyridinyl-κN2)phenyl-κC]iridium(III) (abbreviation: Ir(5mppy-d$_3$)$_2$(mbfpypy-d$_3$)), [2-(methyl-d$_3$)-8-[4-(1-methylethyl-1-d)-2-pyridinyl-κN]benzofuro[2,3-b]pyridin-7-yl-κC]bis[5-(methyl-d$_3$)-2-[5-(methyl-d$_3$)-2-pyridinyl-κN]phenyl-κC]iridium(III) (abbreviation: Ir(5mtpy-d$_6$)$_2$(mbfpypy-iPr-d$_4$)), [2-d$_3$-methyl-(2-pyridinyl-κN)benzofuro[2,3-b]pyridine-κC]bis[2-(2-pyridinyl-N)phenyl-κC]iridium(III) (abbreviation: Ir(ppy)$_2$(mbfpypy-d$_3$)), and [2-(4-methyl-5-phenyl-2-pyridinyl-κN)phenyl-κC]bis[2-(2-pyridinyl-N)phenyl-κC]iridium(III) (abbreviation: Ir(ppy)$_2$(mdppy)); organometallic complexes such as bis(2,4-diphenyl-1,3-oxazolato-N,C$^2$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^2$)iridium(III) acetylacetonate (abbreviation: [Ir(bt)$_2$(acac)]); and a rare earth metal complex such as tris(acetylacetonato)(monophenanthroline)terbium(III) (abbreviation: [Tb(acac)$_3$(Phen)]).

<<Phosphorescent Substance (from 570 nm to 750 nm, Yellow or Red)>>

As examples of a phosphorescent substance which emits yellow or red light and whose emission spectrum has a peak wavelength of greater than or equal to 570 nm and less than or equal to 750 nm, the following substances can be given.

Examples include organometallic complexes having a pyrimidine ring, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(dlnpm)$_2$(dpm)]); organometallic complexes having a pyrazine ring, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium (III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$o,o')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$o,o')iridium(III) (abbreviation: [Ir(dmdppr-dmCP)$_2$(dpm)]), bis[2-(5-(2,6-dimethylphenyl)-3-(3,5-dimethylphenyl)-2-pyrazinyl-κN)–4,6-dimethylphenyl-κC](2,2',6,6'-tetramethyl-3,5-heptanedionato-κ$^2$o,o')iridium (III) (abbreviation: [Ir(dmdppr-dmp)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine ring, such as tris(1-phenylisoquinolinato-N,C$^{2'}$) iridium(III) (abbreviation: [Ir(piq)$_3$]), bis(1-phenylisoquinolinato-N,C$^{2'}$)iridium(III) acetylacetonate (abbreviation: [Ir(piq)$_2$(acac)]), and bis[4,6-dimethyl-2-(2-quinolinyl-κN)phenyl-κC](2,4-pentanedionato-κ$^2$o,o')iridium(III) (abbreviation: [Ir(dmpqn)$_2$(acac)]); a platinum complex such as 2,3,7,8,12,13,17,18-octaethyl-21H,23H-porphyrin platinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]).

<<TADF Material>>

Any of materials described below can be used as the TADF material. The TADF material is a material that has a small difference between its S1 and T1 levels (preferably less than or equal to 0.2 eV), enables up-conversion of a triplet excited state into a singlet excited state (i.e., reverse intersystem crossing) using a little thermal energy, and efficiently exhibits light (fluorescent light) from the singlet excited state. The thermally activated delayed fluorescence is efficiently obtained under the condition where the difference in energy between the triplet excited energy level and the singlet excited energy level is greater than or equal to 0 eV and less than or equal to 0.2 eV, preferably greater than or equal to 0 eV and less than or equal to 0.1 eV. Note that delayed fluorescence by the TADF material refers to light emission having a spectrum similar to that of normal fluorescence and an extremely long lifetime. The lifetime is longer than or equal to $1\times10^{-6}$ seconds, preferably longer than or equal to $1\times10^{-3}$ seconds.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), and an octaethylporphyrin-platinum chloride complex (abbreviation: PtCl$_2$OEP).

[Chemical Formulae 16]

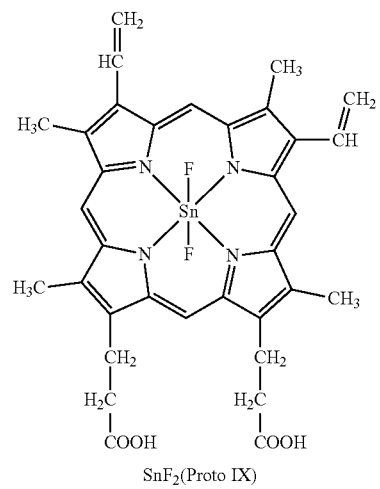

SnF$_2$(Proto IX)

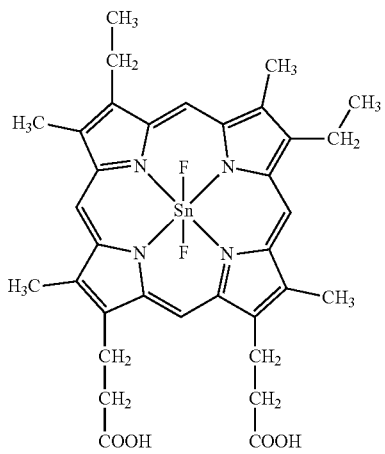

SnF$_2$(Meso IX)

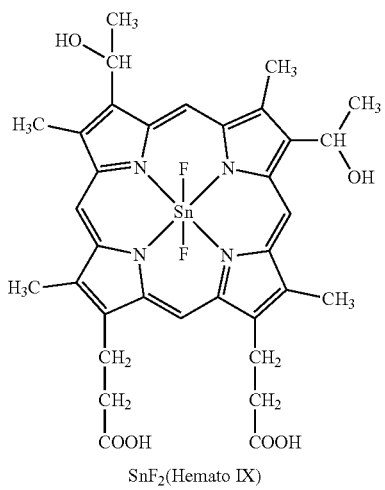

SnF$_2$(Hemato IX)

-continued

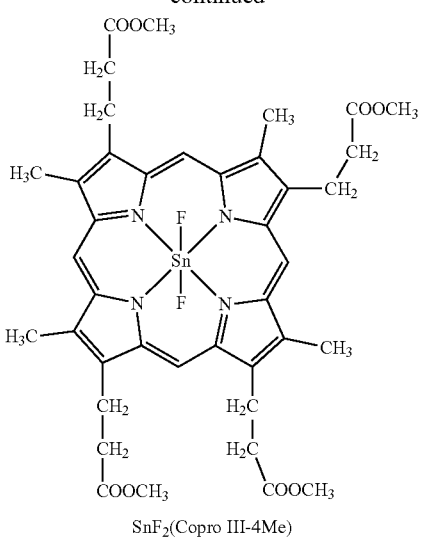

SnF$_2$(Copro III-4Me)

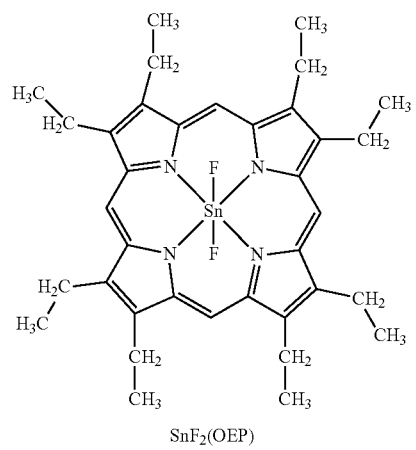

SnF$_2$(OEP)

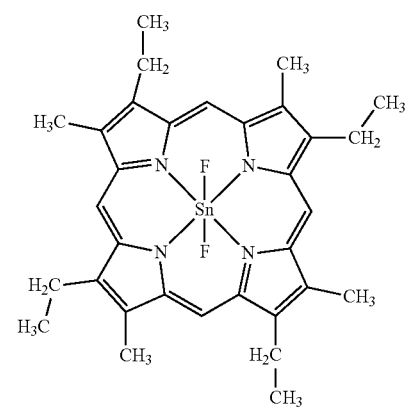

SnF$_2$(Etio 1)

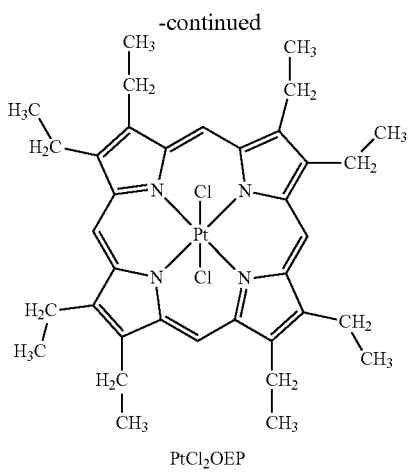

PtCl₂OEP

Alternatively, a heteroaromatic compound having a π-electron rich heteroaromatic compound and a π-electron deficient heteroaromatic compound, such as 2-(biphenyl-4-yl)-4,6-bis(12-phenylindolo[2,3-α]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), or 9-[3-(4,6-diphenyl-1,3,5-triazin-2-yl)phenyl]-9'-phenyl-2,3'-bi-9H-carbazole (abbreviation: mPCCzPTzn-02) may be used.

Note that a substance in which a π-electron rich heteroaromatic compound is directly bonded to a π-electron deficient heteroaromatic compound is particularly preferable because both the donor property of the π-electron rich heteroaromatic compound and the acceptor property of the π-electron deficient heteroaromatic compound are improved and the energy difference between the singlet excited state and the triplet excited state becomes small. As the TADF material, a TADF material in which the singlet and triplet excited states are in thermal equilibrium (TADF100) may be used. Since such a TADF material enables a short emission lifetime (excitation lifetime), an efficiency decrease of a light-emitting element in a high-luminance region can be inhibited.

[Chemical Formulae 17]

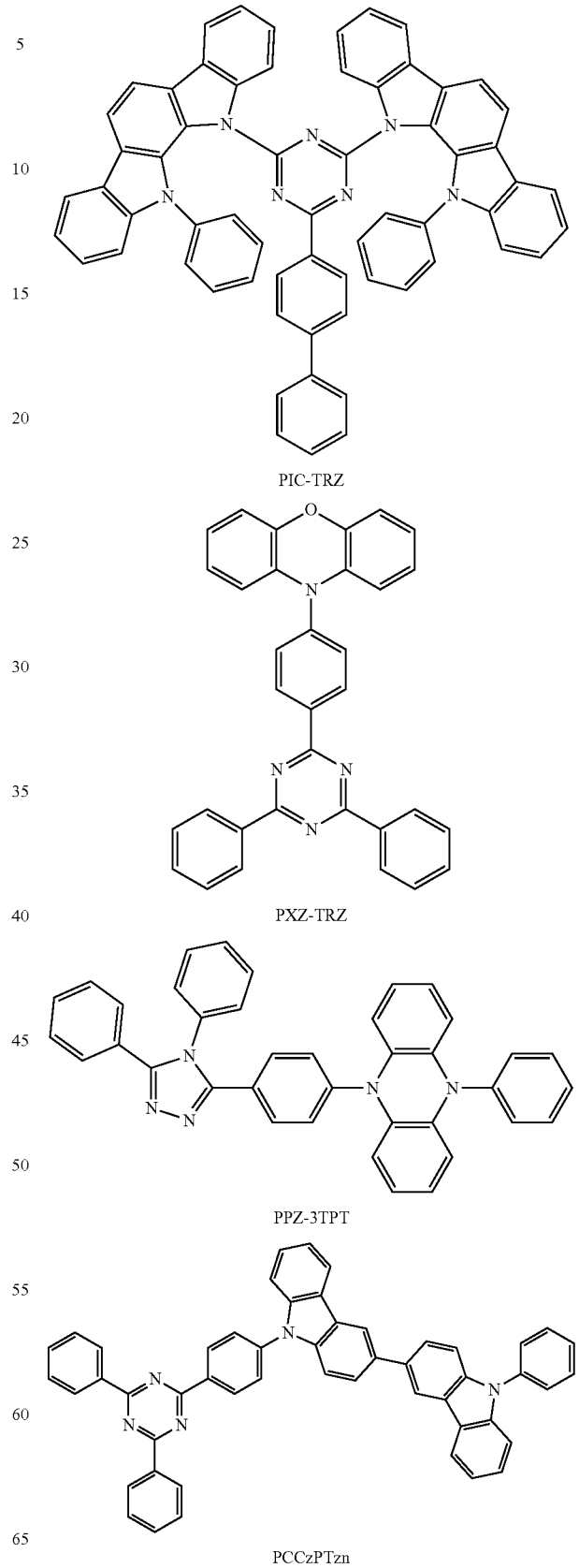

PIC-TRZ

PXZ-TRZ

PPZ-3TPT

PCCzPTzn

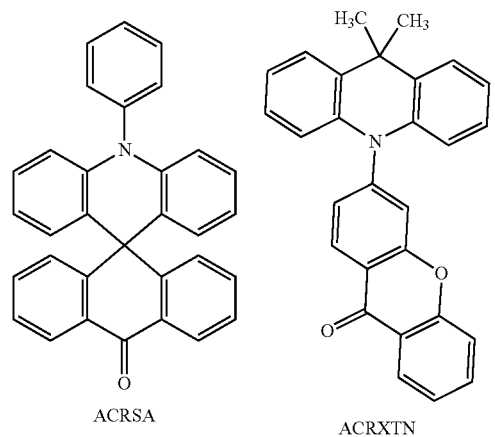

ACRSA

ACRXTN

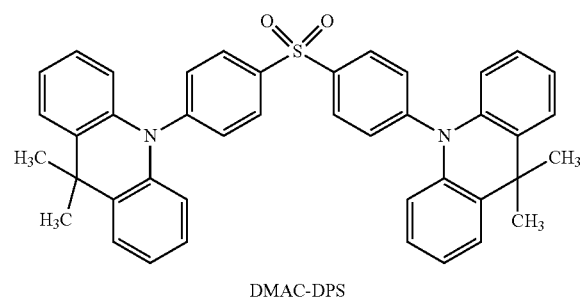

DMAC-DPS

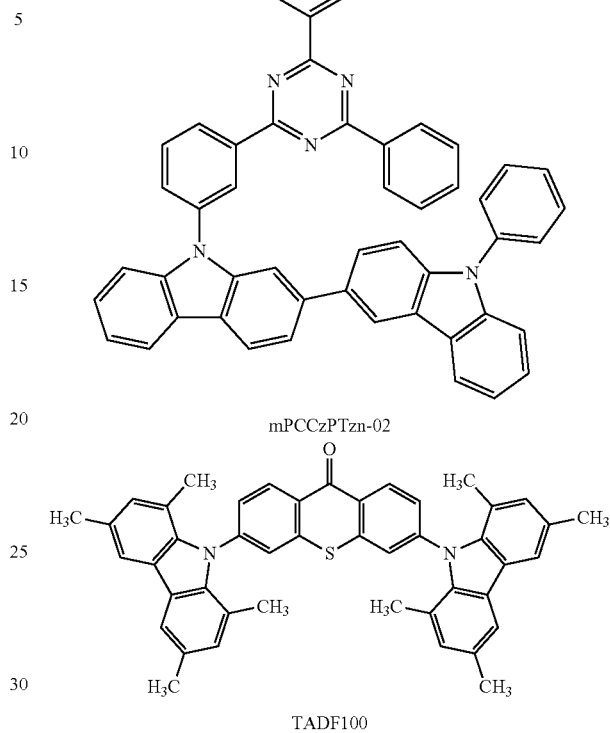

mPCCzPTzn-02

TADF100

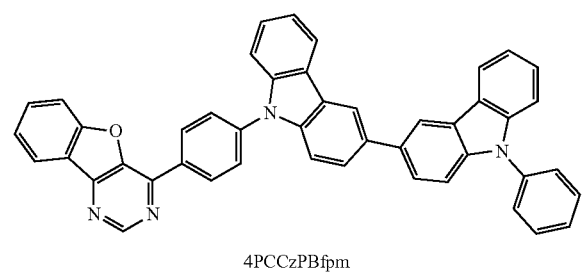

4PCCzPBfpm

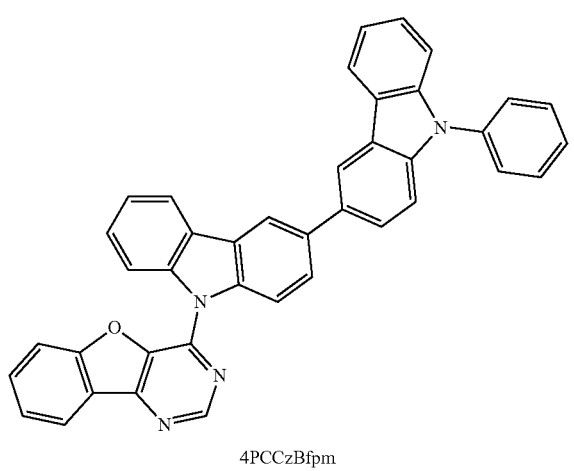

4PCCzBfpm

In addition to the above, another example of a material having a function of converting triplet excitation energy into light is a nano-structure of a transition metal compound having a perovskite structure. In particular, a nano-structure of a metal halide perovskite material is preferable. The nano-structure is preferably a nanoparticle or a nanorod.

As the organic compound (e.g., the host material) used in combination with the above-described light-emitting substance (guest material) in the light-emitting layers (113, 113b, 113b, and 113c), one or more kinds selected from substances having a larger energy gap than the light-emitting substance (guest material) are used.

<<Host Material for Fluorescence>>

In the case where the light-emitting substance used in the light-emitting layers (113, 113b, 113b, and 113c) is a fluorescent substance, an organic compound (a host material) used in combination with the fluorescent substance is preferably an organic compound that has a high energy level in a singlet excited state and has a low energy level in a triplet excited state, or an organic compound having a high fluorescence quantum yield. Therefore, the hole-transport material (described above) and the electron-transport material (described below) described in this embodiment, for example, can be used as long as they are organic compounds that satisfy such a condition.

In terms of a preferred combination with the light-emitting substance (fluorescent substance), examples of the organic compound (host material), some of which overlap the above specific examples, include fused polycyclic aromatic compounds such as an anthracene derivative, a tetracene derivative, a phenanthrene derivative, a pyrene derivative, a chrysene derivative, and a dibenzo[g,p] chrysene derivative.

Specific examples of the organic compound (host material) that is preferably used in combination with the fluorescent substance include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N,N,N',N',N'',N''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9-(1-naphthyl)-10-(2-naphthyl)anthracene (abbreviation: α,βADN), 2-(10-phenylanthracen-9-yl)dibenzofuran, 2-(10-phenyl-9-anthracenyl)-benzo[b]naphtho[2,3-d]furan (abbreviation: Bnf(II)PhA), 9-(1-naphthyl)-10-[4-(2-naphthyl)phenyl]anthracene (abbreviation: αN-βNPAnth), 9-(2-naphthyl)-10-[3-(2-naphthyl)phenyl]anthracene (abbreviation: βN-mβNPAnth), 1-[4-(10-[1,1'-biphenyl]-4-yl-9-anthracenyl)phenyl]-2-ethyl-TH-benzimidazole (abbreviation: EtBImPBPhA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

<<Host Material for Phosphorescence>>

In the case where the light-emitting substance used in the light-emitting layers (113, 113b, 113b, and 113c) is a phosphorescent substance, an organic compound having triplet excitation energy (an energy difference between a ground state and a triplet excited state) which is higher than that of the light-emitting substance is preferably selected as the organic compound (host material) used in combination with the phosphorescent substance. Note that when a plurality of organic compounds (e.g., a first host material and a second host material (or an assist material)) are used in combination with a light-emitting substance so that an exciplex is formed, the plurality of organic compounds are preferably mixed with the phosphorescent substance.

With such a structure, light emission can be efficiently obtained by exciplex-triplet energy transfer (ExTET), which is energy transfer from an exciplex to a light-emitting substance. Note that a combination of the plurality of organic compounds that easily forms an exciplex is preferably employed, and it is particularly preferable to combine a compound that easily accepts holes (hole-transport material) and a compound that easily accepts electrons (electron-transport material).

In terms of a preferred combination with the light-emitting substance (phosphorescent substance), examples of the organic compounds (the host material and the assist material), some of which overlap the above specific examples, include an aromatic amine (an organic compound having an aromatic amine skeleton), a carbazole derivative (an organic compound having a carbazole ring), a dibenzothiophene derivative (an organic compound having a dibenzothiophene ring), a dibenzofuran derivative (an organic compound having a dibenzofuran ring), an oxadiazole derivative (an organic compound having an oxadiazole ring), a triazole derivative (an organic compound having a triazole ring), a benzimidazole derivative (an organic compound having a benzimidazole ring), a quinoxaline derivative (an organic compound having a quinoxaline ring), a dibenzoquinoxaline derivative (an organic compound having a dibenzoquinoxaline ring), a pyrimidine derivative (an organic compound having a pyrimidine ring), a triazine derivative (an organic compound having a triazine ring), a pyridine derivative (an organic compound having a pyridine ring), a bipyridine derivative (an organic compound having a bipyridine ring), a phenanthroline derivative (an organic compound having a phenanthroline ring), a furodiazine derivative (an organic compound having a furodiazine ring), and zinc- and aluminum-based metal complexes.

Among the above organic compounds, specific examples of the aromatic amine and the carbazole derivative, which are organic compounds having a high hole-transport property, are the same as the specific examples of the hole-transport materials described above, and those materials are preferable as the host material.

Among the above organic compounds, specific examples of the dibenzothiophene derivative and the dibenzofuran derivative, which are organic compounds having a high hole-transport property, include 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), DBT3P-II, 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II). Such derivatives are preferable as the host material.

Other examples of preferred host materials include metal complexes having an oxazole-based or thiazole-based ligand, such as bis[2-(2-benzoxazolyl)phenolato]zinc(II) (abbreviation: ZnPBO) and bis[2-(2-benzothiazolyl)phenolato]zinc(II) (abbreviation: ZnBTZ).

Among the above organic compounds, specific examples of the oxadiazole derivative, the triazole derivative, the benzimidazole derivative, the quinoxaline derivative, the dibenzoquinoxaline derivative, the quinazoline derivative, and the phenanthroline derivative, which are organic compounds having a high electron-transport property, include an organic compound including a heteroaromatic ring having a polyazole ring, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), or 4,4'-bis(5-methylbenzoxazol-2-yl)stilbene (abbreviation: BzOs), an organic compound including a heteroaromatic ring having a pyridine ring, such as bathophenanthroline (abbreviation: BPhen), bathocuproine (abbreviation: BCP), 2,9-bis(naphthalen-2-yl)-4,7-diphenyl-1, 10-phenanthroline (abbreviation: NBPhen), or 2,2-(1,3-phenylene)bis[9-phenyl-1,10-phenanthroline](abbreviation: mPPhen2P), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-{4-[9,10-di(2-naphthyl)-2-anthryl]phenyl}-1-phenyl-1H-benzimidazole (abbreviation: ZADN), and 2-[4'-(9-phenyl-9H-carbazol-3-yl)-3,1'-biphenyl-1-yl]dibenzo[f,h]quinoxaline (abbreviation: 2mpPCBPDBq). Such organic compounds are preferable as the host material.

Among the above organic compounds, specific examples of the pyridine derivative, the diazine derivative (including the pyrimidine derivative, the pyrazine derivative, and the pyridazine derivative), the triazine derivative, and the furodiazine derivative, which are organic compounds having a high electron-transport property, include organic compounds including a heteroaromatic ring having a diazine ring, such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), 9,9'-[pyrimidine-4,6-diylbis(biphenyl-3,3'-diyl)]bis(9H-carbazole) (abbreviation: 4,6mCzBP2Pm), 2-[3'-(9,9-dimethyl-9H-fluoren-2-yl)-1,1'-biphenyl-3-yl]-4,6-diphenyl-1,3,5-triazine (abbreviation: mFBPTzn), 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm), 9-[3'-(dibenzothiophen-4-yl)biphenyl-3-yl]naphtho[1',2':4,5]furo[2,3-b]pyrazine (abbreviation: 9mDBtBPNfpr), 9-[(3'-dibenzothiophen-4-yl)biphenyl-4-yl]naphtho[1',2':4,5]furo[2,3-b]pyrazine (abbreviation: 9pmDBtBPNfpr), 5-[3-(4,6-diphenyl-1,3,5-triazin-2-yl)phenyl]-7,7-dimethyl-5H,7H-indeno[2,1-b]carbazole (abbreviation: mINc(II)PTzn), 2-[3'-(triphenylen-2-yl)-1,1'-biphenyl-3-yl]-4,6-diphenyl-1,3,5-triazine (abbreviation: mTpBPTzn), 2-[(1,1'-biphenyl)-4-yl]-4-phenyl-6-[9,9'-spirobi(9H-fluoren)–2-yl]-1,3,5-triazine (abbreviation: BP-SFTzn), 2,6-bis(4-naphthalen-1-ylphenyl)-4-[4-(3-pyridyl)phenyl]pyrimidine (abbreviation: 2,4NP-6PyPPm), 9-[4-(4,6-diphenyl-1,3,5-triazin-2-yl)-2-dibenzothiophenyl]-2-phenyl-9H-carbazole (abbreviation: PCDBfTzn), 2-[1,1'-biphenyl]-3-yl-4-phenyl-6-(8-[1,1':4',1"-terphenyl]-4-yl-1-dibenzofuranyl)-1,3,5-triazine (abbreviation: mBP-TPDBfTzn), 6-(1,1'-biphenyl-3-yl)-4-[3,5-bis(9H-carbazol-9-yl)phenyl]-2-phenylpyrimidine (abbreviation: 6mBP-4Cz2PPm), and 4-[3,5-bis(9H-carbazol-9-yl)phenyl]-2-phenyl-6-(1,1'-biphenyl-4-yl)pyrimidine (abbreviation: 6BP-4Cz2PPm). Such organic compounds are preferable as the host material.

Among the above organic compounds, specific examples of metal complexes that are organic compounds having a high electron-transport property include zinc- and aluminum-based metal complexes, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq), and metal complexes having a quinoline ring or a benzoquinoline ring. Such metal complexes are preferable as the host material.

Moreover, high molecular compounds such as poly(2,5-pyridinediyl) (abbreviation: PPy), poly[(9,9-dihexylfluorene-2,7-diyl)-co-(pyridine-3,5-diyl)](abbreviation: PF-Py), and poly[(9,9-dioctylfluorene-2,7-diyl)-co-(2,2'-bipyridine-6,6'-diyl)] (abbreviation: PF-BPy) are preferable as the host material.

Examples of organic compounds having bipolar properties, a high hole-transport property and a high electron-transport property, which can be used as the host material, include organic compounds having a diazine ring, such as 9-phenyl-9'-(4-phenyl-2-quinazolinyl)-3,3'-bi-9H-carbazole (abbreviation: PCCzQz), 2-[4'-(9-phenyl-9H-carbazol-3-yl)-3,1'-biphenyl-1-yl]dibenzo[f,h]quinoxaline (abbreviation: 2mpPCBPDBq), 5-[3-(4,6-diphenyl-1,3,5-triazin-2-yl)phenyl]-7,7-dimethyl-5H,7H-indeno[2,1-b]carbazole (abbreviation: mINc(II)PTzn), 11-(4-[1,1'-biphenyl]-4-yl-6-phenyl-1,3,5-triazin-2-yl)-11,12-dihydro-12-phenyl-indolo[2,3-α]carbazole (abbreviation: BP-Icz(II)Tzn), and 7-[4-(9-phenyl-9H-carbazol-2-yl)quinazolin-2-yl]-7H-dibenzo[c,g]carbazole (abbreviation: PC-cgDBCzQz).

<Electron-Transport Layer>

The electron-transport layers (114, 114a, and 114b) transport the electrons, which are injected from the second electrode 102 or the charge-generation layers (106, 106a, and 106b) by electron-injection layers (115, 115a, and 115b) described later, to the light-emitting layers (113, 113b, 113b, and 113c). It is preferable that the electron-transport material used in the electron-transport layers (114, 114a, and 114b) be a substance having an electron mobility higher than or equal to $1 \times 10^{-6}$ cm$^2$/Vs in the case where the square root of the electric field strength [V/cm] is 600. Note that any other substance can also be used as long as the substance has an electron-transport property higher than a hole-transport property. The electron-transport layers (114, 114a, and 114b) can function even with a single-layer structure and may have a stacked-layer structure including two or more layers. A photolithography process performed over the electron-transport layer including the above-described mixed material, which has heat resistance, can inhibit an adverse effect of the thermal process on the device characteristics.

<<Electron-Transport Material>>

As the electron-transport material that can be used for the electron-transport layers (114, 114a, and 114b), an organic compound having a high electron-transport property can be used, and for example, a heteroaromatic compound can be used. The heteroaromatic compound refers to a cyclic compound including at least two different kinds of elements in a ring. Examples of cyclic structures include a three-membered ring, a four-membered ring, a five-membered ring, and a six-membered ring, among which a five-membered ring and a six-membered ring are particularly preferred. The elements included in the heteroaromatic compound are preferably one or more of nitrogen, oxygen, and sulfur, in addition to carbon. In particular, a heteroaromatic compound containing nitrogen (a nitrogen-containing heteroaromatic compound) is preferred, and any of materials having a high electron-transport property (electron-transport materials), such as a nitrogen-containing heteroaromatic compound and a π-electron deficient heteroaromatic compound including the nitrogen-containing heteroaromatic compound, is preferably used.

The heteroaromatic compound is an organic compound including at least one heteroaromatic ring.

The heteroaromatic ring includes any one of a pyridine ring, a diazine ring, a triazine ring, a polyazole ring, an oxazole ring, a thiazole ring, and the like. A heteroaromatic ring having a diazine ring includes a heteroaromatic ring having a pyrimidine ring, a pyrazine ring, a pyridazine ring, or the like. A heteroaromatic ring having a polyazole ring includes a heteroaromatic ring having an imidazole ring, a triazole ring, or an oxadiazole ring.

The heteroaromatic ring includes a fused heteroaromatic ring having a fused ring structure. Examples of the fused heteroaromatic ring include a quinoline ring, a benzoquinoline ring, a quinoxaline ring, a dibenzoquinoxaline ring, a quinazoline ring, a benzoquinazoline ring, a dibenzoquinazoline ring, a phenanthroline ring, a furodiazine ring, and a benzimidazole ring.

Examples of the heteroaromatic compound having a five-membered ring structure, which is a heteroaromatic compound including carbon and one or more of nitrogen, oxygen, sulfur, and the like, include a heteroaromatic compound having an imidazole ring, a heteroaromatic compound having a triazole ring, a heteroaromatic compound having an oxazole ring, a heteroaromatic compound having an oxadiazole ring, a heteroaromatic compound having a thiazole ring, and a heteroaromatic compound having a benzimidazole ring.

Examples of the heteroaromatic compound having a six-membered ring structure, which is a heteroaromatic compound including carbon and one or more of nitrogen, oxygen, sulfur, and the like, include a heteroaromatic compound having a heteroaromatic ring, such as a pyridine ring, a diazine ring (including a pyrimidine ring, a pyrazine ring, a pyridazine ring, or the like), a triazine ring, or a polyazole ring. Other examples include a heteroaromatic compound having a bipyridine structure and a heteroaromatic compound having a terpyridine structure, although they are included in examples of a heteroaromatic compound in which pyridine rings are connected.

Examples of the heteroaromatic compound having a fused ring structure including the above six-membered ring structure as a part include a heteroaromatic compound having a fused heteroaromatic ring such as a quinoline ring, a benzoquinoline ring, a quinoxaline ring, a dibenzoquinoxaline ring, a phenanthroline ring, a furodiazine ring (including a structure in which an aromatic ring is fused to a furan ring of a furodiazine ring), or a benzimidazole ring.

Specific examples of the above-described heteroaromatic compound having a five-membered ring structure (a polyazole ring (including an imidazole ring, a triazole ring, or an oxadiazole ring), an oxazole ring, a thiazole ring, or a benzimidazole ring) include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), and 4,4'-bis(5-methylbenzoxazol-2-yl)stilbene (abbreviation: BzOs).

Specific examples of the above-described heteroaromatic compound having a six-membered ring structure (including a heteroaromatic ring having a pyridine ring, a diazine ring, a triazine ring, or the like) include a heteroaromatic compound including a heteroaromatic ring having a pyridine ring, such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB), a heteroaromatic compound including a heteroaromatic ring having a triazine ring, such as 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 5-[3-(4,6-diphenyl-1,3,5-triazin-2-yl)phenyl]-7,7-dimethyl-5H,7H-indeno[2,1-b]carbazole (abbreviation: mINc(II)PTzn), 2-[3'-(triphenylen-2-yl)-1,1'-biphenyl-3-yl]-4,6-diphenyl-1,3,5-triazine (abbreviation: mTpBPTzn), 2-[(1,1'-biphenyl)-4-yl]-4-phenyl-6-[9,9'-spirobi(9H-fluoren)–2-yl]-1,3,5-triazine (abbreviation: BP-SFTzn), 2,6-bis(4-naphthalen-1-ylphenyl)-4-[4-(3-pyridyl)phenyl]pyrimidine (abbreviation: 2,4NP-6PyPPm), 9-[4-(4,6-diphenyl-1,3,5-triazin-2-yl)-2-dibenzothiophenyl]-2-phenyl-9H-carbazole (abbreviation: PCDBfTzn), 2-[1,1'-biphenyl]-3-yl-4-phenyl-6-(8-[1,1':4',1''-terphenyl]-4-yl-1-dibenzofuranyl)-1,3,5-triazine (abbreviation: mBP-TPDBfTzn), 2-{3-[3-(dibenzothiophen-4-yl)phenyl]phenyl}-4,6-diphenyl-1,3,5-triazine (abbreviation: mDBtBPTzn), or mFBPTzn, and a heteroaromatic compound including a heteroaromatic ring having a diazine (pyrimidine) ring, such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 4,6mCzBP2Pm, 6-(1,1'-biphenyl-3-yl)-4-[3,5-bis(9H-carbazol-9-yl)phenyl]-2-phenylpyrimidine (abbreviation: 6mBP-4Cz2PPm), 4-[3,5-bis(9H-carbazol-9-yl)phenyl]-2-phenyl-6-(1,1'-biphenyl-4-yl)pyrimidine (abbreviation: 6BP-4Cz2PPm), 4-[3-(dibenzothiophen-4-yl)phenyl]-8-(naphthalen-2-yl)-[1]benzofuro[3,2-d]pyrimidine (abbreviation: 8βN-4mDBtPBfpm), 8BP-4mDBtPBfpm, 9mDBtBPNfpr, 9pmDBtBPNfpr, 3,8-bis[3-(dibenzothiophen-4-yl)phenyl]benzofuro[2,3-b]pyrazine (abbreviation: 3,8mDBtP2Bfpr), 4,8-bis[3-(dibenzothiophen-4-yl)phenyl]-[1]benzofuro[3,2-d]pyrimidine (abbreviation: 4,8mDBtP2Bfpm), 8-[3'-(dibenzothiophen-4-yl)(1,1'-biphenyl-3-yl)]naphtho[1',2': 4,5]furo[3,2-d]pyrimidine (abbreviation: 8mDBtBPNfpm), or 8-[(2,2'-binaphthalen)–6-yl]-4-[3-(dibenzothiophen-4-yl)phenyl]-[1]benzofuro[3,2-d]pyrimidine (abbreviation: 8(PN2)-4mDBtPBfpm). Note that the above aromatic compounds including a heteroaromatic ring include a heteroaromatic compound having a fused heteroaromatic ring.

Other examples include a heteroaromatic compound including a heteroaromatic ring having a diazine (pyrimidine) ring, such as 2,2'-(pyridine-2,6-diyl)bis(4-phenylbenzo[h]quinazoline) (abbreviation: 2,6(P-Bqn)2Py), 2,2'-(2,2'-bipyridine-6,6'-diyl)bis(4-phenylbenzo[h]quinazoline) (abbreviation: 6,6'(P-Bqn)2BPy), 2,2'-(pyridine-2,6-diyl)bis{4-[4-(2-naphthyl)phenyl]-6-phenylpyrimidine} (abbreviation: 2,6(NP-PPm)2Py), or 6-(1,1'-biphenyl-3-yl)-4-[3,5-bis(9H-carbazol-9-yl)phenyl]-2-phenylpyrimidine (abbreviation: 6mBP-4Cz2PPm), and a heteroaromatic compound including a heteroaromatic ring having a triazine ring, such as 2,4,6-tris(3'-(pyridin-3-yl)biphenyl-3-yl)-1,3,5-triazine (abbreviation: TmPPPyTz), 2,4,6-tris(2-pyridyl)-1,3,5-triazine (abbreviation: 2Py3Tz), or 2-[3-(2,6-dimethyl-3- pyridyl)-5-(9-phenanthryl)phenyl]-4,6-diphenyl-1,3,5-triazine (abbreviation: mPn-mDMePyPTzn).

Specific examples of the above-described heteroaromatic compound having a fused ring structure including the above six-membered ring structure as a part (a heteroaromatic compound having a fused ring structure) include a heteroaromatic compound having a quinoxaline ring, such as bathophenanthroline (abbreviation: BPhen), bathocuproine (abbreviation: BCP), 2,9-bis(naphthalen-2-yl)-4,7-diphenyl-1,10-phenanthroline (abbreviation: NBPhen), 2,2-(1,3-phenylene)bis[9-phenyl-1,10-phenanthroline] (abbreviation: mPPhen2P), 2,2'-(pyridine-2,6-diyl)bis(4-phenylbenzo[h]quinazoline) (abbreviation: 2,6(P-Bqn)2Py), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), or 2mpPCBPDBq.

For the electron-transport layers (114, 114a, and 114b), any of the metal complexes given below as well as the heteroaromatic compounds described above can be used. Examples of the metal complexes include a metal complex having a quinoline ring or a benzoquinoline ring, such as tris(8-quinolinolato)aluminum(III) (abbreviation: $Alq_3$), $Almq_3$, 8-quinolinolatolithium(I) (abbreviation: Liq), $BeBq_2$, bis(2-methyl-8-quinolinolato) (4-phenylphenolato) aluminum(III) (abbreviation: BAlq), or bis(8-quinolinolato)zinc(II) (abbreviation: Znq), and a metal complex having an oxazole ring or a thiazole ring, such as bis[2-(2-benzoxazolyl)phenolato]zinc(II) (abbreviation: ZnPBO) or bis[2-(2-benzothiazolyl)phenolato]zinc(II) (abbreviation: ZnBTZ).

High-molecular compounds such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be used as the electron-transport material.

Each of the electron-transport layers (114, 114a, and 114b) is not limited to a single layer and may be a stack of two or more layers each containing any of the above substances.

<Electron-Injection Layer>

The electron-injection layers (115, 115a, and 115b) contain a substance having a high electron-injection property. The electron-injection layers (115, 115a, and 115b) are layers for increasing the efficiency of electron injection from the second electrode 102 and are preferably formed using a material whose value of the LUMO level has a small difference (0.5 eV or less) from the work function of a material used for the second electrode 102. Thus, the electron-injection layer 115 can be formed using an alkali metal, an alkaline earth metal, or a compound thereof, such as lithium, cesium, lithium fluoride (LiF), cesium fluoride (CsF), calcium fluoride ($CaF_2$), 8-quinolinolato-lithium (abbreviation: Liq), 2-(2-pyridyl)phenolatolithium (abbreviation: LiPP), 2-(2-pyridyl)-3-pyridinolatolithium (abbreviation: LiPPy), 4-phenyl-2-(2-pyridyl)phenolatolithium (abbreviation: LiPPP), an oxide of lithium ($LiO_x$), or cesium carbonate. A rare earth metal and a compound thereof such as erbium fluoride ($ErF_3$) and ytterbium (Yb) can also be used. To form the electron-injection layers (115, 115a, and 115b), a plurality of kinds of materials given above may be mixed or stacked. Electride may also be used for the electron-injection layers (115, 115a, and 115b). Examples of the electride include a substance in which electrons are added at high concentration to calcium oxide-aluminum oxide. Any of the substances used for the electron-transport layers (114, 114a, and 114b), which are given above, can also be used.

A mixed material in which an organic compound and an electron donor (donor) are mixed may also be used for the electron-injection layers (115, 115a, and 115b). Such a mixed material is excellent in an electron-injection property and an electron-transport property because electrons are generated in the organic compound by the electron donor. The organic compound here is preferably a material excellent in transporting the generated electrons; specifically, for example, the above-described electron-transport materials used for the electron-transport layers (114, 114a, and 114b), such as a metal complex and a heteroaromatic compound, can be used. As the electron donor, a substance showing an electron-donating property with respect to an organic compound is used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. Alternatively, a Lewis base such as magnesium oxide can be used. Further alternatively, an organic compound such as tetrathiafulvalene (abbreviation: TTF) can be used. Alternatively, a stack of two or more of these materials may be used.

A mixed material in which an organic compound and a metal are mixed may also be used for the electron-injection layers (115, 115a, and 115b). The organic compound used here preferably has a LUMO level higher than or equal to −3.6 eV and lower than or equal to −2.3 eV. Moreover, a material having an unshared electron pair is preferable.

Thus, as the organic compound used in the above mixed material, a mixed material obtained by mixing a metal and the heteroaromatic compound given above as the material that can be used for the electron-transport layer may be used. Preferred examples of the heteroaromatic compound include materials having an unshared electron pair, such as a heteroaromatic compound having a five-membered ring structure (e.g., an imidazole ring, a triazole ring, an oxazole ring, an oxadiazole ring, a thiazole ring, or a benzimidazole ring), a heteroaromatic compound having a six-membered ring structure (e.g., a pyridine ring, a diazine ring (including a pyrimidine ring, a pyrazine ring, a pyridazine ring, or the like), a triazine ring, a bipyridine ring, or a terpyridine ring), and a heteroaromatic compound having a fused ring structure including a six-membered ring structure as a part (e.g., a quinoline ring, a benzoquinoline ring, a quinoxaline ring, a dibenzoquinoxaline ring, or a phenanthroline ring). Since the materials are specifically described above, description thereof is omitted here.

As a metal used for the above mixed material, a transition metal that belongs to Group 5, Group 7, Group 9, or Group 11 or a material that belongs to Group 13 in the periodic table is preferably used, and examples include Ag, Cu, Al, and In. Here, the organic compound forms a singly occupied molecular orbital (SOMO) with the transition metal.

To amplify light obtained from the light-emitting layer 113b, for example, the optical path length between the second electrode 102 and the light-emitting layer 113b is preferably less than one fourth of the wavelength X of light emitted from the light-emitting layer 113b. In that case, the optical path length can be adjusted by changing the thickness of the electron-transport layer 114b or the electron-injection layer 115b.

When the charge-generation layer 106 is provided between the two EL layers (103a and 103b) as in the light-emitting device in FIG. 1D, a structure in which a plurality of EL layers are stacked between the pair of electrodes (the structure is also referred to as a tandem structure) can be obtained.

<Charge-Generation Layer>

The charge-generation layer 106 has a function of injecting electrons into the EL layer 103a and injecting holes into the EL layer 103b when voltage is applied between the first electrode (anode) 101 and the second electrode (cathode) 102. The charge-generation layer 106 may be either a p-type layer in which an electron acceptor (acceptor) is added to a hole-transport material or an electron-injection buffer layer in which an electron donor (donor) is added to an electron-transport material. Alternatively, both of these layers may be stacked. Furthermore, an electron-relay layer may be provided between the p-type layer and the electron-injection buffer layer. Note that forming the charge-generation layer 106 with the use of any of the above materials can inhibit an increase in driving voltage caused by the stack of the EL layers.

In the case where the charge-generation layer 106 is a p-type layer in which an electron acceptor is added to a hole-transport material, which is an organic compound, any of the materials described in this embodiment can be used as the hole-transport material. Examples of the electron acceptor include 7,7,8,8-tetracyano-2,3,5,6-tetrafluoroquinodimethane (abbreviation: $F_4$-TCNQ) and chloranil. Other examples include oxides of metals that belong to Group 4 to Group 8 of the periodic table. Specific examples include vanadium oxide, niobium oxide, tantalum oxide, chromium oxide, molybdenum oxide, tungsten oxide, manganese oxide, and rhenium oxide. Any of the above-described acceptor materials may be used. Furthermore, a mixed film obtained by mixing materials of a p-type layer or a stack of films containing the respective materials may be used.

In the case where the charge-generation layer 106 is an electron-injection buffer layer in which an electron donor is added to an electron-transport material, any of the materials described in this embodiment can be used as the electron-transport material. As the electron donor, it is possible to use an alkali metal, an alkaline earth metal, a rare earth metal, a metal belonging to Group 2 or Group 13 of the periodic table, or an oxide or a carbonate thereof. Specifically, lithium (Li), cesium (Cs), magnesium (Mg), calcium (Ca), ytterbium (Yb), indium (In), lithium oxide ($Li_2O$), cesium carbonate, or the like is preferably used. An organic compound such as tetrathianaphthacene may be used as the electron donor.

When an electron-relay layer is provided between a p-type layer and an electron-injection buffer layer in the charge-generation layer 106, the electron-relay layer contains at least a substance having an electron-transport property and has a function of preventing an interaction between the electron-injection buffer layer and the p-type layer and transferring electrons smoothly. The LUMO level of the substance having an electron-transport property in the electron-relay layer is preferably between the LUMO level of the acceptor substance in the p-type layer and the LUMO level of the substance having an electron-transport property in the electron-transport layer in contact with the charge-generation layer 106. Specifically, the LUMO level of the substance having an electron-transport property in the electron-relay layer is preferably higher than or equal to −5.0 eV, further preferably higher than or equal to −5.0 eV and lower than or equal to −3.0 eV. Note that as the substance having an electron-transport property in the electron-relay layer, a phthalocyanine-based material or a metal complex having a metal-oxygen bond and an aromatic ligand is preferably used.

Although FIG. 1D illustrates the structure in which two EL layers 103 are stacked, three or more EL layers may be stacked with charge-generation layers each provided between two adjacent EL layers.

<Substrate>

The light-emitting device described in this embodiment can be formed over a variety of substrates. Note that the type of substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base material film.

Examples of the glass substrate include a barium borosilicate glass substrate, an aluminoborosilicate glass substrate, and a soda lime glass substrate. Examples of the flexible substrate, the attachment film, and the base material film include plastics typified by polyethylene terephthalate (PET), polyethylene naphthalate (PEN), and polyether sulfone (PES), a synthetic resin such as acrylic, polypropylene, polyester, polyvinyl fluoride, polyvinyl chloride, polyamide, polyimide, aramid, epoxy, an inorganic vapor deposition film, and paper.

For fabrication of the light-emitting device in this embodiment, a gas phase method such as an evaporation method or a liquid phase method such as a spin coating method or an ink-jet method can be used. When an evaporation method is used, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the layers having various functions (the hole-injection layer 111, the hole-transport layer 112, the light-emitting layer 113, the electron-transport layer 114, and the electron-injection layer 115 included in the EL layers of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

In the case where a film formation method such as the coating method or the printing method is employed, a high molecular compound (e.g., an oligomer, a dendrimer, or a polymer), a middle molecular compound (a compound between a low molecular compound and a high molecular compound with a molecular weight of 400 to 4000), an inorganic compound (e.g., a quantum dot material), or the like can be used. The quantum dot material can be a colloidal quantum dot material, an alloyed quantum dot material, a core-shell quantum dot material, a core quantum dot material, or the like.

Materials that can be used for the layers (the hole-injection layer 111, the hole-transport layer 112, the light-emitting layer 113, the electron-transport layer 114, and the electron-injection layer 115) included in the EL layer 103 of the light-emitting device described in this embodiment are not limited to the materials described in this embodiment, and other materials can be used in combination as long as the functions of the layers are fulfilled.

The structures described in this embodiment can be used in combination with any of the structures described in the other embodiments as appropriate.

Embodiment 3

In this embodiment, specific structure examples and manufacturing methods of a light-emitting apparatus (also referred to as a display panel) of one embodiment of the present invention will be described.

<Structure example 1 of light-emitting apparatus 700>

A light-emitting apparatus 700 illustrated in FIG. 2A includes a light-emitting device 550B, a light-emitting device 550G, a light-emitting device 550R, and a partition 528. The light-emitting device 550B, the light-emitting device 550G, the light-emitting device 550R, and the partition 528 are formed over a functional layer 520 provided over a first substrate 510. The functional layer 520 includes, for example, a driver circuit GD, a driver circuit SD, and the like that are composed of a plurality of transistors, and wirings that electrically connect these circuits. Note that these driver circuits are electrically connected to the light-emitting device 550B, the light-emitting device 550G, and the light-emitting device 550R, for example, to drive them. The light-emitting apparatus 700 includes an insulating layer 705 over the functional layer 520, the light-emitting device 550B, the light-emitting device 550G, the light-emitting device 550R, and the partition 528, and the insulating layer 705 has a function of attaching a second substrate 770 and the functional layer 520. The driver circuit GD and the driver circuit SD will be described in Embodiment 4.

The light-emitting device 550B, the light-emitting device 550G, and the light-emitting device 550R each have the device structure described in Embodiment 2. That is, the case is described in which the EL layer 103 in the structure illustrated in FIG. TA differs between the light-emitting devices.

In this specification and the like, a structure in which light-emitting layers in light-emitting devices of different colors (e.g., blue (B), green (G), and red (R)) are separately formed or separately patterned may be referred to as a side-by-side (SBS) structure.

As illustrated in FIG. 2A, the light-emitting device 550B includes an electrode 551B, an electrode 552, and an EL layer 103B. Note that a specific structure of each layer is as described in Embodiment 2. The EL layer 103B has a stacked-layer structure of layers having different functions including a light-emitting layer. Although FIG. 2A illustrates only a hole-injection/transport layer 104B, an electron-transport layer 108B, and an electron-injection layer 109 as layers of the EL layer 103B, which includes the light-emitting layer, the present invention is not limited thereto. Note that the hole-injection/transport layer 104B represents the layer having the functions of the hole-injection layer and the hole-transport layer described in Embodiment 2 and may have a stacked-layer structure. Note that in this specification, a hole-injection/transport layer in any light-emitting device can be interpreted in the above manner.

The electron-transport layer 108B can have a function of blocking holes moving from the anode side to the cathode side through the light-emitting layer. The electron-injection layer 109 may have a stacked-layer structure in which some or all of layers are formed using different materials.

As illustrated in FIG. 2A, an insulating layer 107B may be formed on side surfaces (or end portions) of the hole-injection/transport layer 104B, the light-emitting layer, and the electron-transport layer 108B, which are included in the EL layer 103B including the light-emitting layer. The insulating layer 107B is formed in contact with side surfaces (or end portions) of the EL layer 103B. Accordingly, entry of oxygen, moisture, or constituent elements thereof through the side surface of the EL layer 103B into the inside of the EL layer 103B can be inhibited. For the insulating layer 107B, aluminum oxide, magnesium oxide, hafnium oxide, gallium oxide, indium gallium zinc oxide, silicon nitride, or silicon nitride oxide can be used, for example. Some of the above-described materials may be stacked to form the insulating layer 107B. The insulating layer 107B can be formed by a sputtering method, a CVD method, an MBE method, a PLD method, an ALD method, or the like and is formed preferably by an ALD method, which achieves favorable coverage.

The electron-injection layer 109 is formed to cover some layers in the EL layer 103B (including the light-emitting layer, the hole-injection/transport layer 104B, and the electron-transport layer 108B) and the insulating layer 107B. The electron-injection layer 109 may have a stacked-layer structure of two or more layers having different electric resistances.

The electrode 552 is formed over the electron-injection layer 109. Note that the electrode 551B and the electrode 552 have an overlap region. The EL layer 103B is positioned between the electrode 551B and the electrode 552.

The EL layer 103B illustrated in FIG. 2A has a structure similar to that of the EL layer 103 described in Embodiment 2. The EL layer 103B is capable of emitting blue light, for example.

As illustrated in FIG. 2A, the light-emitting device 550G includes an electrode 551G, the electrode 552, and an EL layer 103G. Note that a specific structure of each layer is as described in Embodiment 2. The EL layer 103G has a stacked-layer structure of layers having different functions including a light-emitting layer. Although FIG. 2A illustrates only a hole-injection/transport layer 104G, an electron-transport layer 108G, and the electron-injection layer 109 as layers of the EL layer 103G, which includes the light-emitting layer, the present invention is not limited thereto. Note that the hole-injection/transport layer 104G represents the layer having the functions of the hole-injection layer and the hole-transport layer described in Embodiment 2 and may have a stacked-layer structure.

The electron-transport layer 108G can have a function of blocking holes moving from the anode side to the cathode side through the light-emitting layer. The electron-injection layer 109 may have a stacked-layer structure in which some or all of layers are formed using different materials.

As illustrated in FIG. 2A, an insulating layer 107G may be formed on side surfaces (or end portions) of the hole-injection/transport layer 104G, the light-emitting layer, and the electron-transport layer 108G, which are included in the EL layer 103G including the light-emitting layer. The insulating layer 107G is formed in contact with side surfaces (or end portions) of the EL layer 103G. Accordingly, entry of oxygen, moisture, or constituent elements thereof through the side surface of the EL layer 103G into the inside of the EL layer 103G can be inhibited. For the insulating layer 107G, aluminum oxide, magnesium oxide, hafnium oxide, gallium oxide, indium gallium zinc oxide, silicon nitride, or silicon nitride oxide can be used, for example. Some of the above-described materials may be stacked to form the insulating layer 107G. The insulating layer 107G can be formed by a sputtering method, a CVD method, an MBE method, a PLD method, an ALD method, or the like and is formed preferably by an ALD method, which achieves favorable coverage.

The electron-injection layer 109 is formed to cover some layers in the EL layer 103G (including the light-emitting layer, the hole-injection/transport layer 104G, and the electron-transport layer 108G) and the insulating layer 107G. The electron-injection layer 109 may have a stacked-layer structure of two or more layers having different electric resistances.

The electrode 552 is formed over the electron-injection layer 109. Note that the electrode 551G and the electrode 552 have an overlap region. The EL layer 103G is positioned between the electrode 551G and the electrode 552.

The EL layer 103G illustrated in FIG. 2A has a structure similar to that of the EL layer 103 described in Embodiment 2. The EL layer 103G is capable of emitting green light, for example.

As illustrated in FIG. 2A, the light-emitting device 550R includes an electrode 551R, the electrode 552, and an EL layer 103R. Note that a specific structure of each layer is as described in Embodiment 2. The EL layer 103R has a stacked-layer structure of layers having different functions including a light-emitting layer. Although FIG. 2A illustrates only a hole-injection/transport layer 104R, an electron-transport layer 108R, and the electron-injection layer 109 as layers of the EL layer 103R, which includes the light-emitting layer, the present invention is not limited thereto. Note that the hole-injection/transport layer 104R represents the layer having the functions of the hole-injection layer and the hole-transport layer described in Embodiment 2 and may have a stacked-layer structure.

The electron-transport layer 108R can have a function of blocking holes moving from the anode side to the cathode side through the light-emitting layer. The electron-injection layer 109 may have a stacked-layer structure in which some or all of layers are formed using different materials.

As illustrated in FIG. 2A, an insulating layer 107R may be formed on side surfaces (or end portions) of the hole-injection/transport layer 104R, the light-emitting layer, and the electron-transport layer 108R, which are included in the EL layer 103R including the light-emitting layer. The insulating layer 107R is formed in contact with side surfaces (or end portions) of the EL layer 103R. Accordingly, entry of oxygen, moisture, or constituent elements thereof through the side surface of the EL layer 103R into the inside of the EL layer 103R can be inhibited. For the insulating layer 107R, aluminum oxide, magnesium oxide, hafnium oxide, gallium oxide, indium gallium zinc oxide, silicon nitride, or silicon nitride oxide can be used, for example. Some of the above-described materials may be stacked to form the insulating layer 107R. The insulating layer 107R can be formed by a sputtering method, a CVD method, an MBE method, a PLD method, an ALD method, or the like and is formed preferably by an ALD method, which achieves favorable coverage.

The electron-injection layer 109 is formed to cover some layers in the EL layer 103R (including the light-emitting layer, the hole-injection/transport layer 104R, and the electron-transport layer 108R) and the insulating layer 107R. The electron-injection layer 109 may have a stacked-layer structure of two or more layers having different electric resistances.

The electrode 552 is formed over the electron-injection layer 109. Note that the electrode 551R and the electrode 552 have an overlap region. The EL layer 103R is positioned between the electrode 551R and the electrode 552.

The EL layer 103R illustrated in FIG. 2A has a structure similar to that of the EL layer 103 described in Embodiment 2. The EL layer 103R is capable of emitting red light, for example.

The partition 528 is provided between the EL layer 103B, the EL layer 103G, and the EL layer 103R. As illustrated in FIG. 2A, the side surfaces (or end portions) of each of the EL layers (the EL layer 103B, the EL layer 103G, and the EL layer 103R) of the light-emitting devices are in contact with the partition 528 with the insulating layers (107B, 107G, and 107R) therebetween.

In each of the EL layers, particularly the hole-injection layer, which is included in the hole-transport region between the anode and the light-emitting layer, often has high conductivity; thus, a hole-injection layer formed as a layer shared by adjacent light-emitting devices might cause crosstalk. Thus, providing the partition 528 made of an insulating material between the EL layers as shown in this structure example can suppress occurrence of crosstalk between adjacent light-emitting devices.

In the manufacturing method described in this embodiment, a side surface (or an end portion) of the EL layer is exposed in the middle of the patterning step. This accelerates deterioration of the EL layer due to entry of oxygen, water, and the like through the side surface (or the end portion) of the EL layer. Hence, providing the partition 528 can inhibit the deterioration of the EL layer in the manufacturing process.

Furthermore, the partition 528 can flatten the surface by reducing a depression portion generated between adjacent light-emitting devices. When the depression portion is reduced, disconnection of the electrode 552 formed over the EL layers can be inhibited. Examples of an insulating material used to form the partition 528 include organic materials such as an acrylic resin, a polyimide resin, an epoxy resin, an imide resin, a polyamide resin, a polyimide-amide resin, a silicone resin, a siloxane resin, a benzocyclobutene-based resin, a phenol resin, and precursors of these resins. Other examples include organic materials such as polyvinyl alcohol (PVA), polyvinyl butyral, polyvinyl pyrrolidone, polyethylene glycol, polyglycerin, pullulan, water-soluble cellulose, and an alcohol-soluble polyamide resin. A photosensitive resin such as a photoresist can also be used. Examples of the photosensitive resin include positive-type materials and negative-type materials.

For example, the difference between the level of the top surface of the partition 528 and the level of the top surface of any of the EL layer 103B, the EL layer 103G, and the EL layer 103R is preferably 0.5 times or less, and further preferably 0.3 times or less the thickness of the partition 528. The partition 528 may be provided such that the level of the top surface of any of the EL layer 103B, the EL layer 103G, and the EL layer 103R is higher than the level of the top surface of the partition 528, for example. The partition 528 may be provided such that the level of the top surface of the partition 528 is higher than the level of the top surface of the light-emitting layer in any of the EL layer 103B, the EL layer 103G, and the EL layer 103R, for example.

When electrical continuity is established between the EL layer 103B, the EL layer 103G, and the EL layer 103R in a light-emitting apparatus (display panel) with a high resolution exceeding 1000 ppi, crosstalk occurs, resulting in a narrower color gamut that the light-emitting apparatus is capable of reproducing. Providing the partition 528 in a high-resolution display panel with more than 1000 ppi, preferably more than 2000 ppi, or further preferably in an ultrahigh-resolution display panel with more than 5000 ppi allows the display panel to express vivid colors.

Figure 2B:
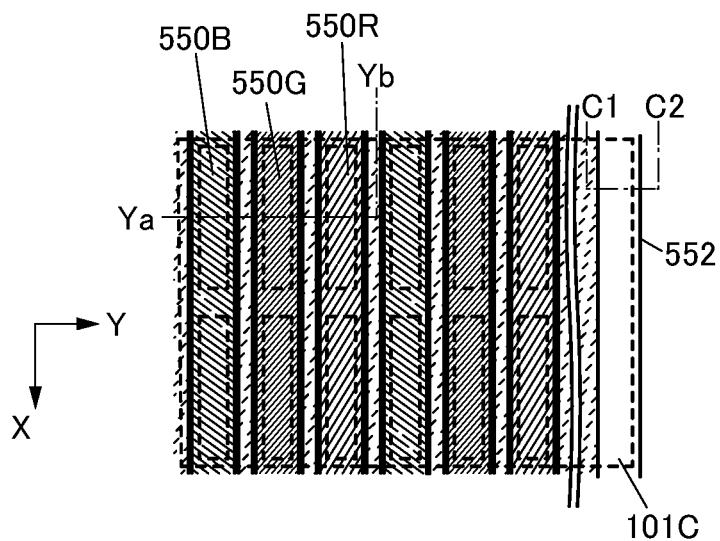

FIG. 2B is a schematic top view of the light-emitting apparatus 700 taken along the dashed-dotted line Ya-Yb in the cross-sectional view of FIG. 2A. Note that FIG. 2B illustrates what is called a stripe arrangement, in which the light-emitting devices of the same color are arranged in the Y direction. In the X direction intersecting with the Y direction, light-emitting devices of the same color are arranged. Specifically, the light-emitting device 550B, the light-emitting device 550G, and the light-emitting device 550R are arranged in a matrix. Note that the arrangement method of the light-emitting devices is not limited thereto; another method such as a delta, zigzag, PenTile, or diamond arrangement may also be used.

The EL layers (103B, 103G, and 103R) are processed to be separated by patterning using a photolithography method; hence, a high-resolution light-emitting apparatus (display panel) can be fabricated. End portions (side surfaces) of the EL layer processed by patterning using a photolithography method have substantially one surface (or are positioned on substantially the same plane). In this case, the width (SE) of a space 580 between the EL layers is preferably 5 m or less, further preferably 1 m or less.

In the EL layer, particularly the hole-injection layer, which is included in the hole-transport region between the anode and the light-emitting layer, often has high conductivity; thus, a hole-injection layer formed as a layer shared by adjacent light-emitting devices might cause crosstalk. Thus, processing the EL layers to be separated by patterning using a photolithography method as shown in this structure example can suppress occurrence of crosstalk between adjacent light-emitting devices.

Figure 2C:
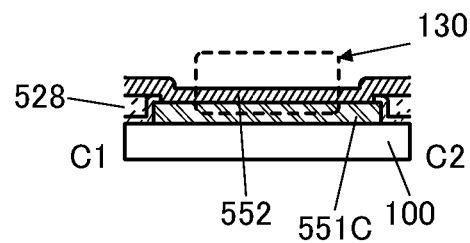

FIG. 2C is a schematic cross-sectional view taken along the dashed-dotted line C1-C2 in FIG. 2B. FIG. 2C illustrates a connection portion 130 where a connection electrode 551C and the electrode 552 are electrically connected to each other. In the connection portion 130, the electrode 552 is provided over and in contact with the connection electrode 551C. The partition 528 is provided to cover an end portion of the connection electrode 551C.

Example 1 of Method for Manufacturing Light-Emitting Apparatus

Figure 3A:
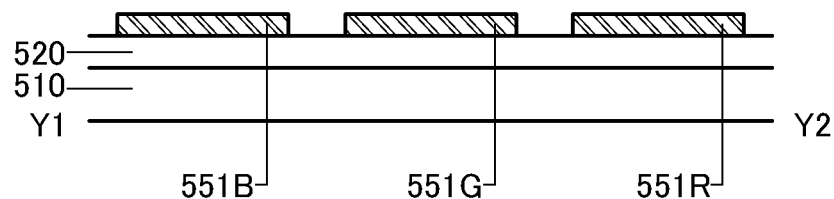
FIGS. 3A to 3C illustrate a method for manufacturing a light-emitting apparatus of an embodiment.

The electrode 551B, the electrode 551G, and the electrode 551R are formed as illustrated in FIG. 3A. For example, a conductive film is formed over the functional layer 520 over the first substrate 510 and processed into predetermined shapes by a photolithography method.

The conductive film can be formed by any of a sputtering method, a chemical vapor deposition (CVD) method, a molecular beam epitaxy (MBE) method, a vacuum evaporation method, a pulsed laser deposition (PLD) method, an atomic layer deposition (ALD) method, and the like. Examples of the CVD method include a plasma-enhanced chemical vapor deposition (PECVD) method and a thermal CVD method. An example of a thermal CVD method is a metal organic CVD (MOCVD) method.

The conductive film may be processed by a nanoimprinting method, a sandblasting method, a lift-off method, or the like as well as a photolithography method described above. Alternatively, island-shaped thin films may be directly formed by a film formation method using a shielding mask such as a metal mask.

There are two typical processing methods using a photolithography method. In one of the methods, a resist mask is formed over a thin film that is to be processed, the thin film is processed by etching or the like, and then the resist mask is removed. In the other method, a photosensitive thin film is formed and then processed into a desired shape by light exposure and development. The former method involves heat treatment steps such as pre-applied bake (PAB) after resist application and post-exposure bake (PEB) after light exposure. In one embodiment of the present invention, a lithography method is used not only for processing of a conductive film but also for processing of a thin film used for the formation of an EL layer (a film made of an organic compound or a film partly including an organic compound).

As light for exposure in a photolithography method, it is possible to use light with the i-line (wavelength: 365 nm), light with the g-line (wavelength: 436 nm), light with the h-line (wavelength: 405 nm), or light in which the i-line, the g-line, and the h-line are mixed. Alternatively, ultraviolet light, KrF laser light, ArF laser light, or the like can be used. Exposure may be performed by liquid immersion exposure technique. As the light for exposure, extreme ultraviolet (EUV) light or X-rays may also be used. Instead of the light for exposure, an electron beam can be used. It is preferable to use EUV, X-rays, or an electron beam because extremely minute processing can be performed. Note that a photomask is not needed when exposure is performed by scanning with a beam such as an electron beam.

For etching of a thin film using a resist mask, a dry etching method, a wet etching method, a sandblasting method, or the like can be used.

Figure 3B:
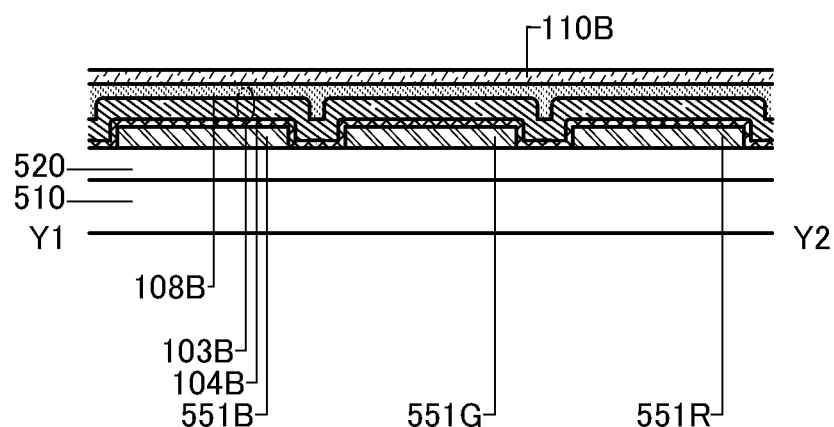

Then, as illustrated in FIG. 3B, the EL layer 103B is formed over the electrode 551B, the electrode 551G, and the electrode 551R. Note that in the EL layer 103B in FIG. 3B, the hole-injection/transport layer 104B, the light-emitting layer, and the electron-transport layer 108B are formed. For example, the EL layer 103B is formed by a vacuum evaporation method over the electrode 551B, the electrode 551G, and the electrode 551R to cover them. Furthermore, a sacrifice layer 110B is formed over the EL layer 103B.

For the sacrifice layer 110B, a film highly resistant to etching treatment performed on the EL layer 103B, i.e., a film having high etching selectivity with respect to the EL layer 103B, can be used. The sacrifice layer 110B preferably has a stacked-layer structure of a first sacrifice layer and a second sacrifice layer which have different etching selectivities to the EL layer 103B. For the sacrifice layer 1101B, it is possible to use a film that can be removed by a wet etching method, which causes less damage to the EL layer 103B. In wet etching, oxalic acid or the like can be used as an etching material. Note that in this specification and the like, a sacrifice layer may be called a mask layer.

For the sacrifice layer 110B, an inorganic film such as a metal film, an alloy film, a metal oxide film, a semiconductor film, or an inorganic insulating film can be used, for example. The sacrifice layer 110B can be formed by any of a variety of film formation methods such as a sputtering method, an evaporation method, a CVD method, and an ALD method.

For the sacrifice layer 110B, a metal material such as gold, silver, platinum, magnesium, nickel, tungsten, chromium, molybdenum, iron, cobalt, copper, palladium, titanium, aluminum, yttrium, zirconium, or tantalum or an alloy material containing the metal material can be used, for example. It is particularly preferable to use a low-melting-point material such as aluminum or silver.

A metal oxide such as indium gallium zinc oxide (also referred to as In—Ga—Zn oxide or IGZO) can be used for the sacrifice layer 110B. It is also possible to use indium oxide, indium zinc oxide (In—Zn oxide), indium tin oxide (In—Sn oxide), indium titanium oxide (In—Ti oxide), indium tin zinc oxide (In—Sn—Zn oxide), indium titanium zinc oxide (In—Ti—Zn oxide), indium gallium tin zinc oxide (In—Ga—Sn—Zn oxide), or the like. Indium tin oxide containing silicon, or the like can also be used.

An element M(M is one or more of aluminum, silicon, boron, yttrium, copper, vanadium, beryllium, titanium, iron, nickel, germanium, zirconium, molybdenum, lanthanum, cerium, neodymium, hafnium, tantalum, tungsten, and magnesium) can be used instead of gallium. In particular, M is preferably one or more of gallium, aluminum, and yttrium.

For the sacrifice layer 1101B, an inorganic insulating material such as aluminum oxide, hafnium oxide, or silicon oxide can be used.

The sacrifice layer 110B is preferably formed using a material that can be dissolved in a solvent which is less likely to chemically influence at least the uppermost film (the electron-transport layer 108B) of the EL layer 103B. Specifically, a material that will be dissolved in water or alcohol can be suitably used for the sacrifice layer 1101B. In formation of the sacrifice layer 110B, it is preferable that application of such a material dissolved in a solvent such as water or alcohol be performed by a wet process and followed by heat treatment for evaporating the solvent. At this time, the heat treatment is preferably performed under a reduced-pressure atmosphere, in which case the solvent can be removed at a low temperature in a short time and thermal damage to the EL layer 103B can be accordingly minimized.

In the case where the sacrifice layer 110B having a stacked-layer structure is formed, the stacked-layer structure can include the first sacrifice layer formed using any of the above-described materials and the second sacrifice layer thereover.

The second sacrifice layer in that case is a film used as a hard mask for etching of the first sacrifice layer. In processing the second sacrifice layer, the first sacrifice layer is exposed. Thus, a combination of films having greatly different etching rates is selected for the first sacrifice layer and the second sacrifice layer. Thus, a film that can be used for the second sacrifice layer can be selected in accordance with the etching conditions of the first sacrifice layer and those of the second sacrifice layer.

For example, in the case where the second sacrifice layer is etched by dry etching involving a fluorine-containing gas (also referred to as fluorine-based gas), the second sacrifice layer can be formed using silicon, silicon nitride, silicon oxide, tungsten, titanium, molybdenum, tantalum, tantalum nitride, an alloy containing molybdenum and niobium, an alloy containing molybdenum and tungsten, or the like. Here, a film of a metal oxide such as IGZO or ITO can be given as an example of a film having a high etching selectivity to the second sacrifice layer (i.e., a film with a low etching rate) in the dry etching involving the fluorine-based gas, and can be used for the first sacrifice layer.

Note that the material for the second sacrifice layer is not limited to the above and can be selected from a variety of materials in view of the etching conditions of the first sacrifice layer and those of the second sacrifice layer. For example, any of the films that can be used for the first sacrifice layer can be used for the second sacrifice layer.

For the second sacrifice layer, for example, a nitride film can be used. Specifically, it is possible to use a nitride such as silicon nitride, aluminum nitride, hafnium nitride, titanium nitride, tantalum nitride, tungsten nitride, gallium nitride, or germanium nitride.

Alternatively, an oxide film can be used for the second sacrifice layer. Typically, it is possible to use a film of an oxide or an oxynitride such as silicon oxide, silicon oxynitride, aluminum oxide, aluminum oxynitride, hafnium oxide, or hafnium oxynitride.

Figure 3C:
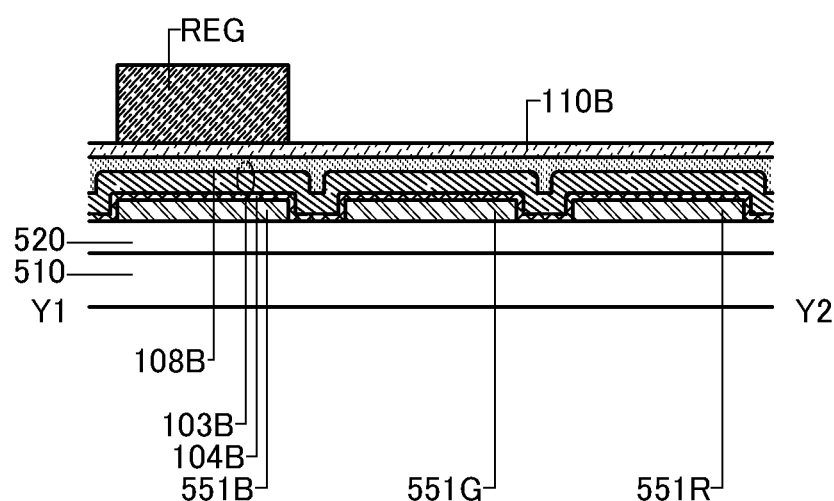

Next, as illustrated in FIG. 3C, a resist is applied onto the sacrifice layer 110B, and the resist having a desired shape (a resist mask REG) is formed by a photolithography method. Such a method involves heat treatment steps such as pre-applied bake (PAB) after the resist application and post-exposure bake (PEB) after light exposure. The temperature reaches approximately 100° C. during the PAB, and approximately 120° C. during the PEB, for example. Therefore, the light-emitting device should be resistant to such high treatment temperatures.

Figure 4A:
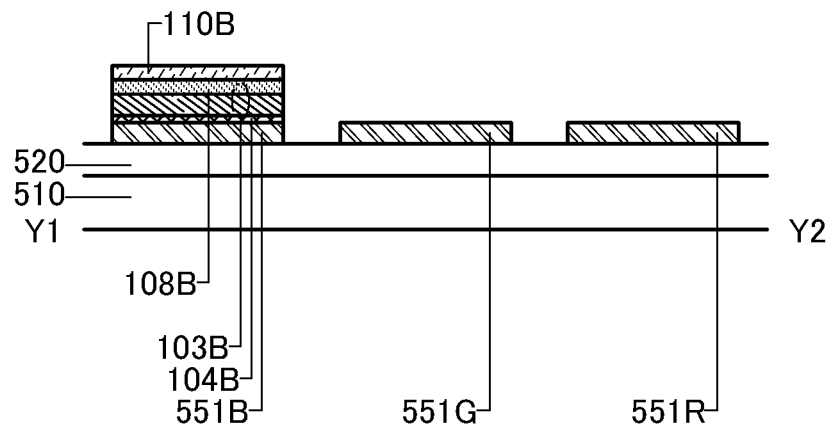
FIGS. 4A to 4C illustrate a method for manufacturing a light-emitting apparatus of an embodiment.

Next, with the use of the obtained resist mask REG, part of the sacrifice layer 110B not covered with the resist mask REG is removed by etching; the resist mask REG is removed; and part of the EL layer 103B not covered with the sacrifice layer 110B is then removed by etching, i.e., the EL layer 103B over the electrode 551G and the EL layer 103B over the electrode 551R are removed by etching, so that the EL layer 103B is processed to have side surfaces (or have their side surfaces exposed) or have a belt-like shape that extends in the direction intersecting the sheet of the diagram. Specifically, dry etching is performed using the sacrifice layer 110B formed in a pattern over the EL layer 103B overlapping with the electrode 551B. Note that in the case where the sacrifice layer 110B has the aforementioned stacked-layer structure of the first sacrifice layer and the second sacrifice layer, the EL layer 103B may be processed into a predetermined shape in the following manner: part of the second sacrifice layer is etched with the use of the resist mask REG, the resist mask REG is then removed, and part of the first sacrifice layer is etched with the use of the second sacrifice layer as a mask. The structure illustrated in FIG. 4A is obtained through these etching steps.

Figure 4B:
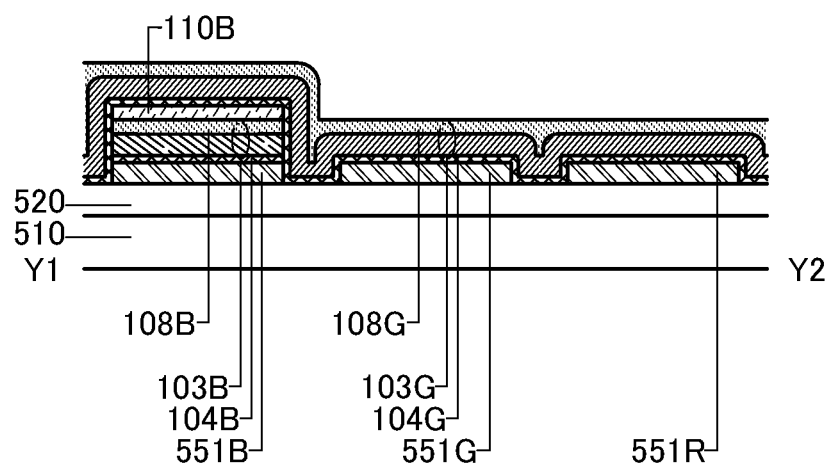

Then, as illustrated in FIG. 4B, the EL layer 103G is formed over the sacrifice layer 110B, the electrode 551G, and the electrode 551R. Note that in the EL layer 103G in FIG. 4B, the hole-injection/transport layer 104G, the light-emitting layer, and the electron-transport layer 108G are formed. For example, the EL layer 103G is formed by a vacuum evaporation method over the sacrifice layer 110B, the electrode 551G, and the electrode 551R to cover them.

Figure 4C:
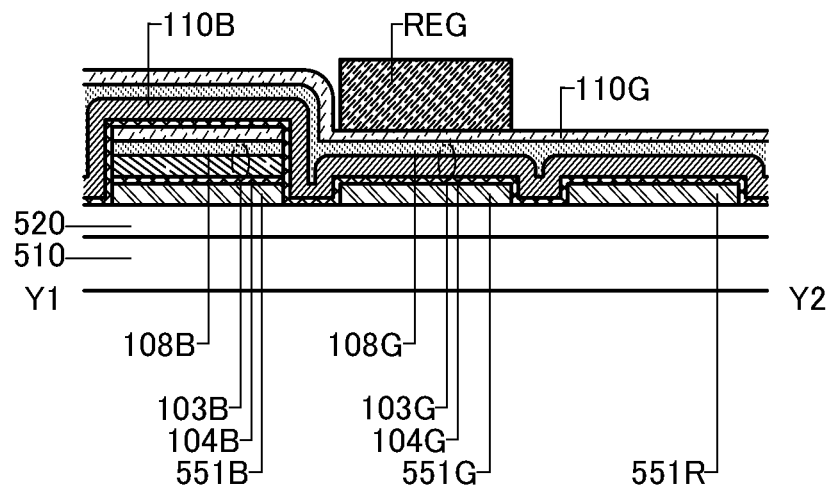
Figure 5A:
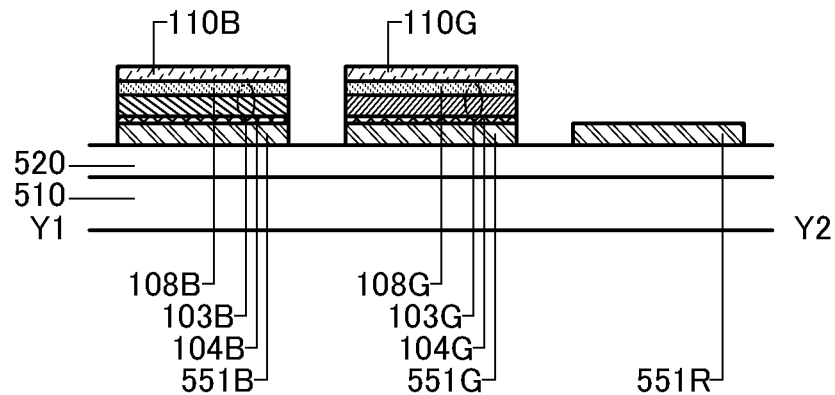
FIGS. 5A to 5C illustrate a method for manufacturing a light-emitting apparatus of an embodiment.

Then, as illustrated in FIG. 4C, a sacrifice layer 110G is formed over the EL layer 103G, a resist is applied onto the sacrifice layer 110G, and the resist having a desired shape (resist mask REG) is formed by a photolithography method. Part of the sacrifice layer 110G not covered with the obtained resist mask is removed by etching, the resist mask is removed, and part of the EL layer 103G not covered with the sacrifice layer 110G is then removed by etching. Thus, the EL layer 103G over the electrode 551B and the EL layer 103G over the electrode 551R are removed by etching, so that the EL layer 103G is processed to have side surfaces (or have their side surfaces exposed) or have a belt-like shape that extends in the direction intersecting the sheet of the diagram as illustrated in FIG. 5A. Note that in the case where the sacrifice layer 110G has the aforementioned stacked-layer structure of the first sacrifice layer and the second sacrifice layer, the EL layer 103G may be processed into a predetermined shape in the following manner: part of the second sacrifice layer is etched with the use of the resist mask, the resist mask is then removed, and part of the first sacrifice layer is etched with the use of the second sacrifice layer as a mask.

Figure 5B:
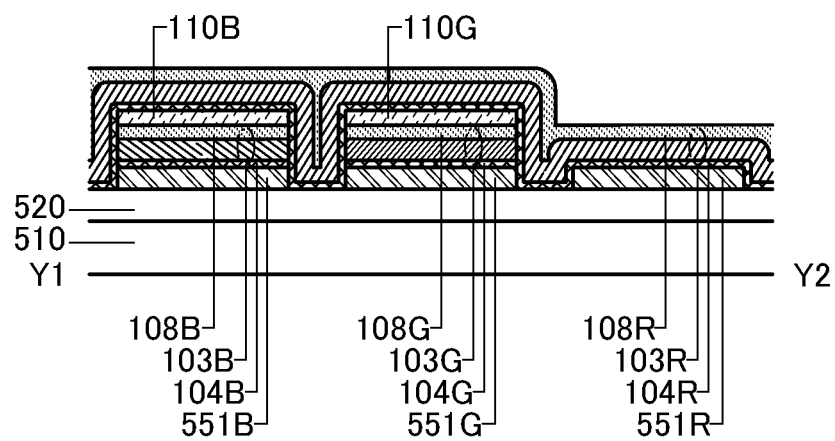

Next, as illustrated in FIG. 5B, the EL layer 103R is formed over the sacrifice layer 110B, the sacrifice layer 110G, and the electrode 551R. Note that in the EL layer 103R in FIG. 5B, the hole-injection/transport layer 104R, the light-emitting layer, and the electron-transport layer 108R are formed. For example, the EL layer 103R is formed by a vacuum evaporation method over the sacrifice layer 110B, the sacrifice layer 110G, and the electrode 551R to cover them.

Figure 5C:
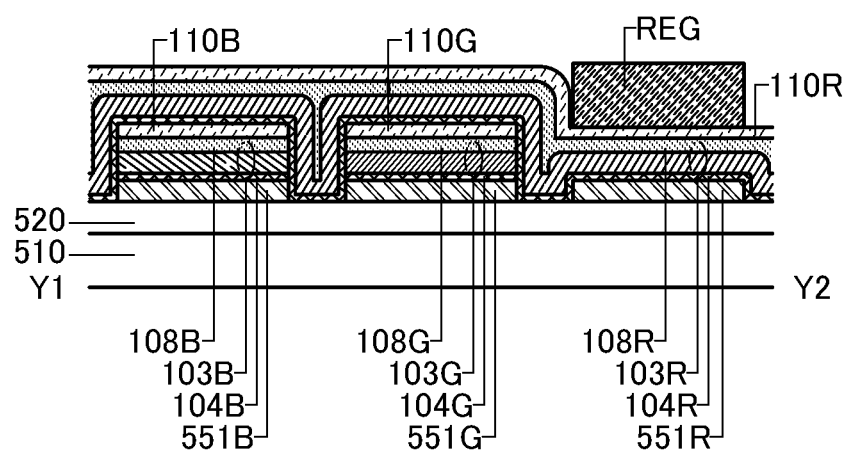
Figure 6A:
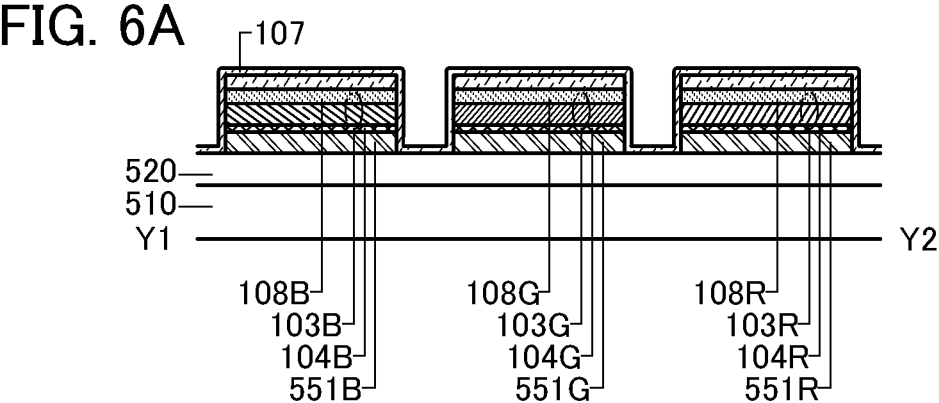
FIGS. 6A to 6C illustrate a method for manufacturing a light-emitting apparatus of an embodiment.

Then, as illustrated in FIG. 5C, a sacrifice layer 110R is formed over the EL layer 103R, a resist is applied onto the sacrifice layer 110R, and the resist having a desired shape (resist mask REG) is formed by a photolithography method. Part of the sacrifice layer 110R not covered with the obtained resist mask is removed by etching, the resist mask is removed, and part of the EL layer 103R not covered with the sacrifice layer 110R is then removed by etching. Thus, the EL layer 103R over the electrode 551B and the EL layer 103R over the electrode 551G are removed by etching, so that the EL layer 103R is processed to have side surfaces (or have their side surfaces exposed) or have a belt-like shape that extends in the direction intersecting the sheet of the diagram. Note that in the case where the sacrifice layer 110R has the aforementioned stacked-layer structure of the first sacrifice layer and the second sacrifice layer, the EL layer 103R may be processed into a predetermined shape in the following manner: part of the second sacrifice layer is etched with the use of the resist mask, the resist mask is then removed, and part of the first sacrifice layer is etched with the use of the second sacrifice layer as a mask. Then, the insulating layer 107 is formed over the sacrifice layers (110B, 110G, and 110R) with the sacrifice layers (110B, 110G, and 110R) remaining over the EL layers (103B, 103G, and 103R), so that the structure illustrated in FIG. 6A is obtained.

Note that the insulating layer 107 can be formed by an ALD method, for example. In this case, the insulating layer 107 is formed in contact with the side surfaces of the EL layers (103B, 103G, and 103R) as illustrated in FIG. 6A. This can inhibit entry of oxygen, moisture, or constituent elements thereof into the inside through the side surfaces of the EL layers (103B, 103G, and 103R). Examples of the material used for the insulating layer 107 include aluminum oxide, magnesium oxide, hafnium oxide, gallium oxide, indium gallium zinc oxide, silicon nitride, and silicon nitride oxide.

Figure 6B:
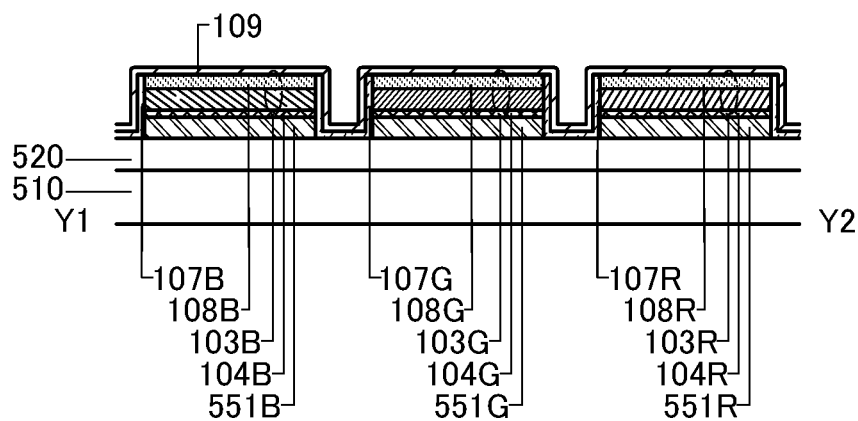

Then, as illustrated in FIG. 6B, the sacrifice layers (110B, 110G, and 110R) are removed, part of the insulating layer 107 is removed to form the insulating layers (107B, 107G, and 107R), and then the electron-injection layer 109 is formed over the EL layers (103B, 103G, and 103R). The electron-injection layer 109 is formed by a vacuum evaporation method, for example. Note that the electron-injection layer 109 is formed over the electron-transport layers (108B, 108G, and 108R). The electron-injection layer 109 is in contact with the side surfaces (or end portions) of the hole-injection/transport layers (104R, 104G, and 104B), the light-emitting layers, and the electron-transport layers (108B, 108G, and 108R) in the EL layers (103B, 103G, and 103R) with the insulating layers (107B, 107G, and 107R) therebetween.

Figure 6C:
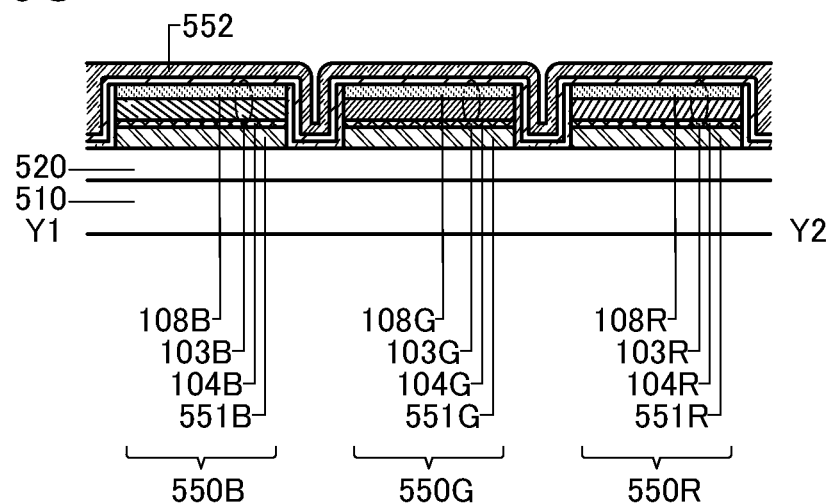

Next, as illustrated in FIG. 6C, the electrode 552 is formed. The electrode 552 is formed by a vacuum evaporation method, for example. The electrode 552 is formed over the electron-injection layer 109. The electrode 552 is in contact with the side surfaces (or end portions) of the EL layers (103B, 103G, and 103R) with the electron-injection layer 109 and the insulating layers (107B, 107G, and 107R) therebetween; note that the EL layers (103B, 103G, and 103R) illustrated in FIG. 6C include the hole-injection/transport layers (104R, 104G, and 104B), the light-emitting layers, and the electron-transport layers (108B, 108G, and 108R). Thus, the EL layers (103B, 103G, and 103R) and the electrode 552, specifically the hole-injection/transport layers (104B, 104G, and 104R) in the EL layers (103B, 103G, and 103R) and the electrode 552 can be prevented from being electrically short-circuited.

Through the above steps, the EL layer 103B, the EL layer 103G, and the EL layer 103R in the light-emitting device 550B, the light-emitting device 550G, and the light-emitting device 550R can be processed to be separated from each other.

The EL layers 103B, 103G, and 103R are processed to be separated by patterning using a photolithography method; hence, a high-resolution light-emitting apparatus (display panel) can be fabricated. End portions (side surfaces) of the EL layer processed by patterning using a photolithography method have substantially one surface (or are positioned on substantially the same plane).

In the EL layer, particularly the hole-injection layer, which is included in the hole-transport region between the anode and the light-emitting layer, often has high conductivity; thus, a hole-injection layer formed as a layer shared by adjacent light-emitting devices might cause crosstalk. Thus, processing the EL layers to be separated by patterning using a photolithography method as shown in this structure example can suppress occurrence of crosstalk between adjacent light-emitting devices.

Structure Example 2 of Light-Emitting Apparatus 700

Figure 7:
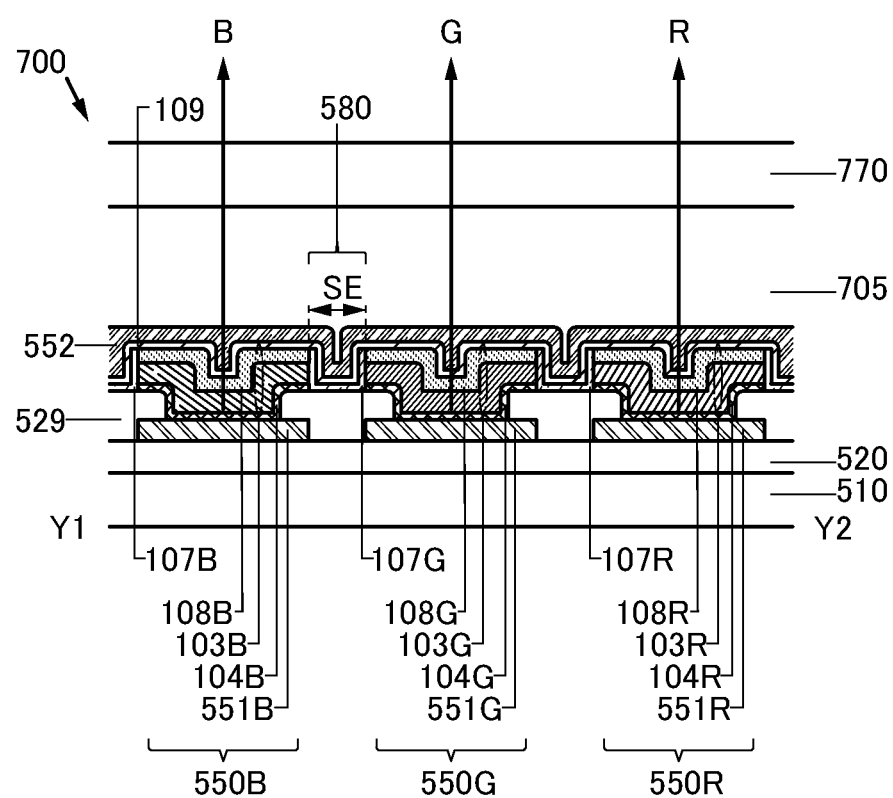
FIG. 7 illustrates a light-emitting apparatus of an embodiment.

The light-emitting apparatus 700 illustrated in FIG. 7 includes the light-emitting device 550B, the light-emitting device 550G, the light-emitting device 550R, and an insulating layer 529. The light-emitting device 550B, the light-emitting device 550G, the light-emitting device 550R, and the insulating layer 529 are formed over the functional layer 520 provided over the first substrate 510. The functional layer 520 includes, for example, the driver circuit GD, the driver circuit SD, and the like that are composed of a plurality of transistors, and wirings that electrically connect these circuits. Note that these driver circuits are electrically connected to the light-emitting device 550B, the light-emitting device 550G, and the light-emitting device 550R, for example, to drive them.

The light-emitting device 550B, the light-emitting device 550G, and the light-emitting device 550R each have the device structure described in Embodiment 2. Specifically, the case is described in which the EL layer 103 in the structure illustrated in FIG. 1A differs between the light-emitting devices.

Note that specific structures of the light-emitting devices illustrated in FIG. 7 are the same as the structures of the light-emitting devices 550B, 550G, and 550R described with reference to FIGS. 2A to 2C.

As illustrated in FIG. 7, the EL layers (103B, 103G, and 103R) of the light-emitting devices (550B, 550G, and 550R)

include the hole-injection/transport layers (104B, 104G, and 104R), the electron-transport layers (108B, 108G, and 108R), and the electron-injection layer 109.

The EL layers in this structure (the EL layers 103B, 103G, and 103R) are processed to be separated by patterning using a photolithography method; hence, end portions (side surfaces) of the processed EL layers have substantially one surface (or are positioned on substantially the same plane).

The EL layers 103B, 103G, and 103R in the light-emitting devices include the space 580 between the adjacent light-emitting devices. When the space 580 is denoted by a distance SE between the EL layers in the adjacent light-emitting devices, decreasing the distance SE can increase the aperture ratio and resolution. By contrast, as the distance SE increases, the effect of variation in the manufacturing process between the adjacent light-emitting devices becomes permissible, which leads to an increase in manufacturing yield. Since the light-emitting device manufactured according to this specification is suitable for a miniaturization process, the distance SE between the EL layers in the adjacent light-emitting devices can be longer than or equal to 0.5 m and shorter than or equal to 5 m, preferably longer than or equal to 1 m and shorter than or equal to 3 m, further preferably longer than or equal to 1 m and shorter than or equal to 2.5 m, still further preferably longer than or equal to 1 m and shorter than or equal to 2 µm. Typically, the distance SE is preferably longer than or equal to 1 m and shorter than or equal to 2 m (e.g., 1.5 m or a neighborhood thereof).

In the EL layer, particularly the hole-injection layer, which is included in the hole-transport region between the anode and the light-emitting layer, often has high conductivity; thus, a hole-injection layer formed as a layer shared by adjacent light-emitting devices might cause crosstalk. Thus, processing the EL layers to be separated by patterning using a photolithography method as shown in this structure example can suppress occurrence of crosstalk between adjacent light-emitting devices.

In this specification and the like, a device formed using a metal mask or a fine metal mask (FMM) may be referred to as a device having a metal mask (MM) structure. In this specification and the like, a device formed without using a metal mask or an FMM may be referred to as a device having a metal maskless (MML) structure.

The structures described in this embodiment can be used in appropriate combination with any of the structures described in the other embodiments.

Embodiment 4

In this embodiment, a light-emitting apparatus of one embodiment of the present invention will be described with reference to FIGS. 8A and 8B, FIGS. 9A and 9B, and FIGS. 10A and 10B. The light-emitting apparatus 700 illustrated in FIGS. 8A and 8B, FIGS. 9A and 9B, and FIGS. 10A and 10B includes the light-emitting device described in Embodiment 2. The light-emitting apparatus 700 described in this embodiment can be referred to as a display panel because it can be used in a display unit of an electronic device and the like.

Figure 8A:
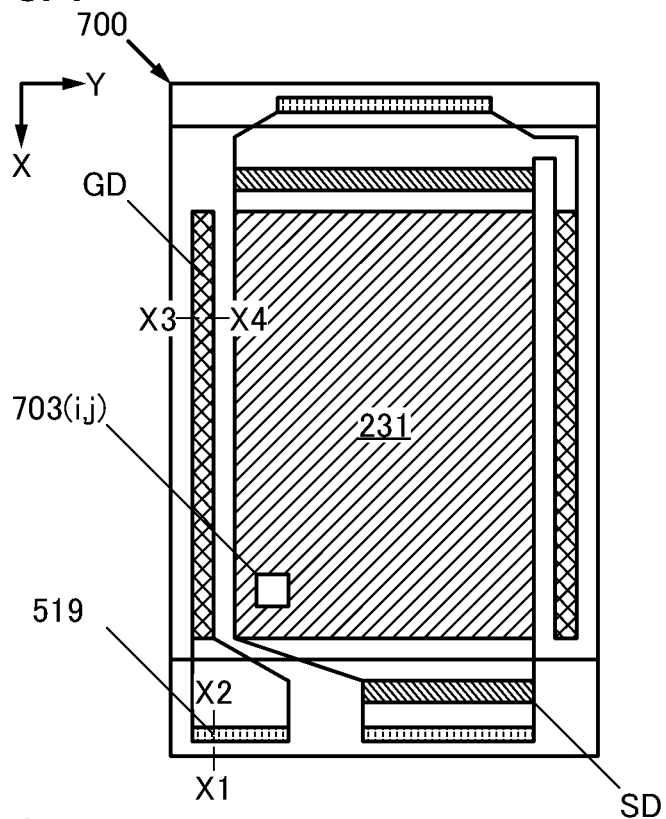
FIGS. 8A and 8B illustrate a light-emitting apparatus of an embodiment.
Figure 8B:
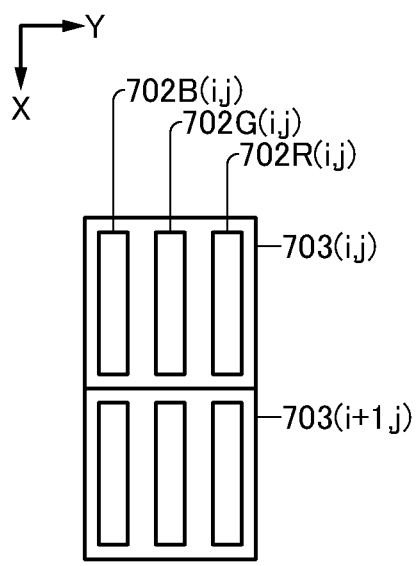

As illustrated in FIG. 8A, the light-emitting apparatus 700 described in this embodiment includes a display region 231, and the display region 231 includes a pixel set 703(*ij*). A pixel set 703(*i*+1j) adjacent to the pixel set 703(*ij*) is provided as illustrated in FIG. 8B.

Note that a plurality of pixels can be used in the pixel 703(*ij*). For example, a plurality of pixels that show colors of different hues can be used. Note that a plurality of pixels can be referred to as subpixels. In addition, a set of subpixels can be referred to as a pixel.

Such a structure enables additive mixture or subtractive mixture of colors shown by the plurality of pixels. Alternatively, it is possible to express a color of a hue that a single pixel cannot show.

Specifically, a pixel 702B(ij) for showing blue, a pixel 702G(ij) for showing green, and a pixel 702R(ij) for showing red can be used in the pixel 703(*ij*). The pixel 702B(ij), the pixel 702G(ij), and the pixel 702R(ij) can each be referred to as a subpixel.

A pixel for showing white or the like in addition to the above set may be used in the pixel 703(*ij*). Moreover, a pixel for showing cyan, a pixel for showing magenta, and a pixel for showing yellow may be used as subpixels in the pixel 703(*ij*).

A pixel that emits infrared light in addition to the above set may be used in the pixel 703(*ij*). Specifically, a pixel that emits light including light with a wavelength of greater than or equal to 650 nm and less than or equal to 1000 nm can be used in the pixel 703(*ij*).

The light-emitting apparatus 700 includes the driver circuit GD and the driver circuit SD around the display region 231 in FIG. 8A. The light-emitting apparatus 700 also includes a terminal 519 electrically connected to the driver circuit GD, the driver circuit SD, and the like. The terminal 519 can be electrically connected to a flexible printed circuit FPC1, for example.

The driver circuit GD has a function of supplying a first selection signal and a second selection signal. For example, the driver circuit GD is electrically connected to an after-mentioned conductive film G1(i) to supply the first selection signal, and is electrically connected to an after-mentioned conductive film G2(i) to supply the second selection signal. The driver circuit SD has a function of supplying an image signal and a control signal, and the control signal includes a first level and a second level. For example, the driver circuit SD is electrically connected to an after-mentioned conductive film S1g(j) to supply the image signal, and is electrically connected to an after-mentioned conductive film S2g(j) to supply the control signal.

Figure 10A:
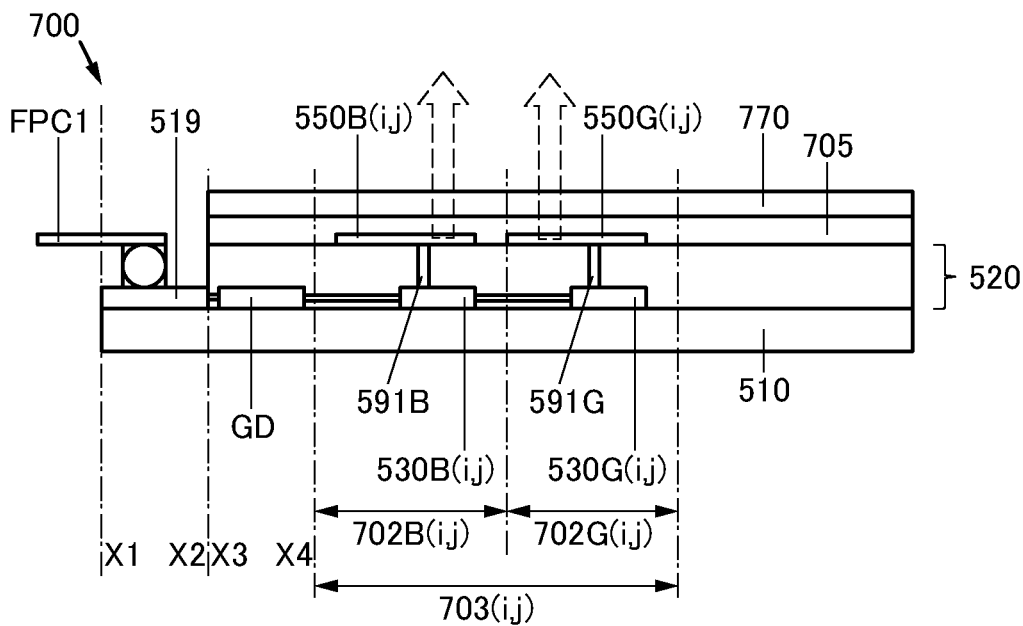
FIGS. 10A and 10B illustrate a light-emitting apparatus of an embodiment.

FIG. 10A illustrates a cross-sectional view of the light-emitting apparatus taken along each of the dashed-dotted line X1-X2 and the dashed-dotted line X3-X4 in FIG. 8A. As illustrated in FIG. 10A, the light-emitting apparatus 700 includes the functional layer 520 between the first substrate 510 and the second substrate 770. The functional layer 520 includes, for example, the driver circuit GD, the driver circuit SD, and the like that are described above and wirings that electrically connect these circuits. Although FIG. 10A illustrates the functional layer 520 including a pixel circuit 530B(ij), a pixel circuit 530G(ij), and the driver circuit GD, the functional layer 520 is not limited thereto.

Each pixel circuit (e.g., the pixel circuit 530B(ij) and the pixel circuit 530G(ij) in FIG. 10A) included in the functional layer 520 is electrically connected to a light-emitting device (e.g., a light-emitting device 550B(ij) and a light-emitting device 550G(ij) in FIG. 10A) formed over the functional layer 520. Specifically, the light-emitting device 550B(ij) is electrically connected to the pixel circuit 530B(ij) through an opening 591B, and the light-emitting device 550G(ij) is electrically connected to the pixel circuit 530G(ij) through an opening 591G. The insulating layer 705 is provided over the functional layer 520 and the light-emitting devices, and has a function of attaching the second substrate 770 and the functional layer 520.

As the second substrate 770, a substrate where touch sensors are arranged in a matrix can be used. For example, a substrate provided with capacitive touch sensors or optical touch sensors can be used as the second substrate 770. Thus, the light-emitting apparatus of one embodiment of the present invention can be used as a touch panel.

Figure 9A:
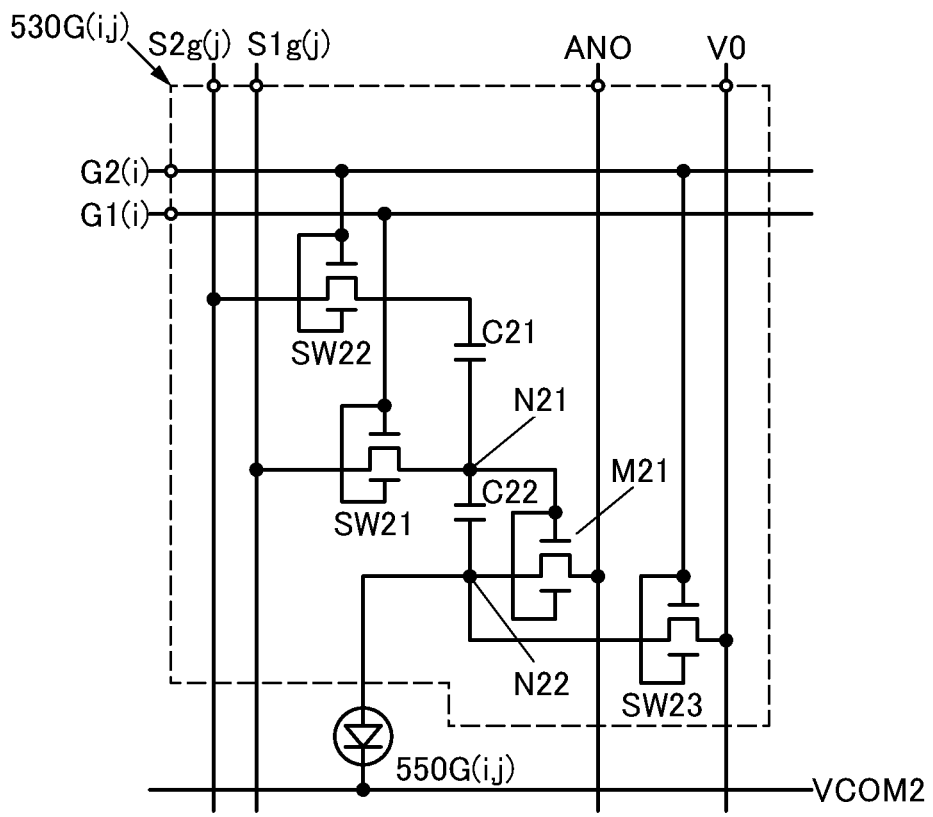
FIGS. 9A and 9B illustrate a light-emitting apparatus of an embodiment.

FIG. 9A illustrates a specific configuration of the pixel circuit 530G(ij).

As illustrated in FIG. 9A, the pixel circuit 530G(ij) includes a switch SW21, a switch SW22, a transistor M21, a capacitor C21, and a node N21. The pixel circuit 530G(ij) also includes a node N22, a capacitor C22, and a switch SW23.

The transistor M21 includes a gate electrode electrically connected to the node N21, a first electrode electrically connected to the light-emitting device 550G(ij), and a second electrode electrically connected to a conductive film ANO.

The switch SW21 includes a first terminal electrically connected to the node N21 and a second terminal electrically connected to the conductive film S1g(j). The switch SW21 has a function of controlling its on/off state on the basis of the potential of the conductive film G1(i).

The switch SW22 includes a first terminal electrically connected to the conductive film S2g(j), and has a function of controlling its on/off state on the basis of the potential of the conductive film G2(i).

The capacitor C21 includes a conductive film electrically connected to the node N21 and a conductive film electrically connected to a second electrode of the switch SW22.

Accordingly, an image signal can be stored in the node N21. Alternatively, the potential of the node N21 can be changed using the switch SW22. Alternatively, the intensity of light emitted from the light-emitting device 550G(i,j) can be controlled with the potential of the node N21.

Figure 9B:
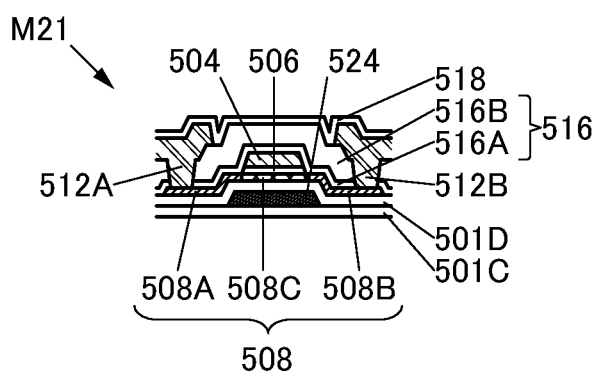

FIG. 9B illustrates an example of a specific structure of the transistor M21 illustrated in FIG. 9A. As the transistor M21, a bottom-gate transistor, a top-gate transistor, or the like can be used as appropriate.

The transistor illustrated in FIG. 9B includes a semiconductor film 508, a conductive film 504, an insulating film 506, a conductive film 512A, and a conductive film 512B. The transistor is formed over an insulating film 501C, for example. The transistor also includes an insulating film 516 (an insulating film 516A and an insulating film 516B) and an insulating film 518.

The semiconductor film 508 includes a region 508A electrically connected to the conductive film 512A and a region 508B electrically connected to the conductive film 512B. The semiconductor film 508 includes a region 508C between the region 508A and the region 508B.

The conductive film 504 includes a region overlapping with the region 508C and has a function of a gate electrode.

The insulating film 506 includes a region positioned between the semiconductor film 508 and the conductive film 504. The insulating film 506 has a function of a first gate insulating film.

The conductive film 512A has one of a function of a source electrode and a function of a drain electrode, and the conductive film 512B has the other.

A conductive film 524 can be used in the transistor. The conductive film 524 includes a region where the semiconductor film 508 is positioned between the conductive film 504 and the conductive film 524. The conductive film 524 has a function of a second gate electrode. An insulating film 501D is positioned between the semiconductor film 508 and the conductive film 524 and has a function of a second gate insulating film.

The insulating film 516 functions as, for example, a protective film covering the semiconductor film 508. Specifically, a film including a silicon oxide film, a silicon oxynitride film, a silicon nitride oxide film, a silicon nitride film, an aluminum oxide film, a hafnium oxide film, an yttrium oxide film, a zirconium oxide film, a gallium oxide film, a tantalum oxide film, a magnesium oxide film, a lanthanum oxide film, a cerium oxide film, or a neodymium oxide film can be used as the insulating film 516, for example.

For the insulating film 518, a material that has a function of inhibiting diffusion of oxygen, hydrogen, water, an alkali metal, an alkaline earth metal, and the like is preferably used. Specifically, the insulating film 518 can be formed using silicon nitride, silicon oxynitride, aluminum nitride, or aluminum oxynitride, for example. In each of silicon oxynitride and aluminum oxynitride, the number of nitrogen atoms contained is preferably larger than the number of oxygen atoms contained.

Note that in a step of forming the semiconductor film used in the transistor of the pixel circuit, the semiconductor film used in the transistor of the driver circuit can be formed. A semiconductor film having the same composition as the semiconductor film used in the transistor of the pixel circuit can be used in the driver circuit, for example.

For the semiconductor film 508, a semiconductor containing an element of Group 14 can be used. Specifically, a semiconductor containing silicon can be used for the semiconductor film 508.

Hydrogenated amorphous silicon can be used for the semiconductor film 508. Microcrystalline silicon or the like can also be used for the semiconductor film 508. In such cases, it is possible to provide a light-emitting apparatus having less display unevenness than a light-emitting apparatus (or a display panel) using polysilicon for the semiconductor film 508, for example. Moreover, it is easy to increase the size of the light-emitting apparatus.

Polysilicon can be used for the semiconductor film 508. In this case, for example, the field-effect mobility of the transistor can be higher than that of a transistor using hydrogenated amorphous silicon for the semiconductor film 508. For another example, the driving capability can be higher than that of a transistor using hydrogenated amorphous silicon for the semiconductor film 508. For another example, the aperture ratio of the pixel can be higher than that in the case of employing a transistor using hydrogenated amorphous silicon for the semiconductor film 508.

For another example, the reliability of the transistor can be higher than that of a transistor using hydrogenated amorphous silicon for the semiconductor film 508.

The temperature required for fabricating the transistor can be lower than that required for a transistor using single crystal silicon, for example.

The semiconductor film used in the transistor of the driver circuit can be formed in the same step as the semiconductor film used in the transistor of the pixel circuit. The driver circuit can be formed over a substrate where the pixel circuit is formed. The number of components of an electronic device can be reduced.

Single crystal silicon can be used for the semiconductor film 508. In this case, for example, the resolution can be higher than that of a light-emitting apparatus (or a display panel) using hydrogenated amorphous silicon for the semiconductor film 508. For another example, it is possible to provide a light-emitting apparatus having less display unevenness than a light-emitting apparatus using polysilicon for the semiconductor film 508. For another example, smart glasses or ahead-mounted display can be provided.

A metal oxide can be used for the semiconductor film 508. In this case, the pixel circuit can hold an image signal for a longer time than a pixel circuit including a transistor that uses amorphous silicon for the semiconductor film. Specifically, a selection signal can be supplied at a frequency of lower than 30 Hz, preferably lower than 1 Hz, further preferably less than once per minute while flickering is suppressed. Consequently, fatigue of a user of an electronic device can be reduced. Furthermore, power consumption for driving can be reduced.

An oxide semiconductor can be used for the semiconductor film 508. Specifically, an oxide semiconductor containing indium, an oxide semiconductor containing indium, gallium, and zinc, or an oxide semiconductor containing indium, gallium, zinc, and tin can be used for the semiconductor film 508.

The use of an oxide semiconductor for the semiconductor film achieves a transistor having lower leakage current in the off state than a transistor using amorphous silicon for the semiconductor film. Thus, a transistor using an oxide semiconductor for the semiconductor film is preferably used as a switch or the like. Note that a circuit in which a transistor using an oxide semiconductor for the semiconductor film is used as a switch is capable of retaining the potential of a floating node for a longer time than a circuit in which a transistor using amorphous silicon for the semiconductor film is used as a switch.

Figure 10B:
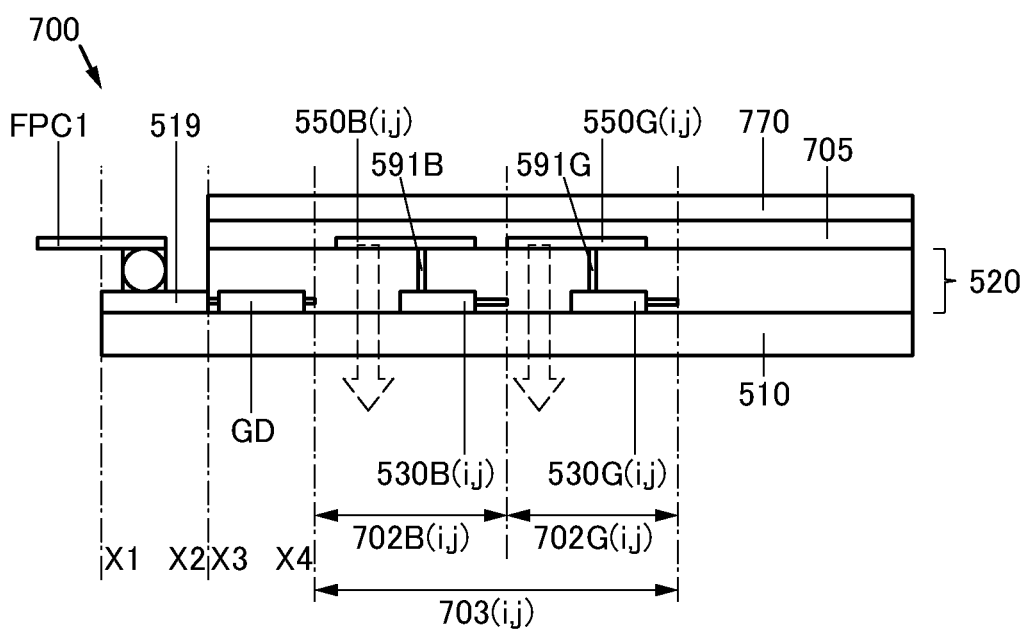

Although the light-emitting apparatus in FIG. 10A has a structure in which light is extracted from the second substrate 770 side (top emission structure), a light-emitting apparatus may have a structure in which light is extracted from the first substrate 510 side (bottom emission structure) as illustrated in FIG. 10B. In a bottom-emission light-emitting apparatus, a first electrode 401 is formed as a transflective electrode and a second electrode 404 is formed as a reflective electrode.

Figure 11A:
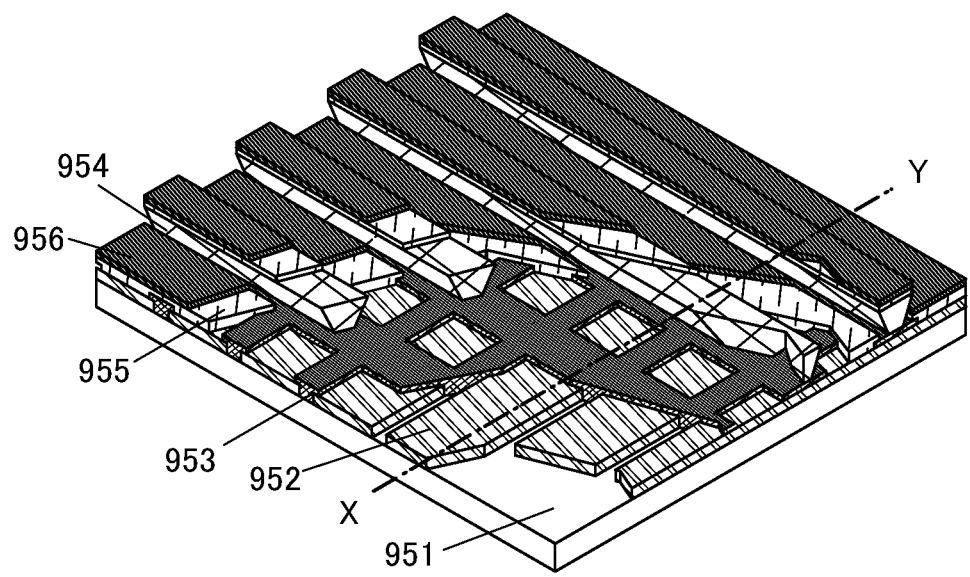
FIGS. 11A and 11B illustrate a light-emitting apparatus of an embodiment.
Figure 11B:
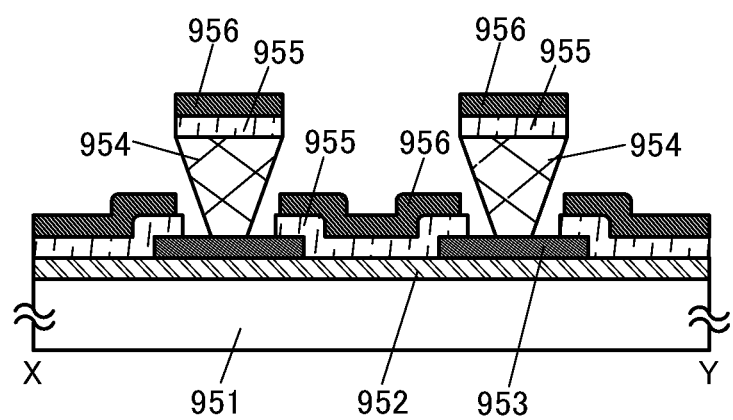

Although FIGS. 10A and 10B illustrate active-matrix light-emitting apparatuses, the structure of the light-emitting device described in Embodiment 2 may be applied to a passive-matrix light-emitting apparatus illustrated in FIGS. 11A and 11B.

FIG. 11A is a perspective view illustrating the passive-matrix light-emitting apparatus, and FIG. 11B illustrates a cross section along the line X-Y in FIG. 11A. In FIGS. 11A and 11B, an electrode 952 and an electrode 956 are provided over a substrate 951, and an EL layer 955 is provided between the electrode 952 and the electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting device due to static electricity or the like.

The structures described in this embodiment can be used in appropriate combination with any of the structures described in the other embodiments.

Embodiment 5

In this embodiment, structures of electronic devices of embodiments of the present invention will be described with reference to FIGS. 12A to 12E, FIGS. 13A to 13E, and FIGS. 14A and 14B.

Figure 12A:
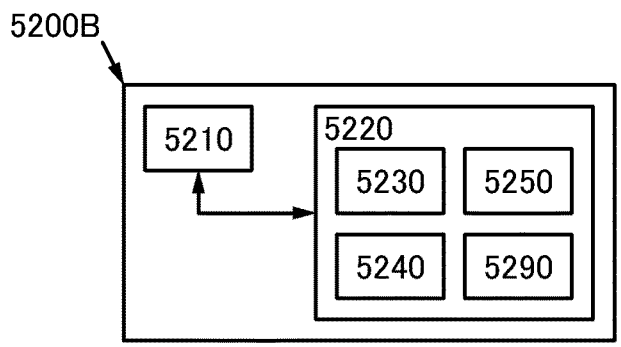
FIGS. 12A to 12E illustrate electronic devices of an embodiment.
Figure 12B:
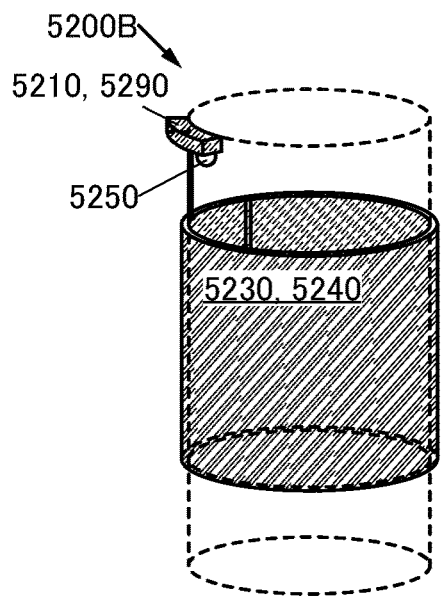
Figure 12C:
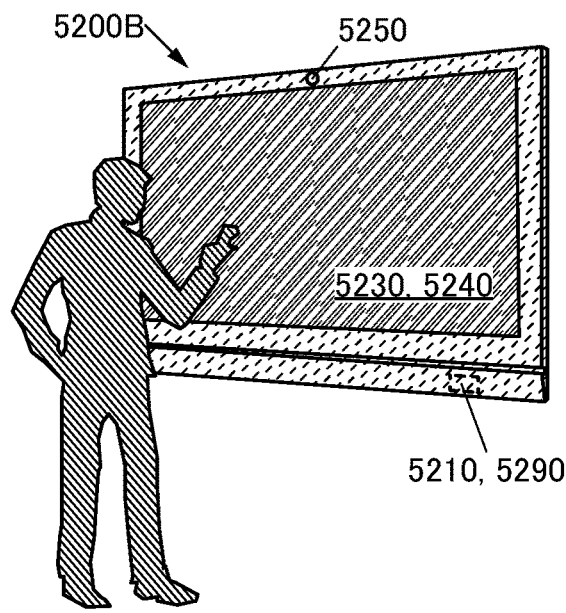
Figure 12D:
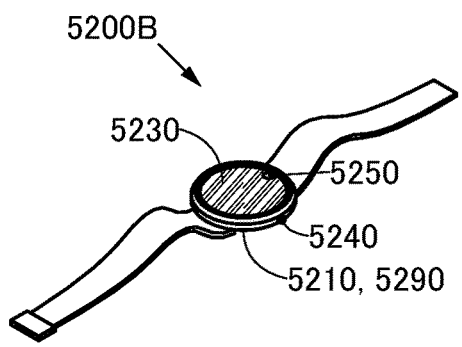
Figure 12E:
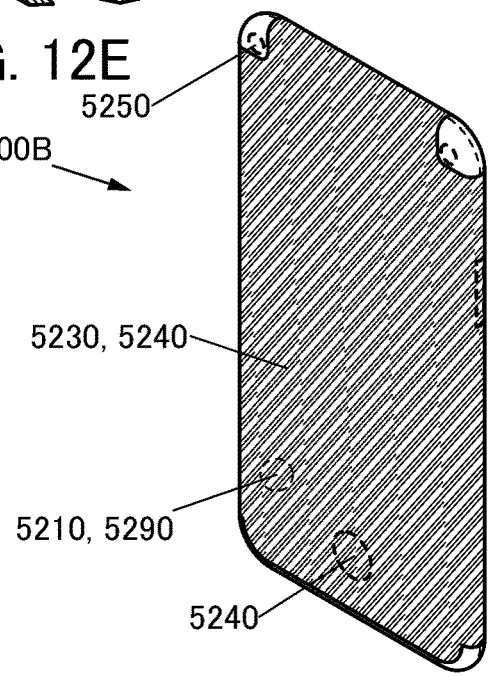
Figure 13A:
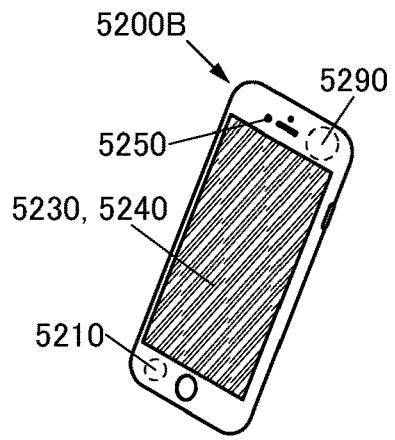
FIGS. 13A to 13E illustrate electronic devices of an embodiment.
Figure 13B:
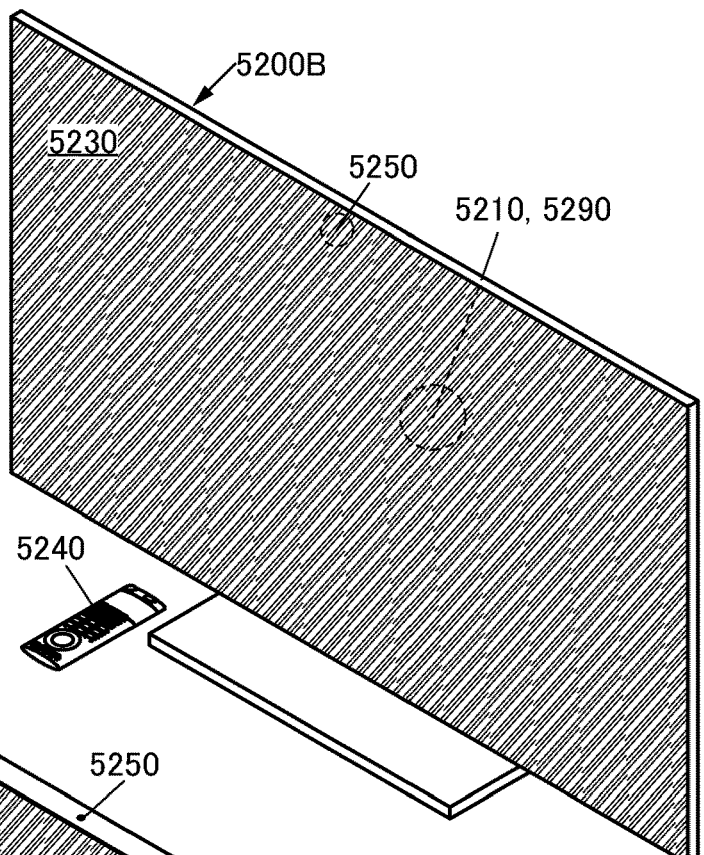
Figure 13C:
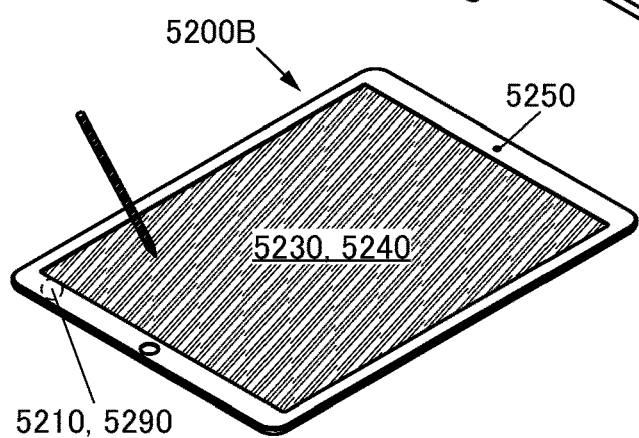
Figure 13D:
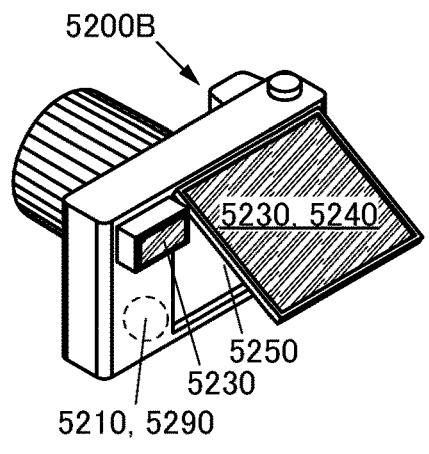
Figure 13E:
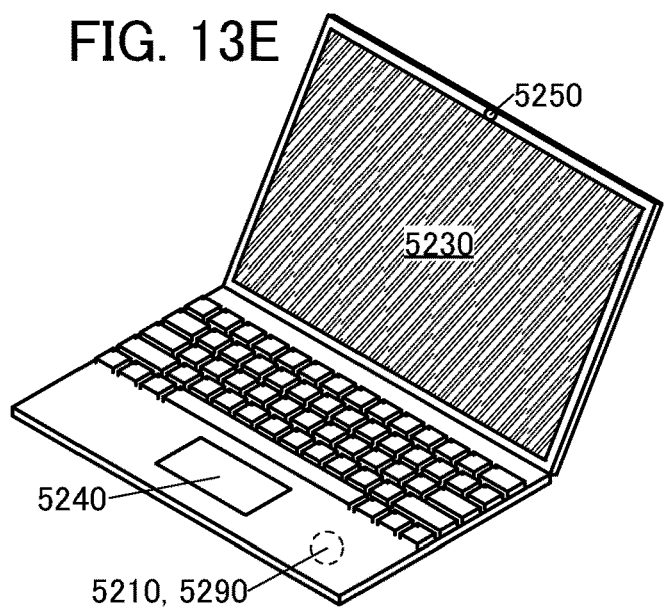
Figure 14A:
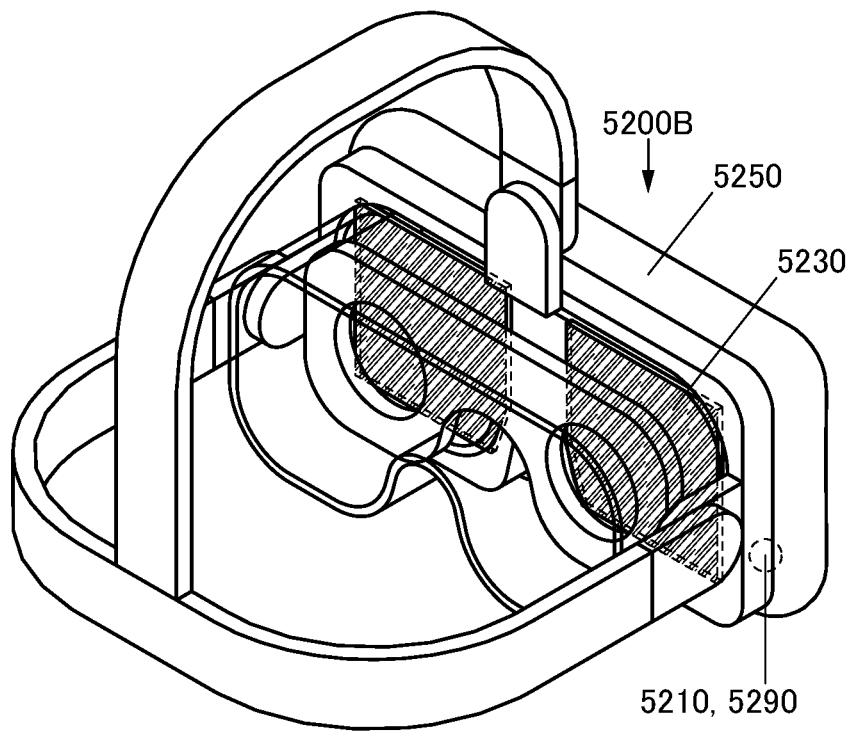
FIGS. 14A and 14B illustrate electronic devices of an embodiment.
Figure 14B:
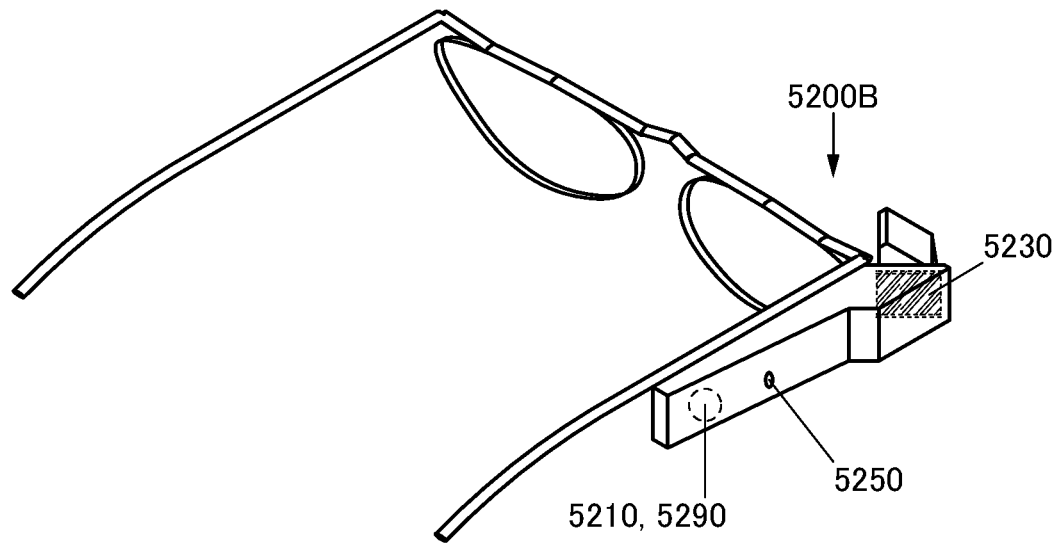

FIGS. 12A to 12E, FIGS. 13A to 13E, and FIGS. 14A and 14B each illustrate a structure of the electronic device of one embodiment of the present invention. FIG. 12A is a block diagram of the electronic device and FIGS. 12B to 12E are perspective views illustrating structures of the electronic device. FIGS. 13A to 13E are perspective views illustrating structures of the electronic device. FIGS. 14A and 14B are perspective views illustrating structures of the electronic device.

An electronic device 5200B described in this embodiment includes an arithmetic device 5210 and an input/output device 5220 (see FIG. 12A).

The arithmetic device 5210 has a function of receiving handling data and a function of supplying image data on the basis of the handling data.

The input/output device 5220 includes a display unit 5230, an input unit 5240, a sensor unit 5250, and a communication unit 5290, and has a function of supplying handling data and a function of receiving image data. The input/output device 5220 also has a function of supplying sensing data, a function of supplying communication data, and a function of receiving communication data.

The input unit 5240 has a function of supplying handling data. For example, the input unit 5240 supplies handling data on the basis of handling by a user of the electronic device 5200B.

Specifically, a keyboard, a hardware button, a pointing device, a touch sensor, an illuminance sensor, an imaging device, an audio input device, an eye-gaze input device, an attitude sensing device, or the like can be used as the input unit 5240.

The display unit 5230 includes a display panel and has a function of displaying image data. For example, the display panel described in Embodiment 2 can be used for the display unit 5230.

The sensor unit 5250 has a function of supplying sensing data. For example, the sensor unit 5250 has a function of sensing a surrounding environment where the electronic device is used and supplying the sensing data.

Specifically, an illuminance sensor, an imaging device, an attitude sensing device, a pressure sensor, a human motion sensor, or the like can be used as the sensor unit 5250.

The communication unit 5290 has a function of receiving and supplying communication data. For example, the communication unit 5290 has a function of being connected to another electronic device or a communication network by wireless communication or wired communication. Specifically, the communication unit 5290 has a function of wireless local area network communication, telephone communication, near field communication, or the like.

FIG. 12B illustrates an electronic device having an outer shape along a cylindrical column or the like. An example of such an electronic device is digital signage. The display panel of one embodiment of the present invention can be used for the display unit 5230. The electronic device may have a function of changing its display method in accordance with the illuminance of a usage environment. The electronic device has a function of changing the displayed content when sensing the existence of a person. Thus, for example, the electronic device can be provided on a column of a building. The electronic device can display advertising, guidance, or the like. The electronic device can be used for digital signage or the like.

FIG. 12C illustrates an electronic device having a function of generating image data on the basis of the path of a pointer used by the user. Examples of such an electronic device include an electronic blackboard, an electronic bulletin board, and digital signage. Specifically, a display panel with a diagonal size of 20 inches or longer, preferably 40 inches or longer, further preferably 55 inches or longer can be used. A plurality of display panels can be arranged and used as one display region. Alternatively, a plurality of display panels can be arranged and used as a multiscreen.

FIG. 12D illustrates an electronic device that is capable of receiving data from another device and displaying the data on the display unit 5230. An example of such an electronic device is a wearable electronic device. Specifically, the electronic device can display several options, and the user can choose some from the options and send a reply to the data transmitter. As another example, the electronic device has a function of changing its display method in accordance with the illuminance of a usage environment. Thus, for example, power consumption of the wearable electronic device can be reduced. As another example, the wearable electronic device can display an image so as to be suitably used even in an environment under strong external light, e.g., outdoors in fine weather.

FIG. 12E illustrates an electronic device including the display unit 5230 having a surface gently curved along a side surface of a housing. An example of such an electronic device is a mobile phone. The display unit 5230 includes a display panel that has a function of displaying images on the front surface, the side surfaces, the top surface, and the rear surface, for example. Thus, a mobile phone can display data on not only its front surface but also its side surfaces, top surface, and rear surface, for example.

FIG. 13A illustrates an electronic device that is capable of receiving data via the Internet and displaying the data on the display unit 5230. An example of such an electronic device is a smartphone. For example, the user can check a created message on the display unit 5230 and send the created message to another device. As another example, the electronic device has a function of changing its display method in accordance with the illuminance of a usage environment. Thus, power consumption of the smartphone can be reduced. As another example, it is possible to obtain a smartphone which can display an image such that the smartphone can be suitably used in an environment under strong external light, e.g., outdoors in fine weather.

FIG. 13B illustrates an electronic device that can use a remote controller as the input unit 5240. An example of such an electronic device is a television system. For example, data received from a broadcast station or via the Internet can be displayed on the display unit 5230. The electronic device can take an image of the user with the sensor unit 5250 and transmit the image of the user. The electronic device can acquire a viewing history of the user and provide it to a cloud service. The electronic device can acquire recommendation data from a cloud service and display the data on the display unit 5230. A program or a moving image can be displayed on the basis of the recommendation data. As another example, the electronic device has a function of changing its display method in accordance with the illuminance of a usage environment. Accordingly, it is possible to obtain a television system which can display an image such that the television system can be suitably used even when irradiated with strong external light that enters the room from the outside in fine weather.

FIG. 13C illustrates an electronic device that is capable of receiving educational materials via the Internet and displaying them on the display unit 5230. An example of such an electronic device is a tablet computer. The user can input an assignment with the input unit 5240 and send it via the Internet. The user can obtain a corrected assignment or the evaluation from a cloud service and have it displayed on the display unit 5230. The user can select suitable educational materials on the basis of the evaluation and have them displayed.

For example, an image signal can be received from another electronic device and displayed on the display unit 5230. When the electronic device is placed on a stand or the like, the display unit 5230 can be used as a sub-display. Thus, for example, it is possible to obtain a tablet computer which can display an image such that the tablet computer is suitably used even in an environment under strong external light, e.g., outdoors in fine weather.

FIG. 13D illustrates an electronic device including a plurality of display units 5230. An example of such an electronic device is a digital camera. For example, the display unit 5230 can display an image that the sensor unit 5250 is capturing. A captured image can be displayed on the sensor unit. A captured image can be decorated using the input unit 5240. A message can be attached to a captured image. A captured image can be transmitted via the Internet. The electronic device has a function of changing shooting conditions in accordance with the illuminance of a usage environment. Accordingly, for example, it is possible to obtain a digital camera that can display a subject such that an image is suitably viewed even in an environment under strong external light, e.g., outdoors in fine weather.

FIG. 13E illustrates an electronic device in which the electronic device of this embodiment is used as a master to control another electronic device used as a slave. An example of such an electronic device is a portable personal computer. For example, part of image data can be displayed on the display unit 5230 and another part of the image data can be displayed on a display unit of another electronic device. Image signals can be supplied. Data written from an input unit of another electronic device can be obtained with the communication unit 5290. Thus, a large display region can be utilized in the case of using a portable personal computer, for example.

FIG. 14A illustrates an electronic device including the sensor unit 5250 that senses an acceleration or a direction. An example of such an electronic device is a goggles-type electronic device. The sensor unit 5250 can supply data on the position of the user or the direction in which the user faces. The electronic device can generate image data for the right eye and image data for the left eye in accordance with the position of the user or the direction in which the user faces. The display unit 5230 includes a display region for the right eye and a display region for the left eye. Thus, a virtual reality image that gives the user a sense of immersion can be displayed on the goggles-type electronic device, for example.

FIG. 14B illustrates an electronic device including an imaging device and the sensor unit 5250 that senses an acceleration or a direction. An example of such an electronic device is a glasses-type electronic device. The sensor unit 5250 can supply data on the position of the user or the direction in which the user faces. The electronic device can generate image data in accordance with the position of the user or the direction in which the user faces. Accordingly, the data can be shown together with a real-world scene, for example. Alternatively, an augmented reality image can be displayed on the glasses-type electronic device.

Note that this embodiment can be combined with any of the other embodiments in this specification as appropriate.

Embodiment 6

Figure 15A:
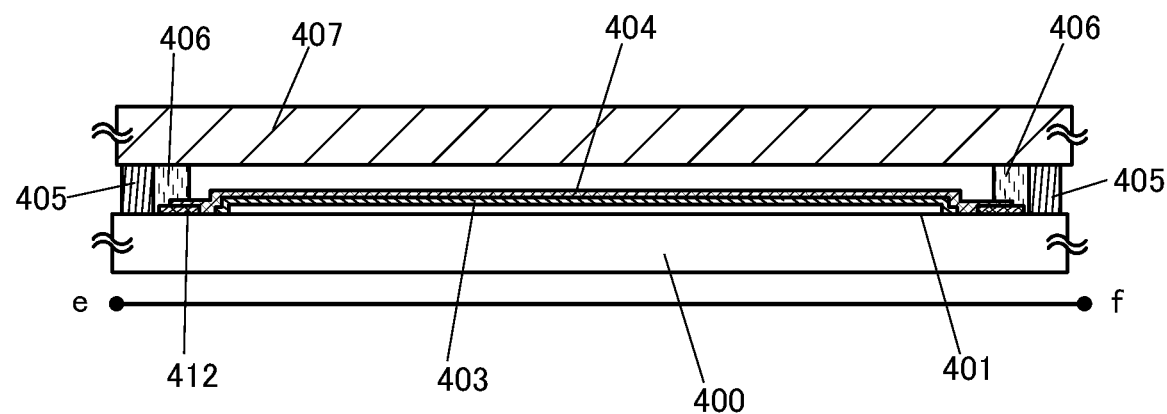
FIGS. 15A and 15B illustrate an electronic device of an embodiment.
Figure 15B:
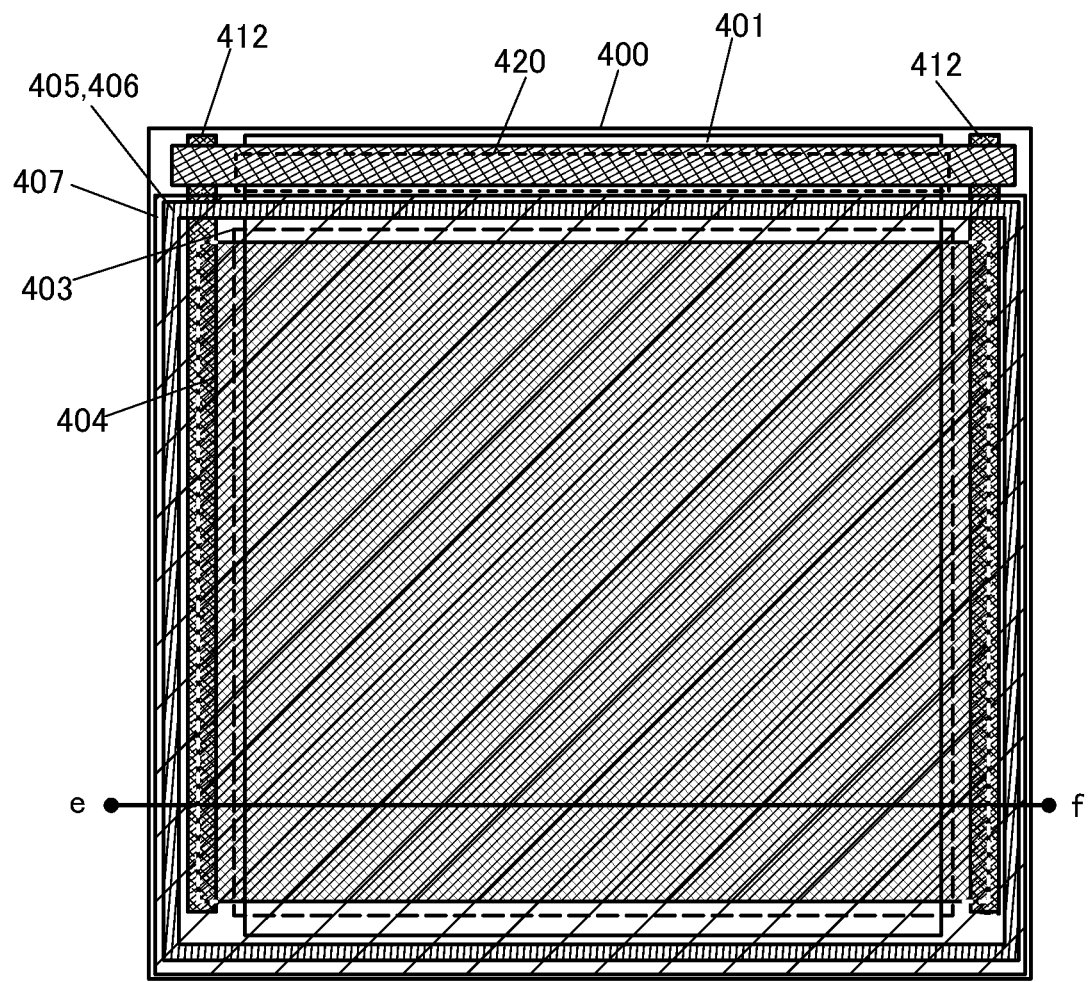

In this embodiment, a structure in which the light-emitting device described in Embodiment 2 is used in a lighting device will be described with reference to FIGS. 15A and 15B. FIG. 15A illustrates a cross section taken along the line e-f in a top view of the lighting device in FIG. 15B.

In the lighting device in this embodiment, the first electrode 401 is formed over a substrate 400 that is a support and has a light-transmitting property. The first electrode 401 corresponds to the first electrode 101 in Embodiment 2. When light is extracted from the first electrode 401 side, the first electrode 401 is formed using a material having a light-transmitting property.

A pad 412 for applying voltage to the second electrode 404 is provided over the substrate 400.

An EL layer 403 is formed over the first electrode 401. The structure of the EL layer 403 corresponds to the structure of the EL layer 103 in Embodiment 2. Refer to the corresponding description for these structures.

The second electrode 404 is formed to cover the EL layer 403. The second electrode 404 corresponds to the second electrode 102 in Embodiment 2. The second electrode 404 is formed using a material having high reflectance when light is extracted from the first electrode 401 side. The second electrode 404 is connected to the pad 412 so that voltage is applied to the second electrode 404.

As described above, the lighting device described in this embodiment includes a light-emitting device including the first electrode 401, the EL layer 403, and the second electrode 404. Since the light-emitting device has high emission efficiency, the lighting device in this embodiment can have low power consumption.

The substrate 400 provided with the light-emitting device having the above structure and a sealing substrate 407 are fixed and sealed with sealing materials 405 and 406, whereby the lighting device is completed. It is possible to use only either the sealing material 405 or the sealing material 406. In addition, the inner sealing material 406 (not illustrated in FIG. 15B) can be mixed with a desiccant that enables moisture to be adsorbed, increasing the reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

Embodiment 7

Figure 16:
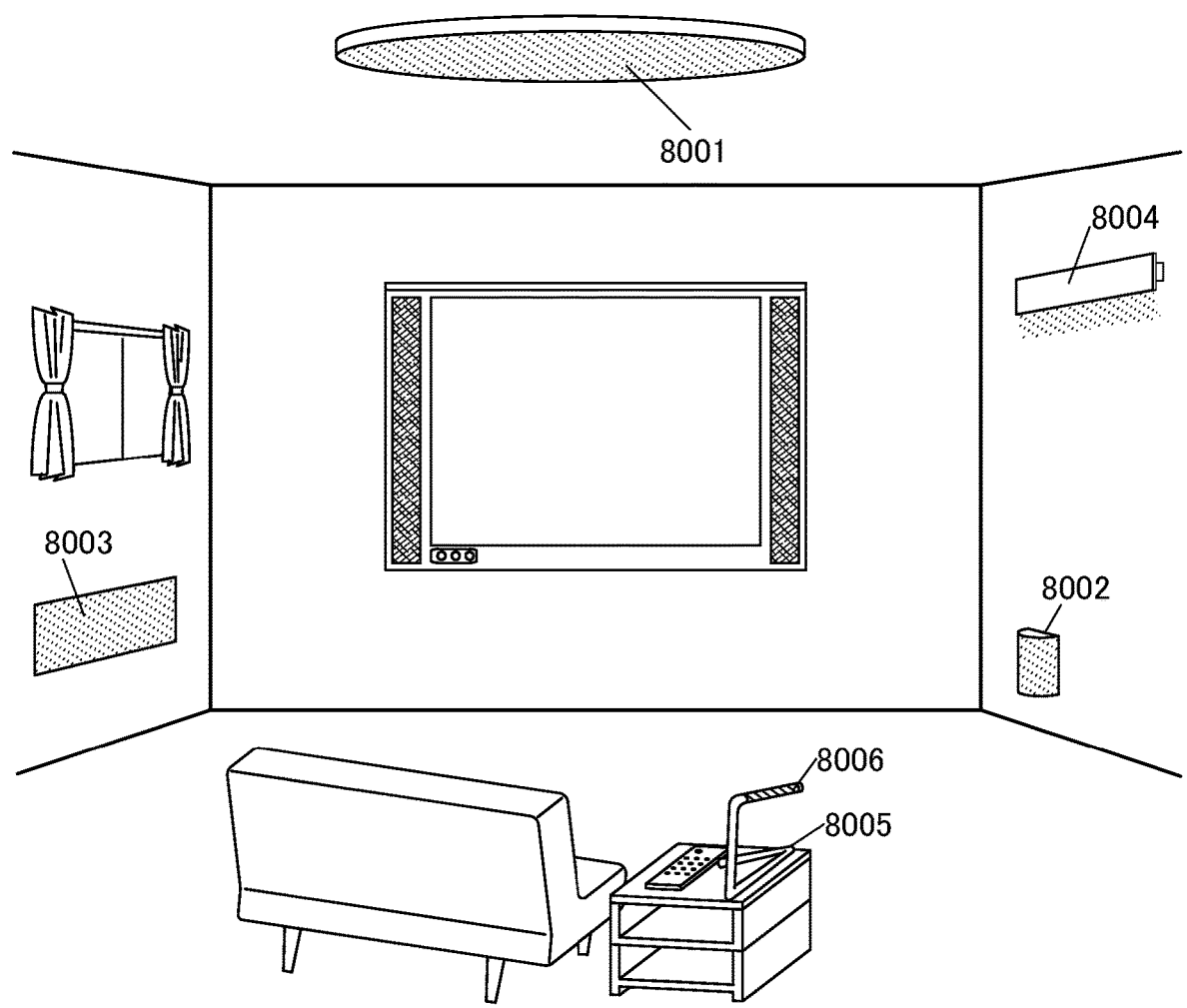
FIG. 16 illustrates electronic devices of an embodiment.

In this embodiment, application examples of lighting devices fabricated using the light-emitting apparatus of one embodiment of the present invention or the light-emitting device, which is part of the light-emitting apparatus, will be described with reference to FIG. 16.

A ceiling light 8001 can be used as an indoor lighting device. Examples of the ceiling light 8001 include a direct-mount light and an embedded light. Such lighting devices are fabricated using the light-emitting apparatus and a housing or a cover in combination. Application to a cord pendant light (light that is suspended from a ceiling by a cord) is also possible.

A foot light 8002 lights a floor so that safety on the floor can be improved. For example, it can be effectively used in a bedroom, on a staircase, or on a passage. In that case, the size and shape of the foot light can be changed in accordance with the dimensions and structure of a room. The foot light can be a stationary lighting device fabricated using the light-emitting apparatus and a support in combination.

A sheet-like lighting 8003 is a thin sheet-like lighting device. The sheet-like lighting, which is attached to a wall when used, is space-saving and thus can be used for a wide variety of uses. Furthermore, the area of the sheet-like lighting can be easily increased. The sheet-like lighting can also be used on a wall or a housing that has a curved surface.

A lighting device 8004 in which the direction of light from a light source is controlled to be only a desired direction can be used.

A desk lamp 8005 includes a light source 8006. As the light source 8006, the light-emitting apparatus of one embodiment of the present invention or the light-emitting device, which is part of the light-emitting apparatus, can be used.

Besides the above examples, when the light-emitting apparatus of one embodiment of the present invention or the light-emitting device, which is part of the light-emitting apparatus, is used as part of furniture in a room, a lighting device that functions as the furniture can be obtained.

As described above, a variety of lighting devices that include the light-emitting apparatus can be obtained. Note that these lighting devices are also embodiments of the present invention.

The structures described in this embodiment can be used in appropriate combination with any of the structures described in the other embodiments.

Embodiment 8

In this embodiment, a light-emitting device and a light-receiving device that can be used in a display device of one embodiment of the present invention will be described with reference to FIGS. 17A to 17C.

Figure 17A:
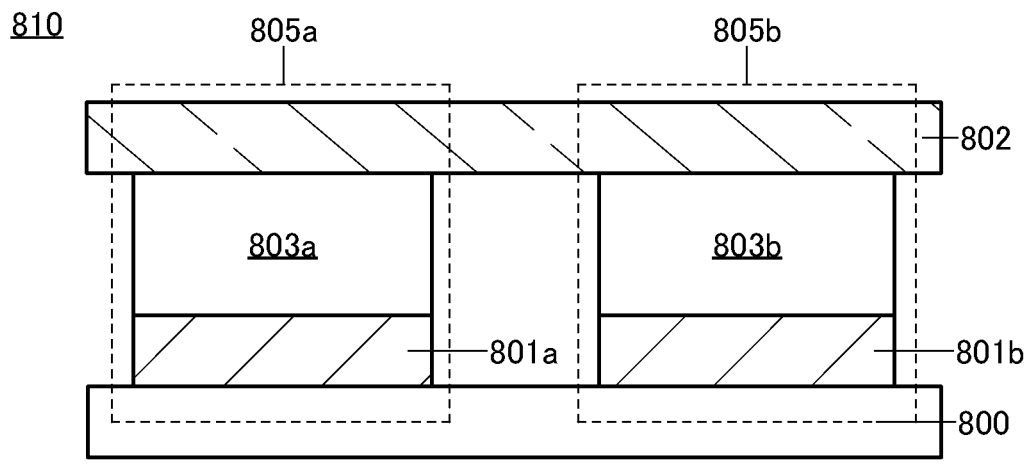
FIGS. 17A to 17C illustrate a light-emitting device and a light-receiving device of an embodiment.

FIG. 17A is a schematic cross-sectional view of a light-emitting device 805*a* and a light-receiving device 805*b* included in a display device 810 of one embodiment of the present invention.

The light-emitting device 805*a* has a function of emitting light (hereinafter, also referred to as a light-emitting function). The light-emitting device 805*a* includes an electrode 801*a*, an EL layer 803*a*, and an electrode 802. The light-emitting device 805*a* is preferably a light-emitting device utilizing organic EL (an organic EL device) described in Embodiment 2. Thus, the EL layer 803*a* interposed between the electrode 801*a* and the electrode 802 includes at least a light-emitting layer. The light-emitting layer contains a light-emitting substance. The EL layer 803*a* emits light when voltage is applied between the electrode 801*a* and the electrode 802. The EL layer 803*a* may include any of a variety of layers such as a hole-injection layer, a hole-transport layer, an electron-transport layer, an electron-injection layer, a carrier-blocking (hole-blocking or electron-blocking) layer, and a charge-generation layer, in addition to the light-emitting layer. Note that any of the organic compounds of one embodiment of the present invention can be used for the EL layer 803*a* in the light-emitting device 805*a*.

The light-receiving device 805b has a function of sensing light (hereinafter, also referred to as a light-receiving function). As the light-receiving device 805b, a PN photodiode or a PIN photodiode can be used, for example. The light-receiving device 805b includes an electrode 801b, a light-receiving layer 803b, and the electrode 802. Thus, the light-receiving layer 803b interposed between the electrode 801b and the electrode 802 includes at least an active layer. The light-receiving device 805b functions as a photoelectric conversion device, where electric charge is generated with light incident on the light-receiving layer 803b and can be extracted as current. At this time, voltage may be applied between the electrode 801b and the electrode 802. The amount of generated electric charge depends on the amount of light incident on the light-receiving layer 803b.

The light-receiving device 805b has a function of sensing visible light. The light-receiving device 805b has sensitivity to visible light. The light-receiving device 805b further preferably has a function of sensing visible light and infrared light. The light-receiving device 805b preferably has sensitivity to visible light and infrared light.

In this specification and the like, a blue (B) wavelength range is greater than or equal to 400 nm and less than 490 nm, and blue (B) light has at least one emission spectrum peak in the wavelength range. A green (G) wavelength range is greater than or equal to 490 nm and less than 580 nm, and green (G) light has at least one emission spectrum peak in the wavelength range. A red (R) wavelength range is greater than or equal to 580 nm and less than 700 nm, and red (R) light has at least one emission spectrum peak in the wavelength range. In this specification and the like, a visible light wavelength range is greater than or equal to 400 nm and less than 700 nm, and visible light has at least one emission spectrum peak in the wavelength range. An infrared (IR) wavelength range is greater than or equal to 700 nm and less than 900 nm, and infrared (IR) light has at least one emission spectrum peak in the wavelength range.

The active layer in the light-receiving device 805b includes a semiconductor. Examples of the semiconductor include inorganic semiconductors such as silicon and organic semiconductors including organic compounds. As the light-receiving device 805b, an organic semiconductor device (or an organic photodiode) including an organic semiconductor in an active layer is preferably used. An organic photodiode, which is easily made thin, lightweight, and large in area and has a high degree of freedom for shape and design, can be used in a variety of display devices. An organic semiconductor is preferably used, in which case the EL layer 803a included in the light-emitting device 805a and the light-receiving layer 803b included in the light-receiving device 805b can be formed by the same method (e.g., a vacuum evaporation method) with the same manufacturing apparatus. Note that any of the organic compounds of one embodiment of the present invention can be used for the light-receiving layer 803b in the light-receiving device 805b.

In the display device of one embodiment of the present invention, an organic EL device and an organic photodiode can be suitably used as the light-emitting device 805a and the light-receiving device 805b, respectively. The organic EL device and the organic photodiode can be formed over one substrate. Thus, the organic photodiode can be incorporated into the display device including the organic EL device. A display device of one embodiment of the present invention has one or both of an image capturing function and a sensing function in addition to a function of displaying an image.

The electrode 801a and the electrode 801b are provided on the same plane. In FIG. 17A, the electrodes 801a and 801b are provided over a substrate 800. The electrodes 801a and 801b can be formed by processing a conductive film formed over the substrate 800 into an island shape, for example. In other words, the electrodes 801a and 801b can be formed through the same process.

As the substrate 800, a substrate having heat resistance high enough to withstand the formation of the light-emitting device 805a and the light-receiving device 805b can be used. When an insulating substrate is used, a glass substrate, a quartz substrate, a sapphire substrate, a ceramic substrate, an organic resin substrate, or the like can be used as the substrate 800. Alternatively, a semiconductor substrate can be used. For example, a single crystal semiconductor substrate or a polycrystalline semiconductor substrate of silicon, silicon carbide, or the like; a compound semiconductor substrate of silicon germanium or the like; an SOI substrate; or the like can be used.

As the substrate 800, it is particularly preferable to use the insulating substrate or the semiconductor substrate over which a semiconductor circuit including a semiconductor element such as a transistor is formed. The semiconductor circuit preferably forms a pixel circuit, a gate line driver circuit (a gate driver), a source line driver circuit (a source driver), or the like. In addition to the above, an arithmetic circuit, a memory circuit, or the like may be formed.

The electrode 802 is formed of a layer shared by the light-emitting device 805a and the light-receiving device 805b. As the electrode through which light enters or exits, a conductive film that transmits visible light and infrared light is used. As the electrode through which light neither enters nor exits, a conductive film that reflects visible light and infrared light is preferably used.

The electrode 802 in the display device of one embodiment of the present invention functions as one of the electrodes in each of the light-emitting device 805a and the light-receiving device 805b.

Figure 17B:
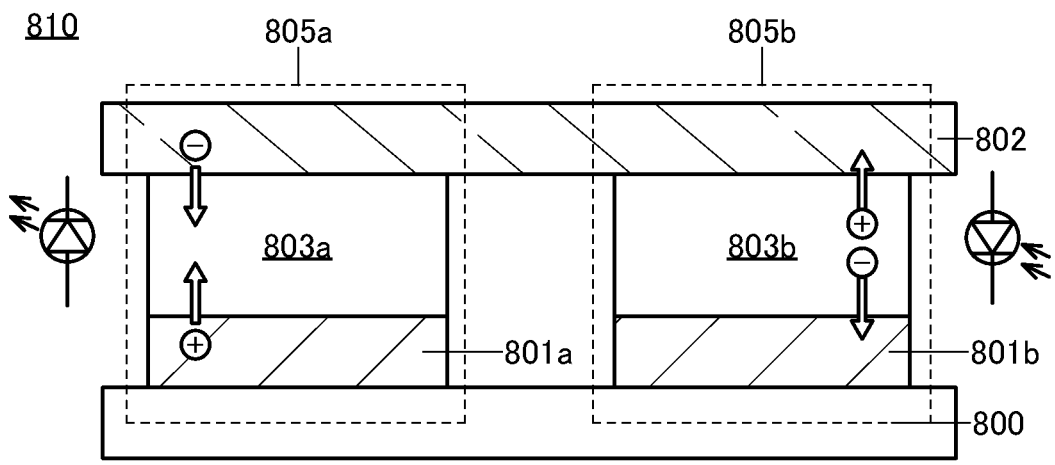

FIG. 17B illustrates the case where the electrode 801a of the light-emitting device 805a has a higher potential than the electrode 802. In this case, the electrode 801a functions as an anode and the electrode 802 functions as a cathode in the light-emitting device 805a. The electrode 801b of the light-receiving device 805b has a lower potential than the electrode 802. For easy understanding of the direction of current flow, FIG. 17B illustrates a circuit symbol of a light-emitting diode on the left of the light-emitting device 805a and a circuit symbol of a photodiode on the right of the light-receiving device 805b. The flow directions of carriers (electrons and holes) in each device are also schematically indicated by arrows.

In the structure illustrated in FIG. 17B, when a first potential is supplied to the electrode 801a through a first wiring, a second potential is supplied to the electrode 802 through a second wiring, and a third potential is supplied to the electrode 801a through a third wiring in the light-emitting device 805*a*, the following relationship is satisfied: the first potential>the second potential>the third potential.

Figure 17C:
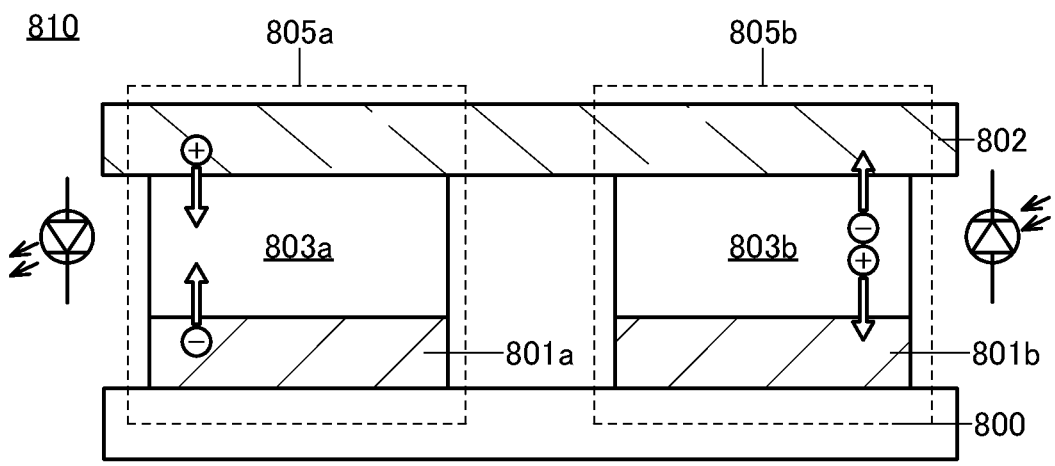

FIG. 17C illustrates the case where the electrode 801*a* of the light-emitting device 805*a* has a lower potential than the electrode 802. In this case, the electrode 801*a* functions as a cathode and the electrode 802 functions as an anode in the light-emitting device 805*a*. The electrode 801*b* of the light-receiving device 805*b* has a lower potential than the electrode 802 and a higher potential than the electrode 801*a*. For easy understanding of the direction of current flow, FIG. 17C illustrates a circuit symbol of a light-emitting diode on the left of the light-emitting device 805*a* and a circuit symbol of a photodiode on the right of the light-receiving device 805*b*. The flow directions of carriers (electrons and holes) in each device are also schematically indicated by arrows.

In the structure illustrated in FIG. 17C, when a first potential is supplied to the electrode 801*a* through a first wiring, a second potential is supplied to the electrode 802 through a second wiring, and a third potential is supplied to the electrode 801*a* through a third wiring in the light-emitting device 805*a*, the following relationship is satisfied: the second potential>the third potential>the first potential.

The resolution of the light-receiving device 805*b* described in this embodiment can be 100 ppi or more, preferably 200 ppi or more, further preferably 300 ppi or more, still further preferably 400 ppi or more, and yet still further preferably 500 ppi or more, and 2000 ppi or less, 1000 ppi or less, or 600 ppi or less, for example. In particular, when the resolution of the light-receiving device 805*b* is 200 ppi or more and 600 ppi or less, preferably 300 ppi or more and 600 ppi or less, the display device of one embodiment of the present invention can be suitably used for image capturing of fingerprints. In fingerprint authentication with the display device of one embodiment of the present invention, the increased resolution of the light-receiving device 805*b* enables, for example, high-accuracy extraction of the minutiae of fingerprints; thus, the accuracy of the fingerprint authentication can be increased. The resolution is preferably 500 ppi or more, in which case the authentication conforms to the standard by the National Institute of Standards and Technology (NIST) or the like. On the assumption that the resolution of the light-receiving device is 500 ppi, the size of each pixel is 50.8 m, which is adequate for image capturing of a fingerprint ridge distance (typically, greater than or equal to 300 m and less than or equal to 500 m).

The structures described in this embodiment can be used in appropriate combination with any of the structures described in the other embodiments.

Example 1

Synthesis Example 1

In this example, a method for synthesizing N-(3',5'-di-tert-butyl-1,1'-biphenyl-4-yl)-bis(9,9-dimethyl-9H-fluoren)-2,2'-amine (abbreviation: mmtBuBiFF), which is the organic compound represented by Structural Formula (100) in Embodiment 1, is described. The structure of mmtBuBiFF is shown below.

[Chemical Formula 18]

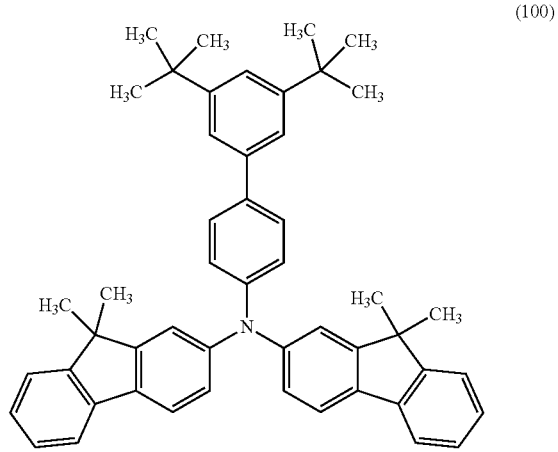

(100)

Step 1: Synthesis of 3',5'-di-tert-butyl-4-chloro-1,1'-biphenyl

In a three-neck flask were put 30.0 g (114 mmol) of 3,5-di-tert-butyl-1-bromobenzene, 19.2 g (123 mmol) of 4-chlorophenylboronic acid, 46.1 g (334 mmol) of potassium carbonate, 550 mL of toluene, 140 mL of ethanol, and 160 mL of water. The mixture was degassed under reduced pressure, and then the air in the flask was replaced with nitrogen. To this mixture, 251 mg (1.12 mmol) of palladium acetate and 695 mg (2.28 mmol) of tris(2-methylphenyl)phosphine were added, and the mixture was heated and refluxed at 90° C. for approximately 5 hours. After that, the temperature of the flask was lowered to room temperature, and the mixture was separated into an organic layer and an aqueous layer. Magnesium sulfate was added to the organic layer for drying, and then a solution separated by filtration was concentrated to give a condensed brown solution. The obtained solution was purified by silica gel column chromatography. The obtained solution was concentrated and dried for hardening. After that, hexane was added for recrystallization. The mixed solution in which a white solid was precipitated was cooled with ice and then filtrated. The obtained solid was dried at approximately 100° C. in a vacuum, whereby 29.6 g of a target white solid was obtained in a yield of 88%. The synthesis scheme of Step 1 is shown below.

[Chemical Formula 19]

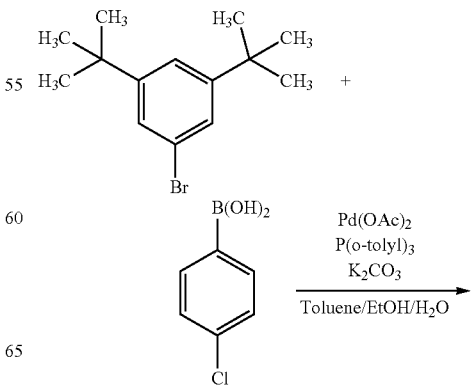

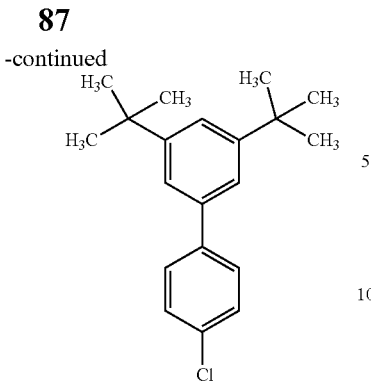

Step 2: Synthesis of mmtBuBiFF

In a three-neck flask were put 30.4 g (75.7 mmol) of bis(9,9-dimethyl-9H-fluoren-2-yl)amine, 22.8 g (75.8 mmol) of 3',5'-di-tert-butyl-4-chloro-1,1'-biphenyl, 21.9 g (228 mmol) of sodium-tert-butoxide, and 380 mL of xylene. The mixture was degassed under reduced pressure, and then the air in the flask was replaced with nitrogen. The mixture was stirred while being heated to approximately 60° C. Then, 283 mg (0.773 mmol) of allylpalladium(II) chloride dimer (abbreviation: (AllylPdCl)$_2$) and 1.05 g (2.98 mmol) of di-tert-butyl(1-methyl-2,2-diphenylcyclopropyl)phosphine (abbreviation: cBRIDP (registered trademark)) were added, and the mixture was heated at 100° C. for approximately 5 hours. After that, the temperature of the mixture was lowered to approximately 60° C., and approximately 2 mL of water was added to the mixture, so that a solid was precipitated. The precipitated solid was separated by filtration to obtain a solution. The filtrate was concentrated, and the obtained solution was purified by silica gel column chromatography. The obtained solution was concentrated to give a condensed toluene solution. The toluene solution was dropped into ethanol for reprecipitation. The precipitate was filtrated at approximately 10° C. and the obtained solid was dried at approximately 100° C. under reduced pressure, whereby 44.2 g of a target white solid was obtained in a yield of 88%. The synthesis scheme of Step 2 is shown below.

[Chemical Formula 20]

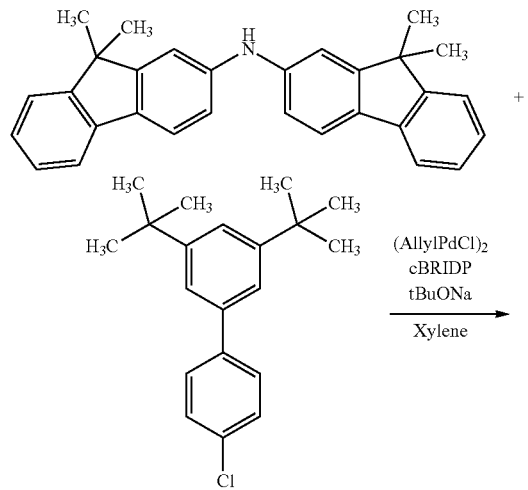

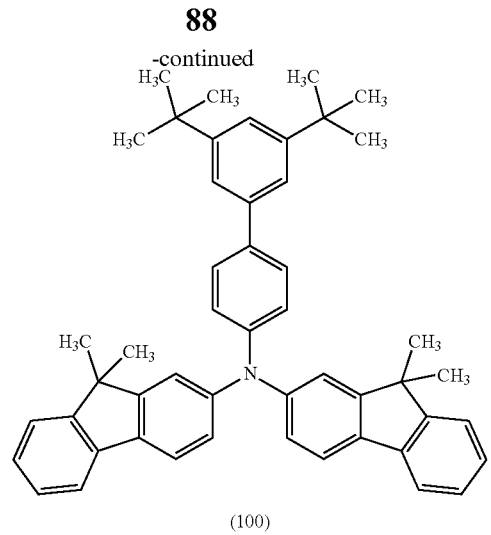

Analysis results by nuclear magnetic resonance ($^1$H-NMR) spectroscopy of the white solid obtained in Step 2 are shown below. The results show that N-(3',5'-di-tert-butyl-1,1'-biphenyl-4-yl)-bis(9,9-dimethyl-9H-fluoren)-2,2'-amine (abbreviation: mmtBuBiFF) was synthesized in this synthesis example.

$^1$H-NMR (500 MHz, DMSO-d$_6$): δ=7.75 (t, 4H, J=7.8 Hz), 7.62 (d, 2H, J=9.0 Hz), 7.51 (d, 2H, J=5.0 Hz), 7.42 (s, 2H), 7.38 (s, 1H), 7.34-7.25 (m, 6H), 7.18 (d, 2H, J=8.0 Hz, 2.0 Hz), 7.03 (dd, 2H, J=8.0 Hz, 2.0 Hz), 1.37 (s, 12H), 1.34 (s, 18H).

Then, 44.0 g of the obtained solid was purified by a train sublimation method. The purification by sublimation was conducted by heating at 275° C. under a pressure of 3.02 Pa with an argon flow rate of 12.0 mL/min. After the purification by sublimation, 41.1 g of a pale yellowish white solid was obtained at a collection rate of 94%.

Figure 18:
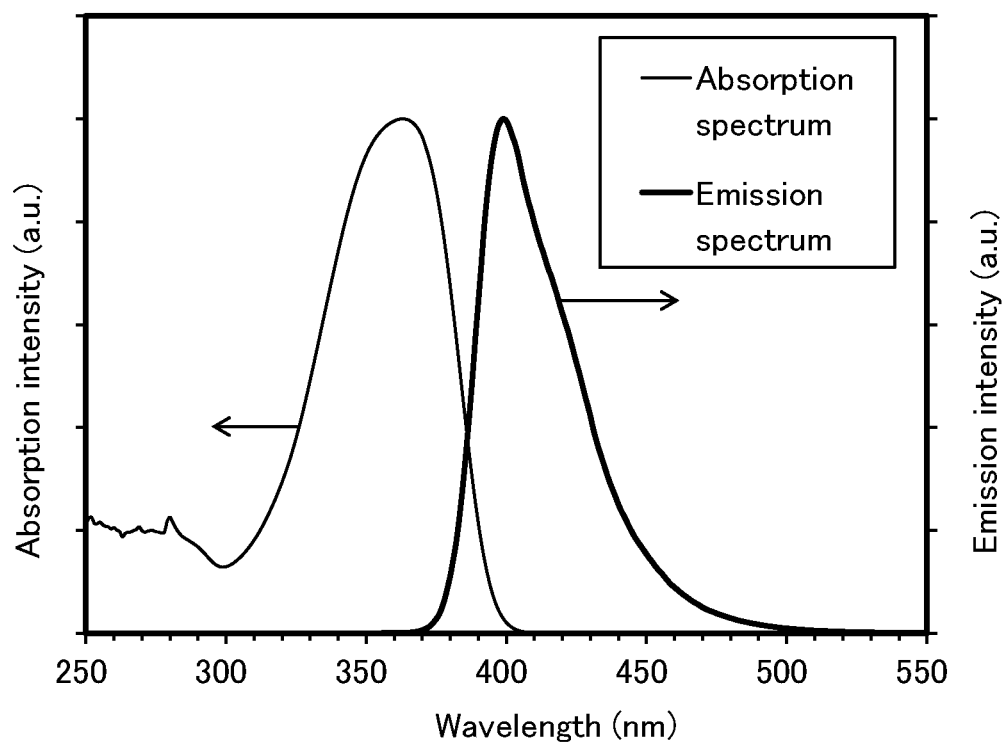
FIG. 18 shows an absorption spectrum and an emission spectrum of 20 mmtBuBiFF in a toluene solution.

Next, an ultraviolet-visible absorption spectrum (hereinafter, simply referred to as an absorption spectrum) and an emission spectrum of mmtBuBiFF in a toluene solution were measured. The absorption spectrum was measured at room temperature with an ultraviolet-visible light spectrophotometer (V-550, produced by JASCO Corporation), and the emission spectrum was measured at room temperature with a fluorescence spectrophotometer (FS920, produced by Hamamatsu Photonics K.K.). A quartz cell was used as the measurement cell. FIG. 18 shows measurement results of the absorption spectrum and the emission spectrum. The horizontal axis represents the wavelength and the vertical axes represent the absorption intensity and the emission intensity. The absorption intensity shown in FIG. 18 is a result obtained by subtraction of an absorption spectrum of only toluene in a quartz cell from the measured absorption spectrum of the toluene solution in the quartz cell.

As shown in FIG. 18, mmtBuBiFF had an emission peak at 399 nm.

Next, mmtBuBiFF was subjected to mass spectrometry (MS) analysis by liquid chromatography-mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBu-BiFF in an organic solvent at an arbitrary concentration, and the injection amount was 5.0 µL.

By a parallel reaction monitoring (PRM) method, MS/MS measurement of m/z=665.40 corresponding to the exact mass of mmtBuBiFF was performed. For setting of the PRM, the mass range of a target ion was set to m z=665.40±2.0 (isolation window=4) and detection was performed in a positive mode. The measurement was performed with energy (normalized collision energy: NCE) for accelerating a target ion in a collision cell set to 60. The MS spectrum obtained by the MS/MS measurement is shown in FIG. 19.

Figure 19:
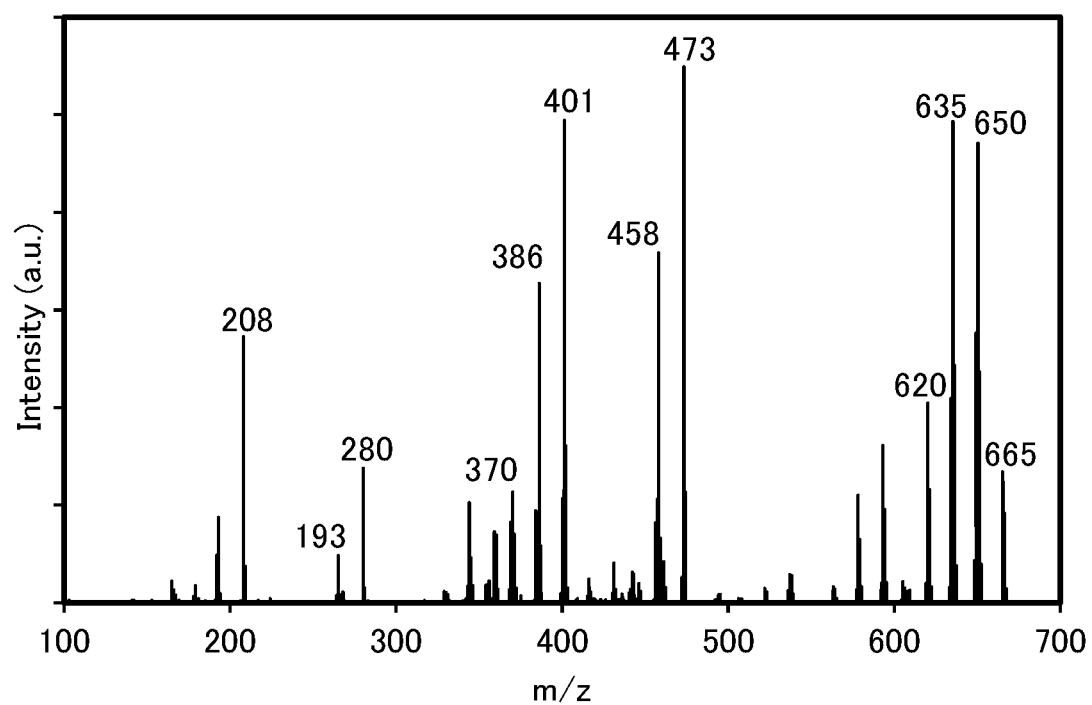
FIG. 19 shows an MS spectrum of mmtBuBiFF.

The results in FIG. 19 show that, owing to the presence and absence of hydrogen ions and isotopes, precursor ions of mmtBuBiFF were mainly detected at around m/z=665, and product ions of mmtBuBiFF were detected at around m/z=473 and around m/z=401.

Note that the product ion detected at around m/z=473 is presumed to be in the state where one dimethylfluorenyl group is eliminated from mmtBuBiFF, which means that mmtBuBiFF has a 9,9-dimethylfluorenyl group.

The product ion detected at around m/z=401 is presumed to be in the state where one 3,5-di-tert-butyl-1,1'-biphenyl group is eliminated from mmtBuBiFF, which means that mmtBuBiFF has a 3,5-di-tert-butyl-1,1'-biphenyl group.

Figure 20:
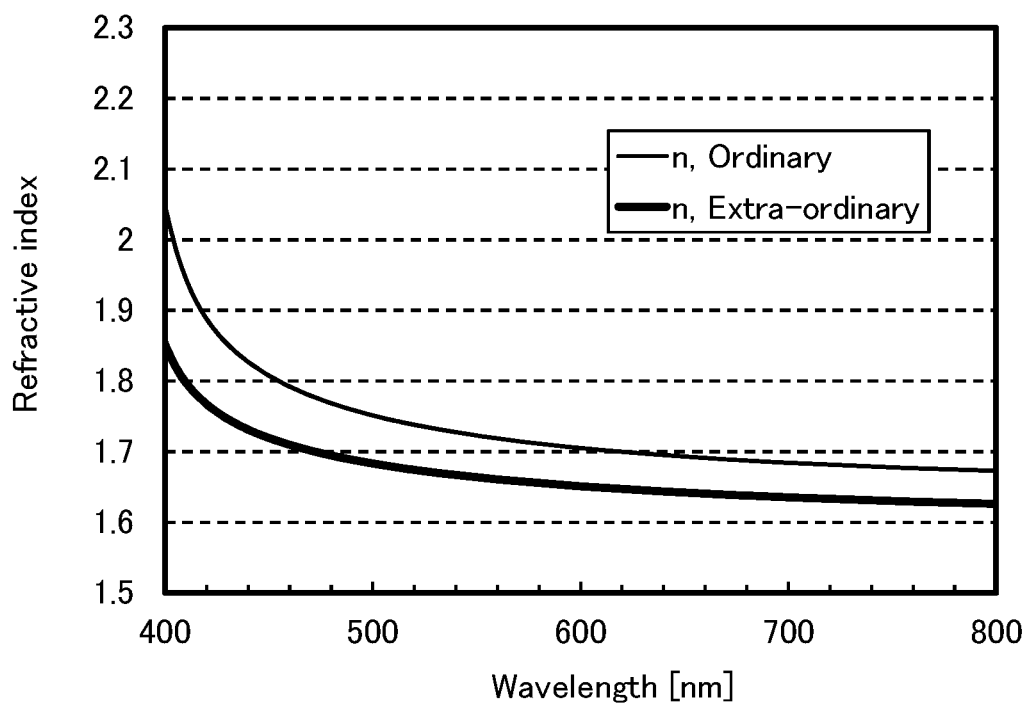
FIG. 20 shows measurement data of refractive indices of mmtBuBiFF.

FIG. 20 shows the results of measuring the refractive indices of mmtBuBiFF with a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index for an ordinary ray, n, Ordinary, and a refractive index for an extraordinary ray, n, Extra-ordinary, are shown in FIG. 20.

FIG. 20 reveals that mmtBuBiFF is a material with a low refractive index; the ordinary refractive index at a wavelength of 465 nm is 1.785, the ordinary refractive index at a wavelength of 520 nm is 1.74, and the ordinary refractive index at a wavelength of 633 nm is 1.70.

Next, Tg of mmtBuBiFF was measured. Note that Tg was measured with a differential scanning calorimeter (Pyris 1 DSC produced by PerkinElmer Japan Co., Ltd.) in a state where a powder was put on an aluminum cell. As a result, Tg of mmtBuBiFF was 122° C.

Next, the HOMO level of mmtBuBiFF was measured. The HOMO level was obtained through cyclic voltammetry (CV) measurement. An electrochemical analyzer (ALS model 600A or 600C, produced by BAS Inc.) was used for the measurement. As a result, the HOMO level of mmtBu-BiFF was −5.33 eV.

In addition, GSP of mmtBuBiFF was obtained. Here, a method for obtaining GSP of an organic compound is described.

A phenomenon in which a surface potential of an evaporated film increases in proportion to a film thickness is called the giant surface potential as described above. In general, a slope of a plot of a surface potential of an evaporated film in the thickness direction by Kelvin probe measurement is assumed as the level of the giant surface potential, that is, GSP (mV/nm); in the case where two different layers are stacked, a change in the density of polarization charges (mC/m$^2$) accumulated at the interface, which is in association with GSP, can be utilized to estimate GSP.

The article "Spontaneous Orientation Polarization of Polar Molecules and Interface Properties of Organic Electronic Devices", Journal of the Vacuum Society of Japan, 2015, Vol. 58, No. 3, which is written by Y. Noguchi et al., discloses that the following formulae hold when current is made to flow through a stack of organic thin films (a thin film 1 positioned on the anode side and a thin film 2 positioned on the cathode side) with different kinds of spontaneous polarization.

[Formula 1]

$$\sigma_{if} = \frac{Q_{if}}{S} = (V_i - V_{bi})\frac{\varepsilon_2}{d_2} \quad (1)$$

[Formula 2]

$$\sigma_{if} = P_1 - P_2 = \frac{\varepsilon_1 V_1}{d_1} - \frac{\varepsilon_2 V_2}{d_2} \quad (2)$$

In Formula (1), $\sigma_{if}$ is a polarization charge density, $V_i$ is a hole-injection voltage, $V_{bi}$ is a threshold voltage, $d_2$ is a thickness of the thin film 2, and $\varepsilon_2$ is a dielectric constant of the thin film 2. Note that $V_i$ and $V_{bi}$ can be estimated from the capacity-voltage characteristics of a device. The square of an ordinary refractive index $n_o$(633 nm) can be used as the dielectric constant. As described above, according to Formula (1), the polarization charge density $\sigma_{if}$ can be calculated using $V_i$ and $V_{bi}$ estimated from the capacity-voltage characteristics, the dielectric constant $\varepsilon_2$ of the thin film 2 calculated from the refractive index, and the thickness $d_2$ of the thin film 2.

Next, in Formula (2), $\sigma_{if}$ is a polarization charge density, $P_n$ is GSP of a thin film n, and $\varepsilon_n$ is a dielectric constant of the thin film n. Since the polarization charge density $\sigma_{if}$ can be obtained from Formula (1), the use of a substance with known GSP for the thin film 2 enables GSP of the thin film 1 to be estimated.

In this specification, Alq$_3$ whose GSP is known to be 48 (mV/nm) is used for the thin film 2, and GSP of each thin film is obtained.

Note that in the case where the thin film 1 or the thin film 2 contains a plurality of organic compounds, GSP of the major organic compound (e.g., the organic compound contained in the largest proportion) can be regarded as "GSP of an organic compound in a layer". Alternatively, in the case where the thin film 1 or the thin film 2 contains a plurality of organic compounds, GSP and contents of the organic compounds are calculated, and a weighted average (GSP_ave) may be defined as "GSP of an organic compound in a layer".

The results obtained in the above manner show that GSP of mmtBuBiFF is 39.5 mV/nm.

Example 2

Synthesis Example 2

In this example, a method for synthesizing N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmt-BuBiFF-02), which is the organic compound represented by Structural Formula (101) in Embodiment 1, is described. The structure of mmtBuBiFF-02 is shown below.

[Chemical Formula 21]

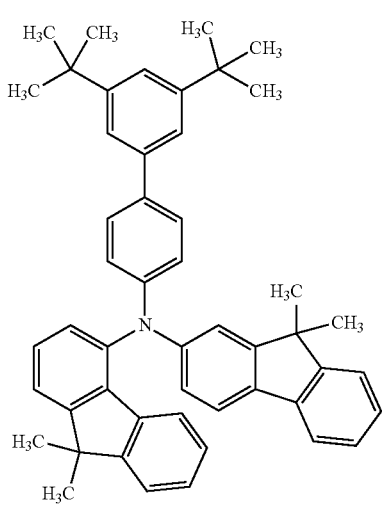

(101)

Step 1: Synthesis of 3',5'-di-tert-butyl-4-bromo-1,1'-biphenyl

In a three-neck flask were put 30.0 g (150 mmol) of 3,5-di-tert-butyl-benzeneboronic acid, 50.9 g (180 mmol) of 4-bromoiodobenzene, 62.2 g (450 mmol) of potassium carbonate, 500 mL of toluene, 125 mL of ethanol, and 225 mL of water. The mixture was degassed under reduced pressure, and then the air in the flask was replaced with nitrogen. To this mixture, 3.5 g (3.0 mmol) of tetrakis(triphenylphosphine)palladium was added, and the mixture was heated and refluxed at approximately 80° C. for approximately 5 hours. After that, the temperature of the flask was lowered to room temperature, and the mixture was separated into an organic layer and an aqueous layer. Magnesium sulfate was added to the organic layer for drying, followed in order by filtration and concentration, so that a brown solid was obtained. The obtained solid was purified by silica gel column chromatography. The obtained solution was concentrated and dried for hardening. After that, hexane was added for recrystallization. The mixed solution in which a white solid was precipitated was cooled with ice and then filtrated. The obtained solid was dried at approximately 100° C. in a vacuum, whereby 44.3 g of a target white solid was obtained in a yield of 86%. The synthesis scheme of Step 1 is shown below.

[Chemical Formula 22]

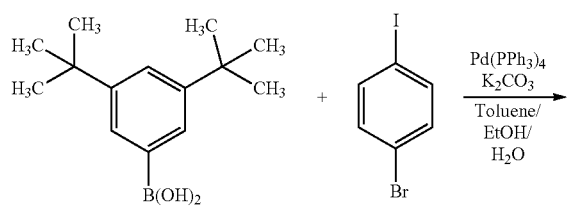

-continued

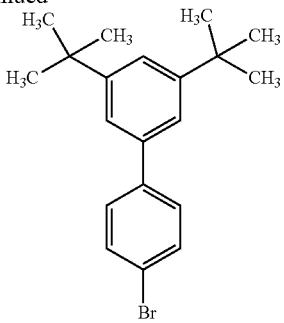

Step 2: Synthesis of N-(9,9-dimethyl-9H-fluoren-4-yl)-9,9-dimethyl-9H-fluoren-2-amine In a three-neck flask were put 4.22 g (20.2 mmol) of 2-amino-9,9-dimethyl-9H-fluorene, 5.08 g (18.6 mmol) of 4-bromo-9,9-dimethyl-9H-fluorene, 6.60 g (68.7 mmol) of sodium-tert-butoxide, and 90.0 mL of xylene. The mixture was degassed under reduced pressure, and then the air in the flask was replaced with nitrogen. The mixture was stirred while being heated to approximately 40° C. Then, 78.5 mg (0.215 mmol) of allylpalladium(II) chloride dimer (abbreviation: (AllylPdCl)$_2$) and 307 mg (0.748 mmol) of 2-dicyclohexylphosphino-2',6'-dimethoxybiphenyl (abbreviation: SPhos) were added, and the mixture was heated at 100° C. for approximately 6 hours. After that, the temperature of the flask was lowered to approximately 60° C., and approximately 1 mL of water was added to the mixture, so that a solid was precipitated. The precipitated solid was separated by filtration. The filtrate was concentrated, and the obtained solution was purified by silica gel column chromatography. The obtained solution was concentrated to give 7.50 g of a target reddish brown oily substance in a yield of 100%. The synthesis scheme of Step 2 is shown below.

[Chemical Formula 23]

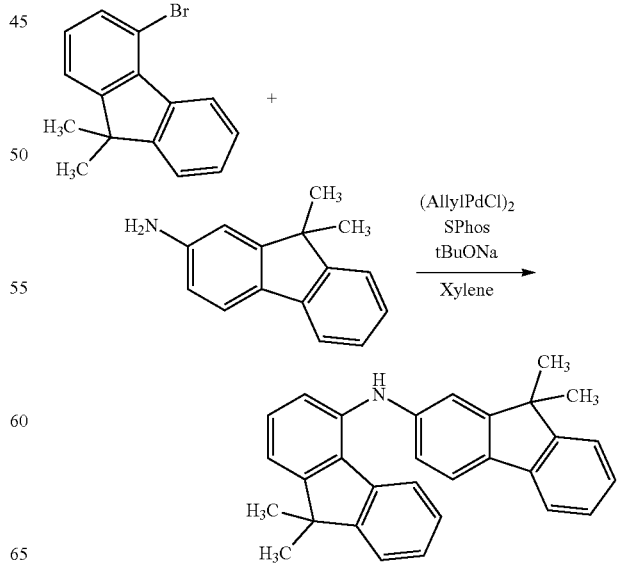

Step 3: Synthesis of mmtBuBiFF-02

In a three-neck flask were put 2.73 g (0.680 mmol) of N-(9,9-dimethyl-9H-fluoren-4-yl)-9,9-dimethyl-9H-fluoren-2-amine, 2.36 g (0.683 mmol) of 3',5'-di-tert-butyl-4-bromo-1,1'-biphenyl, 1.94 g (2.02 mmol) of sodium-tert-butoxide, and 37.0 mL of xylene. The mixture was degassed under reduced pressure, and then the air in the flask was replaced with nitrogen. Then, 29.0 mg (0.079 mmol) of allylpalladium(II) chloride dimer (abbreviation: (AllylPdCl)$_2$) and 88.2 mg (0.250 mmol) of di-tert-butyl(1-methyl-2,2-diphenylcyclopropyl)phosphine (abbreviation: cBRIDP (registered trademark)) were added, and the mixture was heated at 100° C. for approximately 6 hours. After that, the temperature of the mixture was lowered to approximately 60° C., and approximately 1 mL of water was added to the mixture, so that a solid was precipitated. The precipitated solid was separated by filtration. The filtrate was concentrated, and the obtained condensed solution was purified by silica gel column chromatography. The obtained solution was concentrated to give a condensed toluene solution. The toluene solution was dropped into ethanol for reprecipitation. The precipitate was filtrated at approximately 10° C. and the obtained solid was dried at approximately 100° C. under reduced pressure, whereby 3.21 g of a target white solid was obtained in a yield of 71%. The synthesis scheme of Step 3 is shown below.

[Chemical Formula 24]

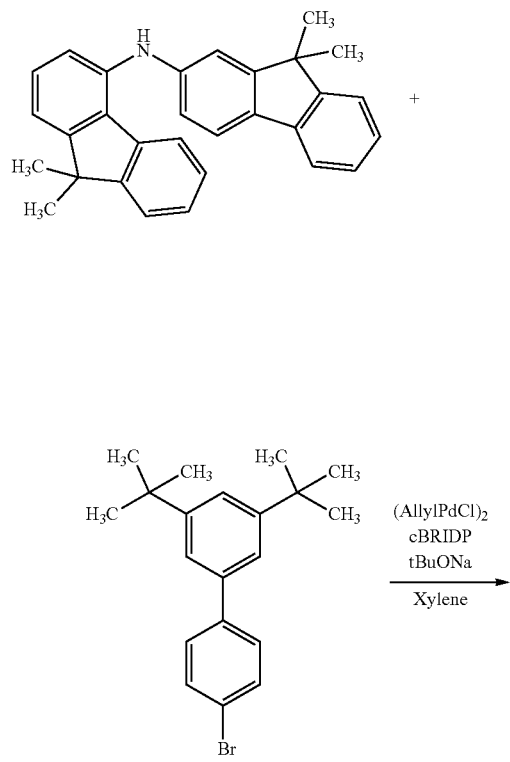

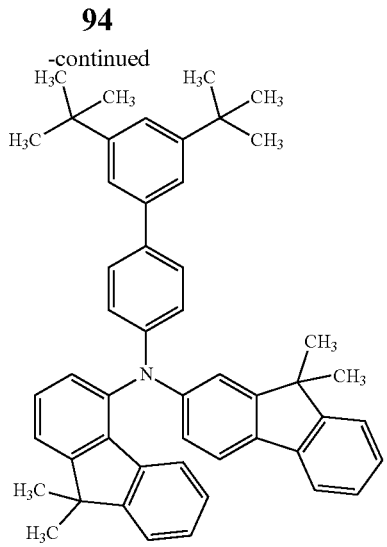

Analysis results by nuclear magnetic resonance ($^1$H-NMR) spectroscopy of the white solid obtained in Step 3 are shown below. The results show that N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02) was synthesized in this synthesis example.

$^1$H-NMR (500 MHz, DMSO-d$_6$): δ=7.66-7.62 (m, 3H), 7.58-7.52 (m, 4H), 7.47-7.43 (m, 2H), 7.37 (s, 2H), 7.33 (br, 2H), 7.28 (t, 1H, J=7.0 Hz), 7.22 (dt, 2H, J=7.3 Hz, 3.5 Hz), 7.13 (d, 1H, J=7.0 Hz), 6.89 (dd, 1H, J=8.0 Hz, 1.5 Hz), 1.50 (br, 6H), 1.36 (br, 6H), 1.31 (s, 18H), 1.28 (br, 6H).

Then, 3.19 g of the obtained solid was purified by a train sublimation method. The purification by sublimation was conducted by heating at 235° C. under a pressure of 2.54 Pa with an argon flow rate of 10.0 mL/min. After the purification by sublimation, 2.44 g of a pale yellowish white solid was obtained at a collection rate of 76%.

Figure 21:
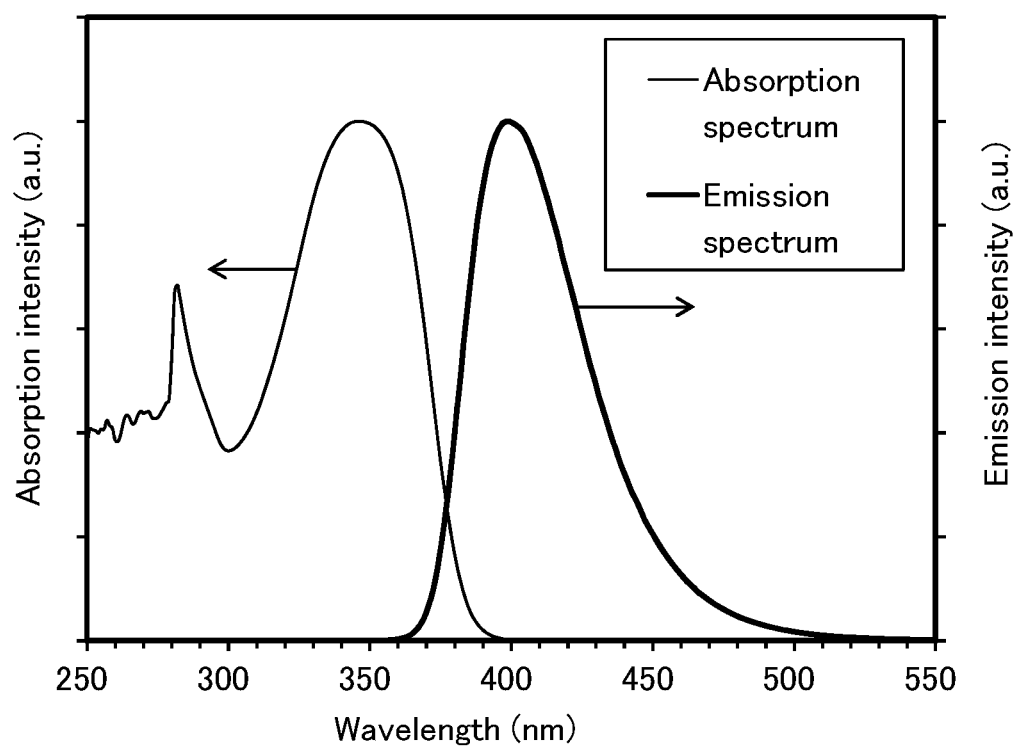
FIG. 21 shows an absorption spectrum and an emission spectrum of mmtBuBiFF-02 in a toluene solution.

Next, an ultraviolet-visible absorption spectrum (hereinafter, simply referred to as an absorption spectrum) and an emission spectrum of mmtBuBiFF-02 in a toluene solution were measured. The absorption spectrum was measured at room temperature with an ultraviolet-visible light spectrophotometer (V-550, produced by JASCO Corporation), and the emission spectrum was measured at room temperature with a fluorescence spectrophotometer (FS920, produced by Hamamatsu Photonics K.K.). A quartz cell was used as the measurement cell. FIG. 21 shows measurement results of the absorption spectrum and the emission spectrum. The horizontal axis represents the wavelength and the vertical axes represent the absorption intensity and the emission intensity. The absorption intensity shown in FIG. 21 is a result obtained by subtraction of an absorption spectrum of only toluene in a quartz cell from the measured absorption spectrum of the toluene solution in the quartz cell.

As shown in FIG. 21, the organic compound mmtBuBiFF-02 had an emission peak at 399 nm.

Next, the organic compound mmtBuBiFF-02 was subjected to mass spectrometry (MS) analysis by liquid chromatography-mass spectrometry (LC/MS).

In the LC/MS analysis, liquid chromatography (LC) separation was performed with UltiMate 3000 produced by Thermo Fisher Scientific K.K., and mass spectrometry (MS) was performed with Q Exactive produced by Thermo Fisher Scientific K.K.

In the LC separation, a given column was used at a column temperature of 40° C., and solution sending was performed in such a manner that an appropriate solvent was selected, the sample was prepared by dissolving mmtBu-BiFF-02 in an organic solvent at an arbitrary concentration, and the injection amount was 5.0 μL.

The MS/MS measurement of m z=665.40 corresponding to the exact mass of mmtBuBiFF-02 was performed by a PRM method. For setting of the PRM, the mass range of a target ion was set to m z=665.40±2.0 (isolation window=4) and detection was performed in a positive mode. The measurement was performed with energy (normalized collision energy: NCE) for accelerating a target ion in a collision cell set to 60. The MS spectrum obtained by the MS/MS measurement is shown in FIG. 22.

Figure 22:
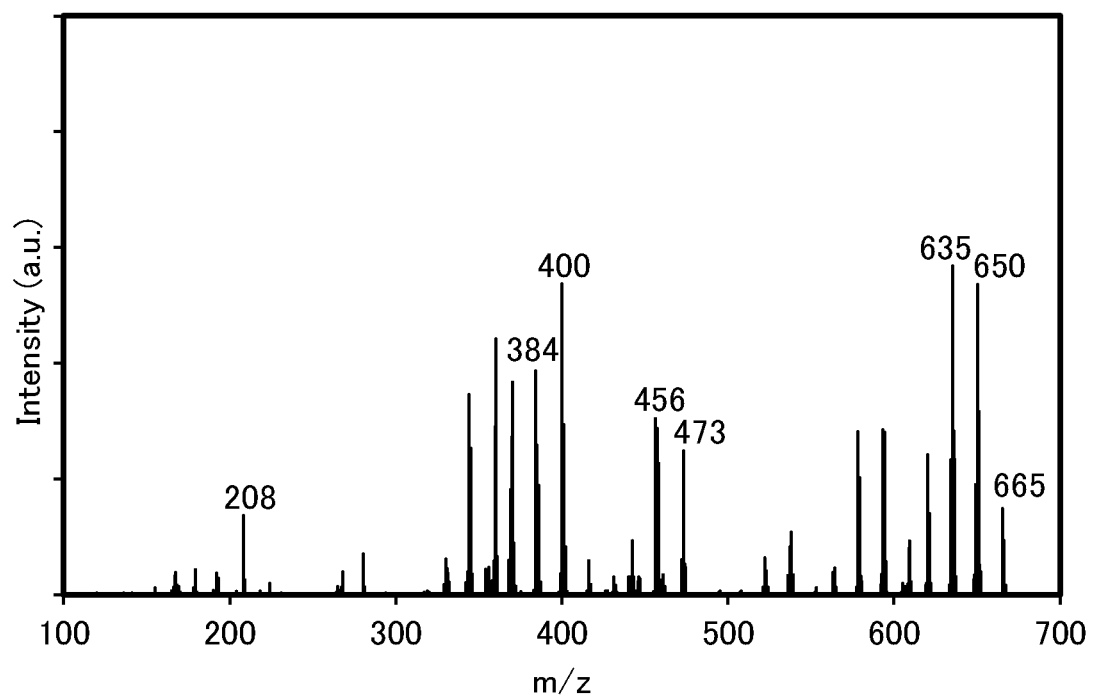
FIG. 22 shows an MS spectrum of mmtBuBiFF-02.

The results in FIG. 22 show that, owing to the presence and absence of hydrogen ions and isotopes, precursor ions of mmtBuBiFF-02 were mainly detected at around m/z=665, and product ions of mmtBuBiFF-02 were detected at around m/z=473 and around m/z=400.

Note that the product ion detected at around m/z=473 is presumed to be in the state where one dimethylfluorenyl group is eliminated from mmtBuBiFF-02, which means that mmtBuBiFF-02 has a 9,9-dimethylfluorenyl group.

The product ion detected at around m/z=400 is presumed to be in the state where one 3,5-di-tert-butyl-1,1'-biphenyl group is eliminated from mmtBuBiFF-02, which means that mmtBuBiFF-02 has a 3,5-di-tert-butyl-1,1'-biphenyl group.

Figure 23:
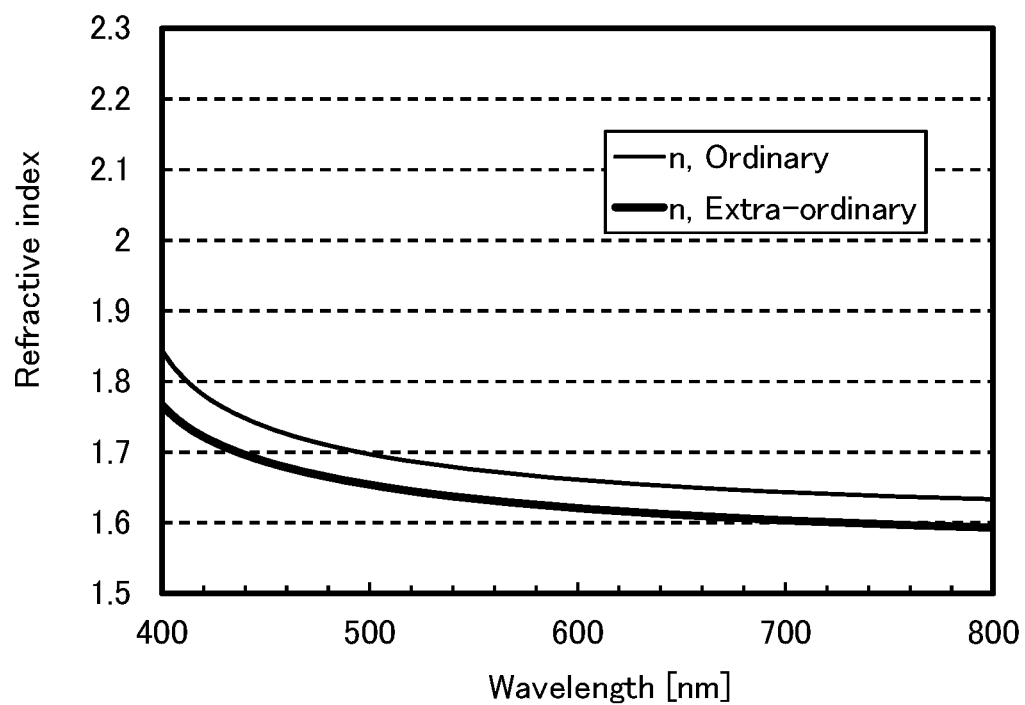
FIG. 23 shows measurement data of refractive indices of mmtBuBiFF-02.

FIG. 23 shows the results of measuring the refractive indices of mmtBuBiFF-02 with a spectroscopic ellipsometer (M-2000U, produced by J. A. Woollam Japan Corp.). A film used for the measurement was formed to a thickness of approximately 50 nm with the material of each layer over a quartz substrate by a vacuum evaporation method. Note that a refractive index for an ordinary ray, n, Ordinary, and a refractive index for an extraordinary ray, n, Extra-ordinary, are shown in FIG. 23.

FIG. 23 reveals that mmtBuBiFF-02 is a material with a low refractive index; the ordinary refractive index at a wavelength of 465 nm is 1.72, the ordinary refractive index at a wavelength of 520 nm is 1.69, and the ordinary refractive index at a wavelength of 633 nm is 1.65.

Next, Tg of mmtBuBiFF-02 was measured. Note that Tg was measured with a differential scanning calorimeter (Pyris 1 DSC produced by PerkinElmer Japan Co., Ltd.) in a state where a powder was put on an aluminum cell. As a result, Tg of mmtBuBiFF-02 was 122° C.

Next, the HOMO level of mmtBuBiFF-02 was measured. The HOMO level was obtained through cyclic voltammetry (CV) measurement. An electrochemical analyzer (ALS model 600A or 600C, produced by BAS Inc.) was used for the measurement. As a result, the HOMO level of mmtBu-BiFF-02 was −5.46 eV.

Furthermore, GSP of mmtBuBiFF-02 was obtained by the method described in Example 1. The results show that GSP of mmtBuBiFF-02 is 39.5 mV/nm.

Example 3

In this example, light-emitting devices of one embodiment of the present invention described in the above embodiments and comparative light-emitting devices are described. Structural formulae of organic compounds used for the light-emitting devices of one embodiment of the present invention are shown below.

[Chemical Formulae 25]

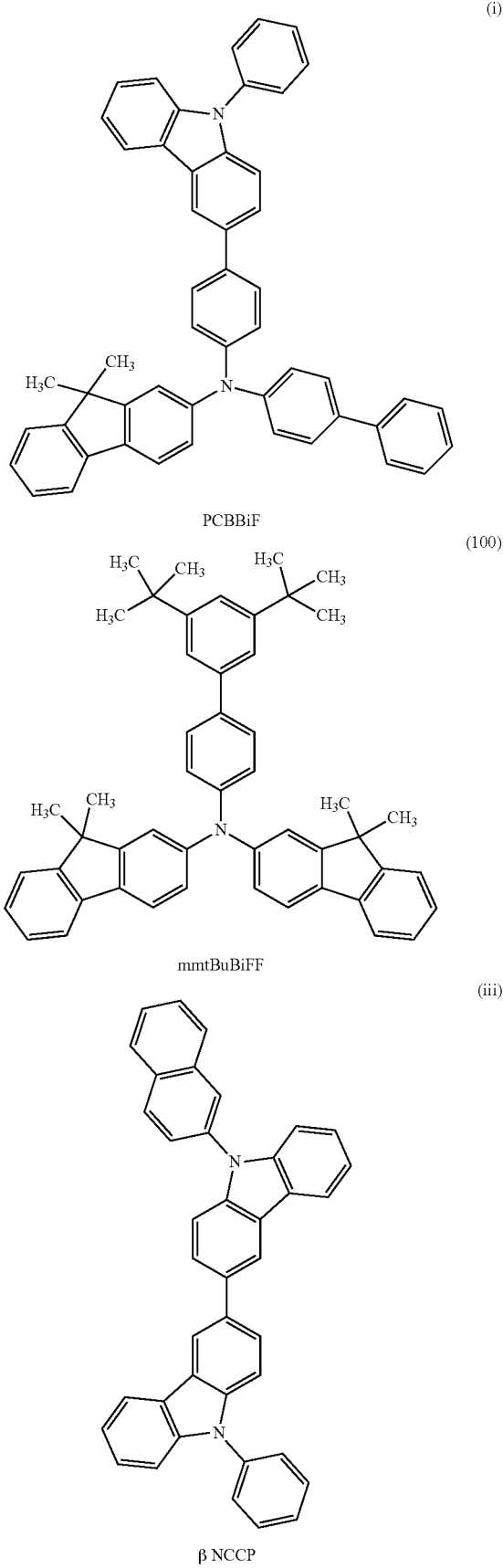

PCBBiF (i)

mmtBuBiFF (100)

β NCCP (iii)

(101)
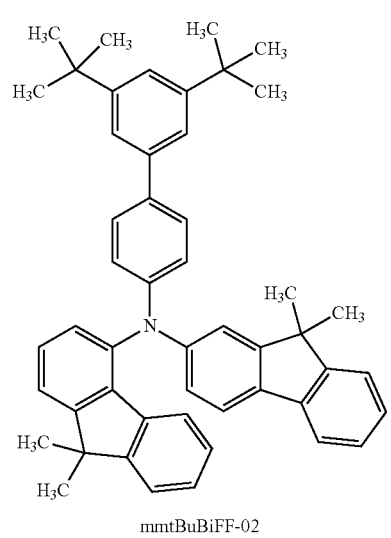
mmtBuBiFF-02
(ii)
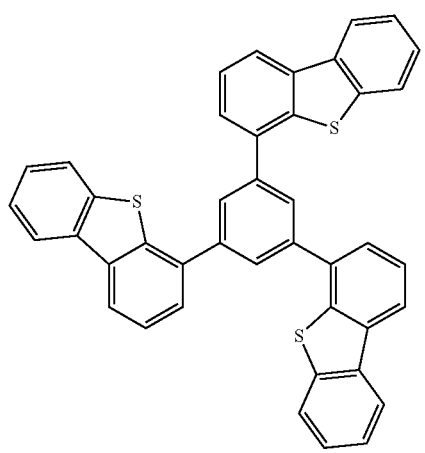
BP-Icz(1I)Tzn
(iv)
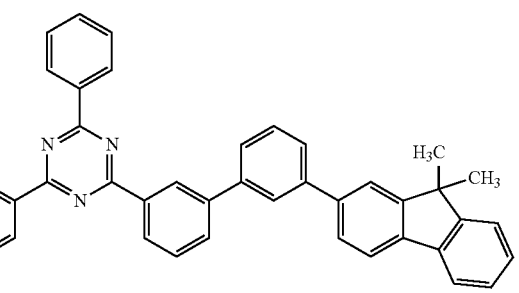
Ir(ppy)₂(mbfpypy-d₃)
(vii)
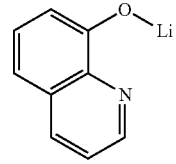
Liq
(viii)
DBT3P-II
(v)
mFBPTzn -continued (vi)

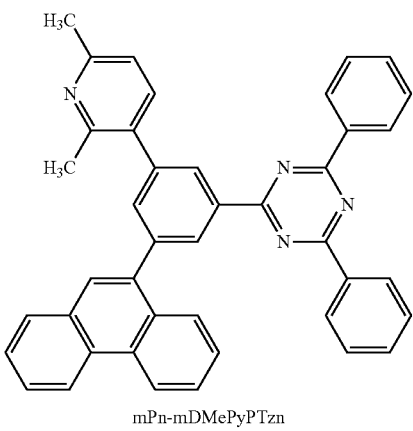

mPn-mDMePyPTzn (Method for Fabricating Light-Emitting Device 1-1)

Figure 24:
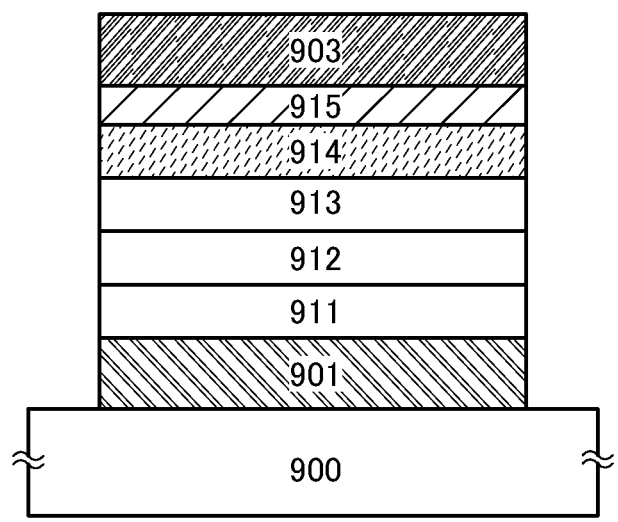
FIG. 24 illustrates a structure of a light-emitting device of an example.

In a light-emitting device 1-1 described in this example, as illustrated in FIG. 24, a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, silver (Ag) was deposited over the glass substrate 900 to a thickness of 100 nm to form a reflective electrode. After that, indium tin oxide containing silicon oxide (ITSO) was deposited by a sputtering method to form the first electrode 901. The thickness of the first electrode 901 was 10 nm and the electrode area was 2 mm×2 mm.

Next, in pretreatment for forming the light-emitting device over the substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was allowed to cool down for approximately 30 minutes.

Then, the substrate provided with the first electrode 901 was fixed to a substrate holder provided in the vacuum evaporation apparatus such that the surface on which the first electrode 901 was formed faced downward. Over the first electrode 901, N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (i) and a fluorine-containing electron acceptor material with a molecular weight of 672 (OCHD-003) were deposited by co-evaporation using resistance heating to a thickness of 10 nm such that the weight ratio of PCBBiF to OCHD-003 was 1:0.04, whereby the hole-injection layer 911 was formed.

Next, over the hole-injection layer 911, PCBBiF was deposited by evaporation to a thickness of 115 nm, and then the fluorine-containing electron acceptor material with a molecular weight of 672 (OCHD-003) was deposited by evaporation to a thickness of 1 nm. Furthermore, N-(3',5'-di-tert-butyl-1,1'-biphenyl-4-yl)-bis(9,9-dimethyl-9H-fluoren)–2,2'-amine (abbreviation: mmtBuBiFF), which is the organic compound of one embodiment of the present invention represented by Structural Formula (100), was deposited by evaporation to a thickness of 40 nm to form the hole-transport layer 912.

Subsequently, 11-(4-[1,1'-biphenyl]-4-yl-6-phenyl-1,3,5-triazin-2-yl)-11,12-dihydro-12-phenyl-indolo[2,3-α]carbazole (abbreviation: BP-Icz(II)Tzn) represented by Structural Formula (ii), 9-(2-naphthyl)-9'-phenyl-9H,9'H-3,3'-bicarbazole (abbreviation: PNCCP) represented by Structural Formula (iii), and [2-$d_3$-methyl-(2-pyridinyl-κN)benzofuro[2,3-b]pyridine-κC]bis[2-(2-pyridinyl-κN)phenyl-κC]iridium (III) (abbreviation: Ir(ppy)$_2$(mbfpypy-$d_3$)) represented by Structural Formula (iv) were deposited by co-evaporation to a thickness of 40 nm such that the weight ratio of BP-Icz(II)Tzn to PNCCP and Ir(ppy)$_2$(mbfpypy-$d_3$) was 0.5:0.5:0.10, whereby the light-emitting layer 913 was formed.

After that, over the light-emitting layer 913, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (v) was deposited by evaporation to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (vi) and 8-quinolinolato-lithium (abbreviation: Liq) represented by Structural Formula (vii) were deposited by co-evaporation to a thickness of 25 nm such that the weight ratio of mPn-mDMePyPTzn to Liq was 0.5:0.5, whereby the electron-transport layer 914 was formed.

After the formation of the electron-transport layer 914, lithium fluoride (LiF) was deposited by evaporation to a thickness of 1 nm to form the electron-injection layer 915. Then, silver (Ag) and magnesium (Mg) were deposited by co-evaporation to a thickness of 15 nm such that the weight ratio of Ag to Mg was 10:1 to form the second electrode 903, whereby the light-emitting device 1-1 of this example was fabricated. The second electrode 903 is a transflective electrode having a function of reflecting light and a function of transmitting light; thus, the light-emitting device of this example is a top-emission device in which light is extracted through the second electrode 903. Over the second electrode 903, 4,4',4"-(benzene-1,3,5-triyl)tri(dibenzothiophene) (abbreviation: DBT3P-II) represented by Structure Formula (viii) was deposited by evaporation to a thickness of 70 nm so that outcoupling efficiency can be improved.

(Method for Fabricating Light-Emitting Device 1-2)

Over the hole-injection layer 911, PCBBiF was deposited by evaporation to a thickness of 110 nm, and then OCHD-003 was deposited by evaporation to a thickness of 1 nm to fabricate a light-emitting device 1-2. The light-emitting device 1-2 was fabricated in the same manner as the light-emitting device 1-1 except that N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02), which is the organic compound of one embodiment of the present invention represented by Structural Formula (101), was deposited by evaporation to a thickness of 40 nm to form the hole-transport layer 912.

Next, methods for fabricating comparative light-emitting devices are described. Structural formulae of organic compounds used for the comparative light-emitting devices are shown below.

[Chemical Formulae 26]

(ix)

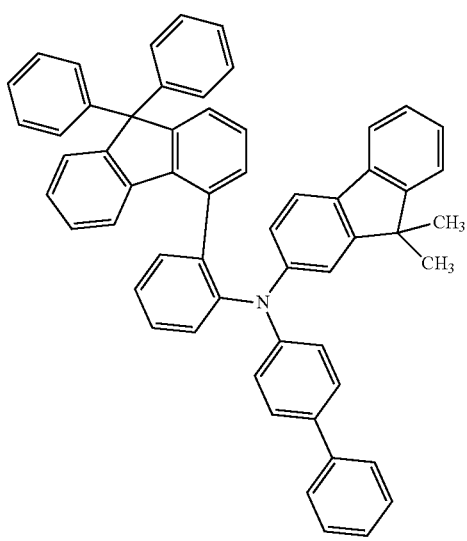

FBiFLPB (x)

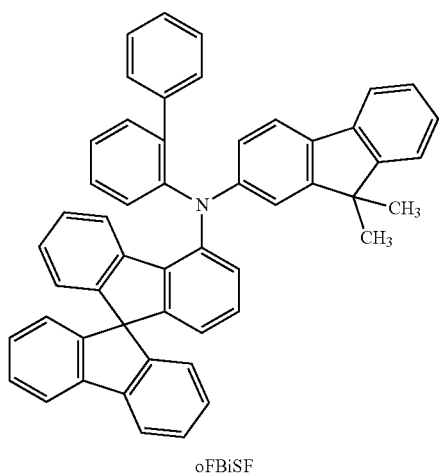

oFBiSF (Method for Fabricating Comparative Light-Emitting Device 1-1)

Over the hole-injection layer 911, PCBBiF was deposited by evaporation to a thickness of 110 nm, and then OCHD-003 was deposited by evaporation to a thickness of 1 nm to fabricate a comparative light-emitting device 1-1. The comparative light-emitting device 1-1 was fabricated in the same manner as the light-emitting device 1-1 except that N-[2-(9,9-diphenyl-9H-fluoren-4-yl)phenyl]-N-(1,1'-biphenyl-4-yl)-9,9-dimethyl-9H-fluoren-2-amine (abbreviation: FBiFLPB) represented by Structural Formula (ix) was deposited by evaporation to a thickness of 40 nm to form the hole-transport layer 912.

(Method for Fabricating Comparative Light-Emitting Device 1-2)

Over the hole-injection layer 911, PCBBiF was deposited by evaporation to a thickness of 110 nm, and then OCHD-003 was deposited by evaporation to a thickness of 1 nm to fabricate a comparative light-emitting device 1-2. The comparative light-emitting device 1-2 was fabricated in the same manner as the light-emitting device 1-1 except that N-(1,1'-biphenyl-2-yl)-N-(9,9-dimethyl-9H-fluoren-2-yl)-9,9'-spirobi[9H-fluoren]-4-amine (abbreviation: oFBiSF) represented by Structural Formula (x) was deposited by evaporation to a thickness of 40 nm to form the hole-transport layer 912.

The structures of the light-emitting devices and the comparative light-emitting devices are listed in the following table.

TABLE 1

| | Thickness | Light-emitting device 1-1 | Light-emitting device 1-2 | Comparative light-emitting device 1-1 | Comparative light-emitting device 1-2 |
|---|---|---|---|---|---|
| Electron-injection layer | 1 nm | LiF | | | |
| Electron-transport layer | 25 nm | mPn-mDMePyPTzn:Liq (0.5:0.5) | | | |
| | 10 nm | mFBPTzn | | | |
| Light-emitting layer | 40 nm | BP-Icz(II)Tzn:βNCCP:Ir(ppy)$_2$(mbfpypy-d$_3$) (0.5:0.5:0.10) | | | |
| | 40 nm | mmtBuBiFF | mmtBuBiFF-02 | FBiFLPB | oFBiSF |
| Hole-transport layer | 1 nm | OCHD-003 | | | |
| | — | PCBBiF (115 nm) | PCBBiF (110 nm) | PCBBiF (110 nm) | PCBBiF (110 nm) |
| Hole-injection layer | 10 nm | PCBBiF:OCHD-003 (1:0.04) | | | |

Figure 25:
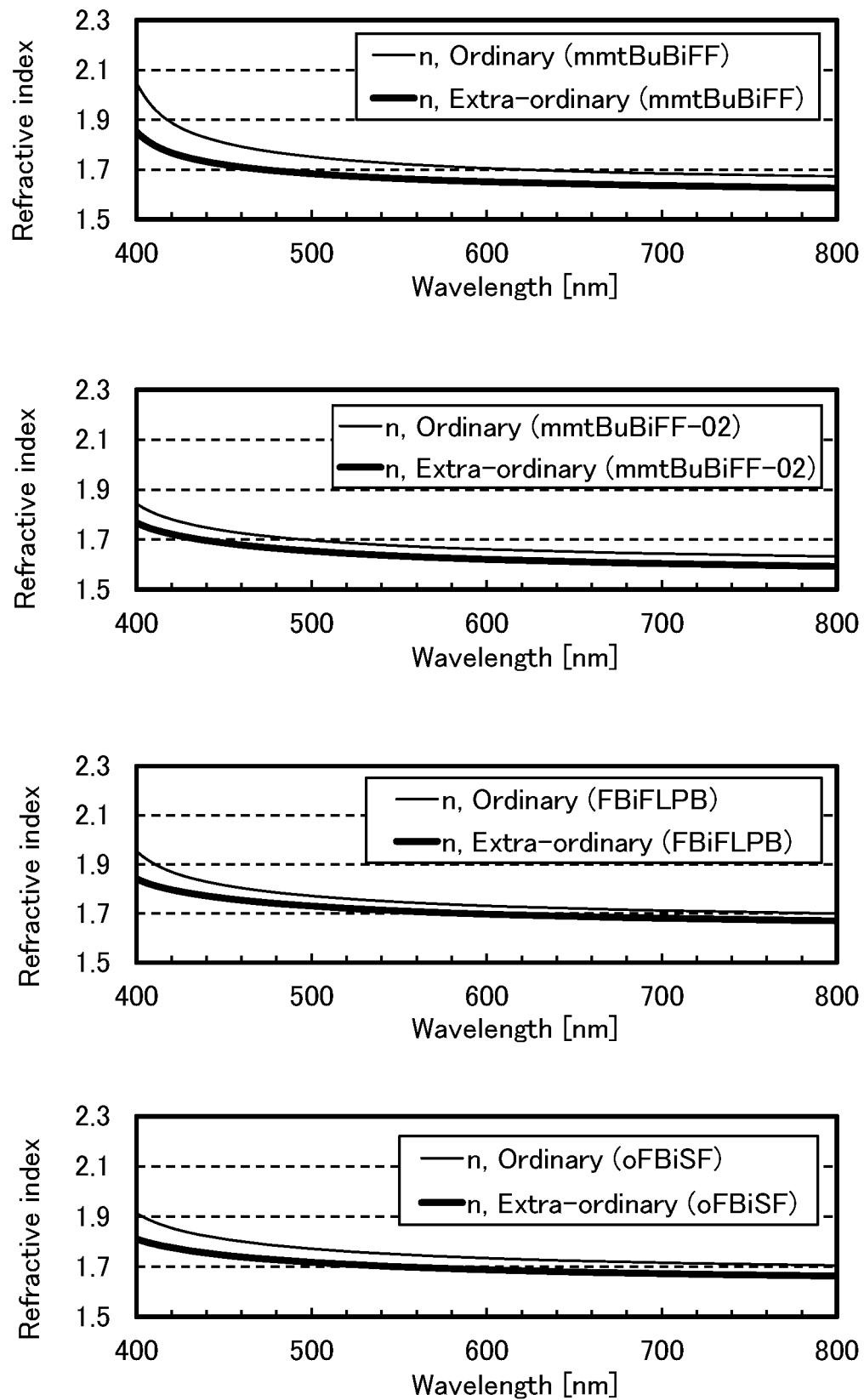
FIG. 25 shows measurement data of refractive indices of mmtBuBiFF, mmtBuBiFF-02, FBiFLPB, and oFBiSF.

FIG. 25 shows the wavelength dependence of the refractive indices of the low refractive index materials used for part of the hole-transport layer and the refractive indices of FBiFLPB and oFBiSF as references, and the following table lists the refractive indices at a wavelength of 520 nm.

TABLE 2

| | Ordinary refractive index (n, Ordinary) at 520 nm |
|---|---|
| mmtBuBiFF | 1.74 |
| mmtBuBiFF-02 | 1.69 |
| FBIFLPB | 1.76 |
| oFBiSF | 1.76 |

The light-emitting devices and the comparative light-emitting devices were sealed using a glass substrate in a glove box containing a nitrogen atmosphere so as not to be exposed to the air (a sealing material was applied to surround the devices and UV treatment and heat treatment at 80° C. for 1 hour were performed at the time of sealing). Then, the initial characteristics of the light-emitting devices were measured.

Figure 26:
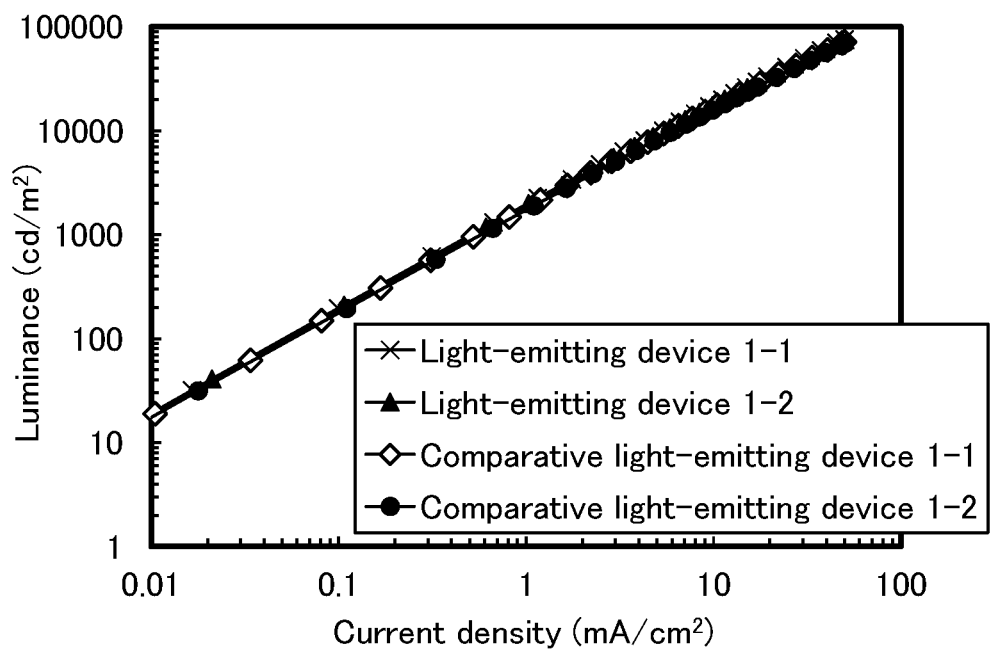
FIG. 26 shows the luminance-current density characteristics of light-emitting devices 1-1 and 1-2 and comparative light-emitting devices 1-1 and 1-2.
Figure 27:
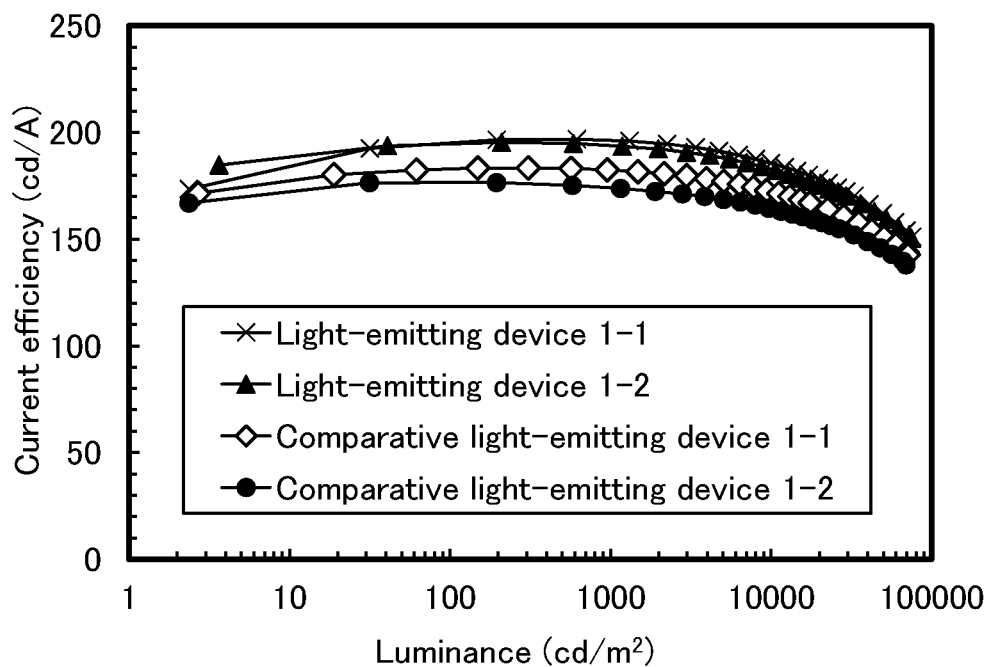
FIG. 27 shows the current efficiency-luminance characteristics of the light-emitting devices 1-1 and 1-2 and the comparative light-emitting devices 1-1 and 1-2.
Figure 28:
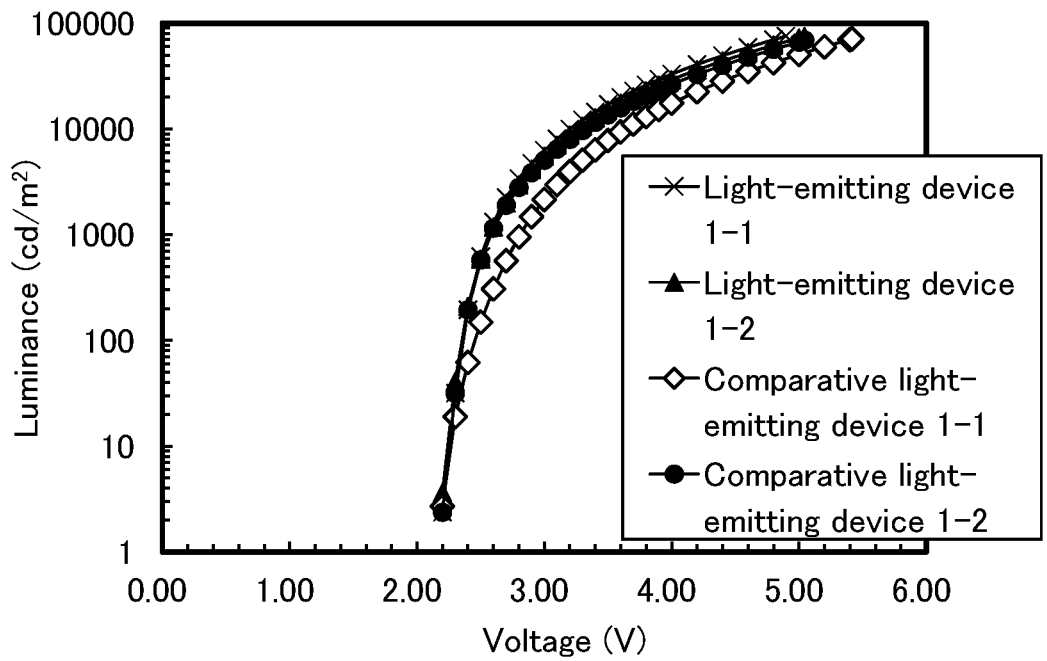
FIG. 28 shows the luminance-voltage characteristics of the light-emitting devices 1-1 and 1-2 and the comparative light-emitting devices 1-1 and 1-2.
Figure 29:
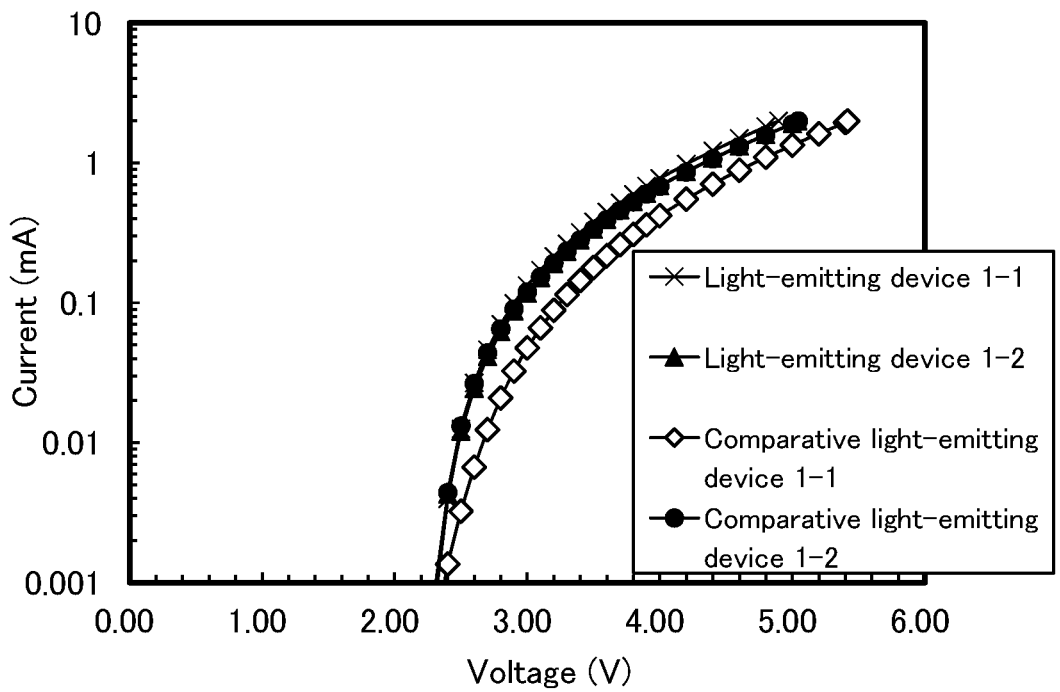
FIG. 29 shows the current-voltage characteristics of the light-emitting devices 1-1 and 1-2 and the comparative light-emitting devices 1-1 and 1-2.
Figure 30:
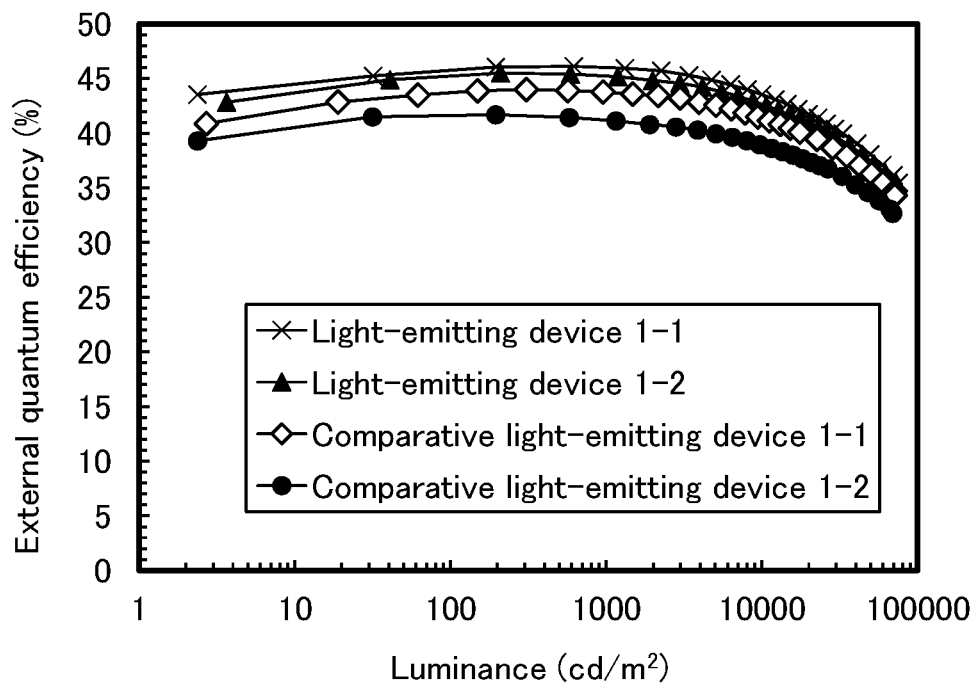
FIG. 30 shows the external quantum efficiency-luminance characteristics of the light-emitting devices 1-1 and 1-2 and the comparative light-emitting devices 1-1 and 1-2.
Figure 31:
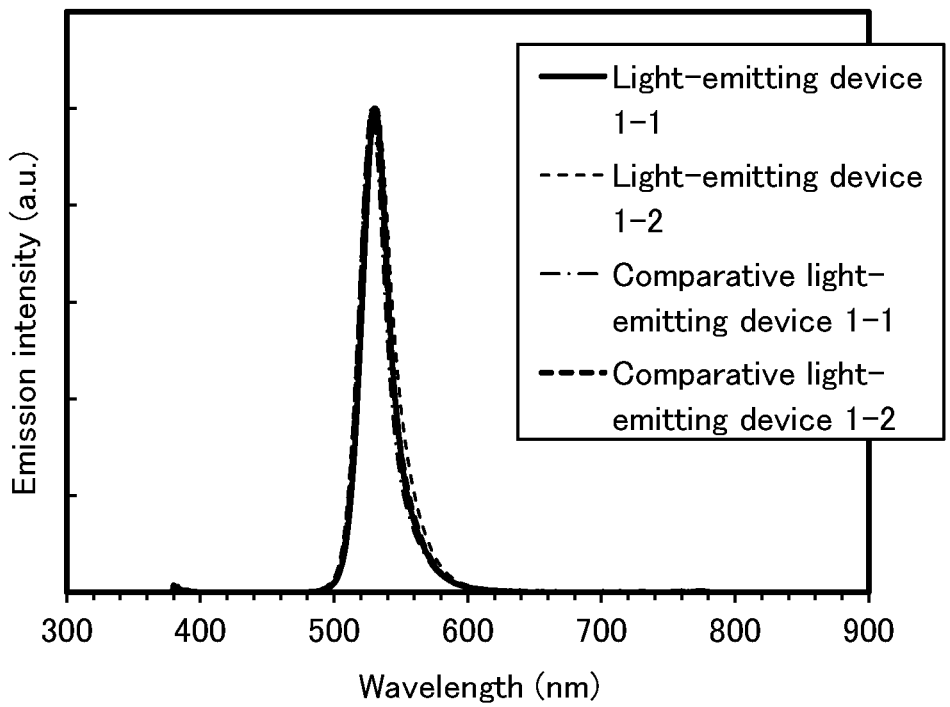
FIG. 31 shows the emission spectra of the light-emitting devices 1-1 and 1-2 and the comparative light-emitting devices 1-1 and 1-2.

FIG. 26 shows the luminance-current density characteristics of the light-emitting devices 1-1 and 1-2 and the comparative light-emitting devices 1-1 and 1-2. FIG. 27 shows the current efficiency-luminance characteristics thereof. FIG. 28 shows the luminance-voltage characteristics thereof. FIG. 29 shows the current-voltage characteristics thereof. FIG. 30 shows the external quantum efficiency-luminance characteristics thereof. FIG. 31 shows the emission spectra thereof. Table 3 shows the main characteristics of the light-emitting devices at a luminance of about 1000 cd/m². Luminance, CIE chromaticity, and emission spectra were measured with a spectroradiometer (SR-UL1R, produced by TOPCON TECHNOHOUSE CORPORATION). The external quantum efficiency was calculated from the luminance and the emission spectra measured with the spectroradiometer, on the assumption that the light-emitting devices had Lambertian light-distribution characteristics.

FIG. 26, FIG. 27, FIG. 28, FIG. 29, FIG. 30, and FIG. 31 reveal that the light-emitting devices 1-1 and 1-2 of one embodiment of the present invention have higher emission efficiency than the comparative light-emitting devices 1-1 and 1-2.

Figure 32:
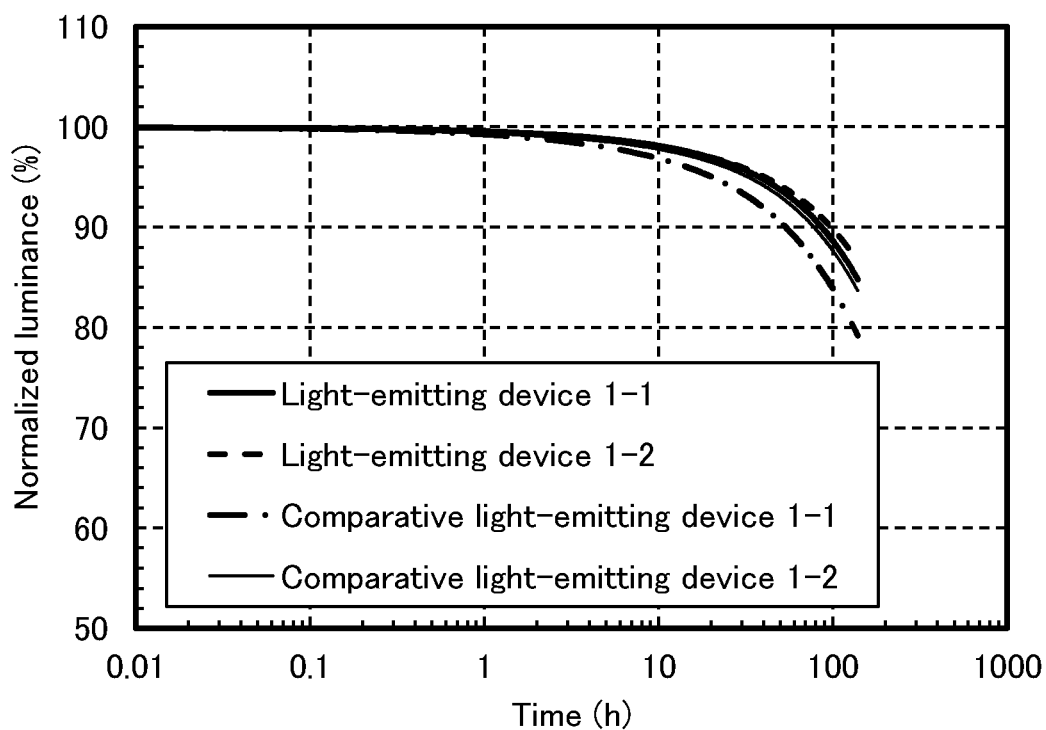
FIG. 32 shows a change in luminance over driving time of the light-emitting devices 1-1 and 1-2 and the comparative light-emitting devices 1-1 and 1-2.

FIG. 32 shows luminance changes over driving time when the light-emitting devices 1-1 and 1-2 and the comparative light-emitting devices 1-1 and 1-2 are driven at a constant current of 2 mA (50 mA/cm²). FIG. 32 shows no big difference in luminance change among the EL devices, which reveals that the light-emitting devices of one embodiment of the present invention have high emission efficiency while keeping a long lifetime.

Example 4

In this example, light-emitting devices of one embodiment of the present invention described in the above embodiments and comparative light-emitting devices are described. Structural formulae of organic compounds used for the light-emitting devices of one embodiment of the present invention are shown below.

[Chemical Formulae 27]

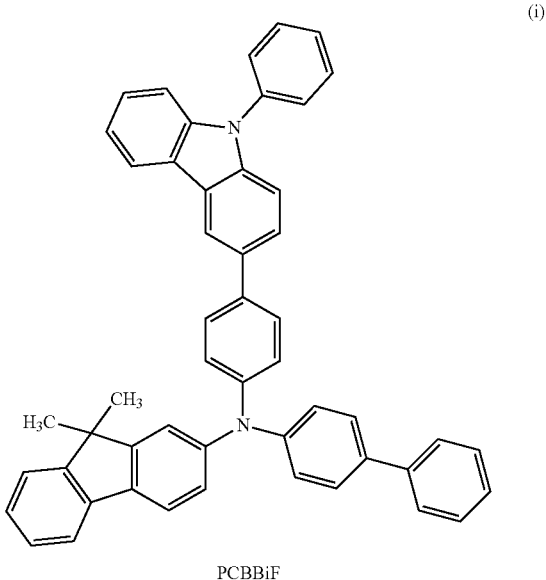

PCBBiF

TABLE 3

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 1-1 | 2.6 | 0.027 | 0.67 | 0.22 | 0.74 | 196 | 45.9 |
| Light-emitting device 1-2 | 2.6 | 0.024 | 0.61 | 0.23 | 0.73 | 194 | 45.2 |
| Comparative light-emitting device 1-1 | 2.8 | 0.021 | 0.52 | 0.21 | 0.75 | 182 | 43.8 |
| Comparative light-emitting device 1-2 | 2.6 | 0.027 | 0.66 | 0.22 | 0.74 | 174 | 41.1 |

(100)
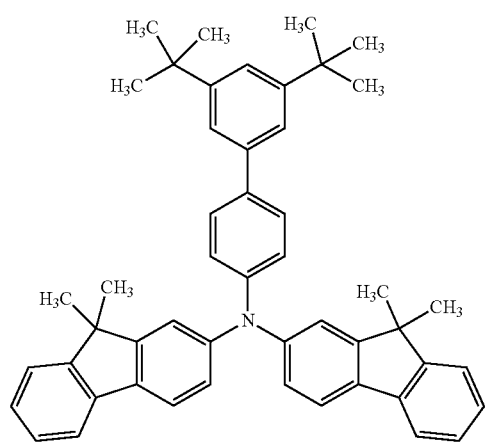
mmtBuBiFF
(iii)
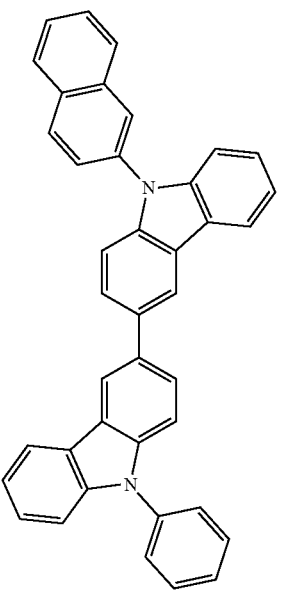
β NCCP
(101)
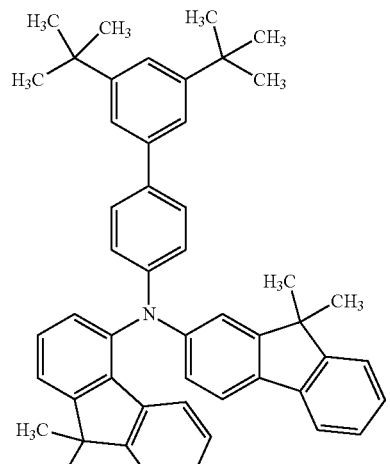
mmtBuBiFF-02
(ii)
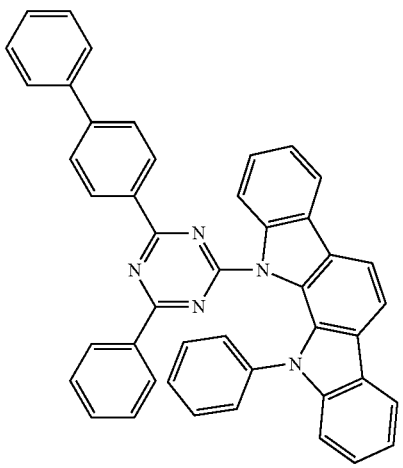
BP-Icz(1I)Tzn
(iv)
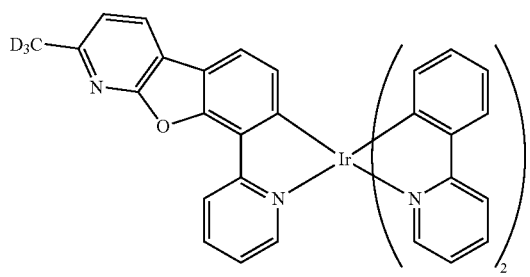
Ir(ppy)$_2$(mbfpypy-d$_3$)
(vii)
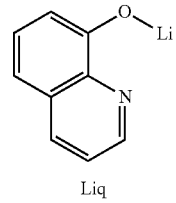
Liq
(viii)
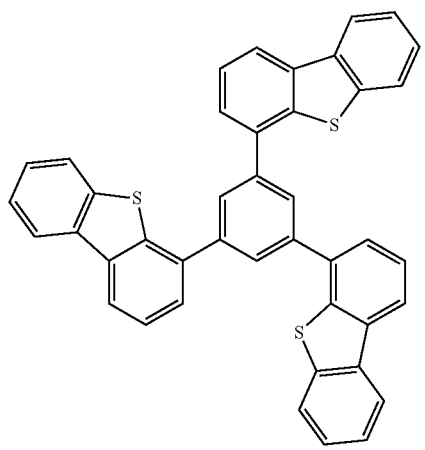
DBT3P-II

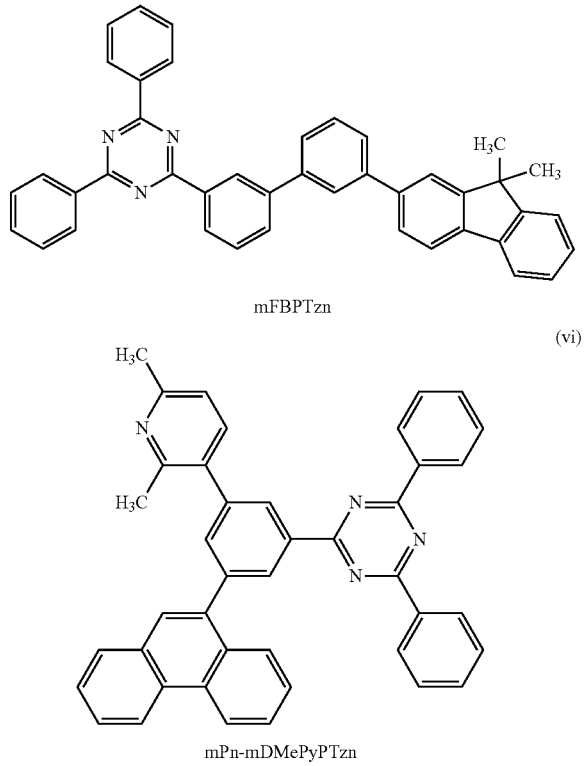

mFBPTzn mPn-mDMePyPTzn (Method for Fabricating Light-Emitting Device 2-1)

In a light-emitting device 2-1 described in this example, as illustrated in FIG. 24, the hole-injection layer 911, the hole-transport layer 912, the light-emitting layer 913, the electron-transport layer 914, and the electron-injection layer 915 are stacked in this order over the first electrode 901 formed over the substrate 900, and the second electrode 903 is stacked over the electron-injection layer 915.

First, silver (Ag) was deposited over the glass substrate 900 to a thickness of 100 nm to form a reflective electrode. After that, indium tin oxide containing silicon oxide (ITSO) was deposited by a sputtering method to form the first electrode 901. The thickness of the first electrode 901 was 10 nm and the electrode area was 2 mm×2 mm.

Next, in pretreatment for forming the light-emitting device over the substrate, a surface of the substrate was washed with water and baked at 200° C. for 1 hour, and then UV ozone treatment was performed for 370 seconds.

After that, the substrate was transferred into a vacuum evaporation apparatus where the pressure was reduced to approximately $10^{-4}$ Pa, vacuum baking was performed at 170° C. for 30 minutes in a heating chamber of the vacuum evaporation apparatus, and then the substrate was allowed to cool down for approximately 30 minutes.

Then, the substrate provided with the first electrode 901 was fixed to a substrate holder provided in the vacuum evaporation apparatus such that the surface on which the first electrode 901 was formed faced downward. Over the first electrode 901, N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (i) and a fluorine-containing electron acceptor material with a molecular weight of 672 (OCHD-003) were deposited by co-evaporation using resistance heating to a thickness of 10 nm such that the weight ratio of PCBBiF to OCHD-003 was 1:0.04, whereby the hole-injection layer 911 was formed.

Next, over the hole-injection layer 911, PCBBiF was deposited by evaporation to a thickness of 115 nm, and then N-(3',5'-di-tert-butyl-1,1'-biphenyl-4-yl)-bis(9,9-dimethyl-9H-fluoren)–2,2'-amine (abbreviation: mmtBuBiFF), which is the organic compound of one embodiment of the present invention represented by Structural Formula (100), was deposited by evaporation to a thickness of 40 nm, whereby the hole-transport layer 912 was formed.

Subsequently, 11-(4-[1,1'-biphenyl]-4-yl-6-phenyl-1,3,5-triazin-2-yl)-11,12-dihydro-12-phenyl-indolo[2,3-α]carbazole (abbreviation: BP-Icz(II)Tzn) represented by Structural Formula (ii), 9-(2-naphthyl)-9'-phenyl-9H,9'H-3,3'-bicarbazole (abbreviation: PNCCP) represented by Structural Formula (iii), and [2-d$_3$-methyl-(2-pyridinyl-κN)benzofuro[2,3-b]pyridine-κC]bis[2-(2-pyridinyl-κN)phenyl-κC]iridium (III) (abbreviation: Ir(ppy)$_2$(mbfpypy-d$_3$)) represented by Structural Formula (iv) were deposited by co-evaporation to a thickness of 40 nm such that the weight ratio of BP-Icz(II)Tzn to PNCCP and Ir(ppy)$_2$(mbfpypy-d$_3$) was 0.5:0.5:0.10, whereby the light-emitting layer 913 was formed.

After that, over the light-emitting layer 913, 2-[3'-(9,9-dimethyl-9H-fluoren-2-yl)-1,1'-biphenyl-3-yl]-4,6-diphenyl-1,3,5-triazine (abbreviation: mFBPTzn) represented by Structural Formula (v) was deposited by evaporation to a thickness of 10 nm, and then 2-[3-(2,6-dimethyl-3-pyridinyl)-5-(9-phenanthrenyl)phenyl]-4,6-diphenyl-1,3,5-triazine (abbreviation: mPn-mDMePyPTzn) represented by Structural Formula (vi) and 8-quinolinolato-lithium (abbreviation: Liq) represented by Structural Formula (vii) were deposited by co-evaporation to a thickness of 25 nm such that the weight ratio of mPn-mDMePyPTzn to Liq was 0.5:0.5, whereby the electron-transport layer 914 was formed.

After the formation of the electron-transport layer 914, lithium fluoride (LiF) was deposited by evaporation to a thickness of 1 nm to form the electron-injection layer 915. Then, silver (Ag) and magnesium (Mg) were deposited by co-evaporation to a thickness of 15 nm such that the weight ratio of Ag to Mg was 10:1 to form the second electrode 903, whereby the light-emitting device 2-1 of this example was fabricated. The second electrode 903 is a transflective electrode having a function of reflecting light and a function of transmitting light; thus, the light-emitting device of this example is a top-emission device in which light is extracted through the second electrode 903. Over the second electrode 903, 4,4',4"-(benzene-1,3,5-triyl)tri(dibenzothiophene) (abbreviation: DBT3P-II) represented by Structure Formula (viii) was deposited by evaporation to a thickness of 70 nm so that outcoupling efficiency can be improved.

Note that the light-emitting device 2-1 is different from the light-emitting device 1-1 in that the fluorine-containing electron acceptor material with a molecular weight of 672 (OCHD-003) is not used for the hole-transport layer 912.

(Method for Fabricating Light-Emitting Device 2-2)

A light-emitting device 2-2 was fabricated in the same manner as the light-emitting device 2-1 except that, over the hole-injection layer 911, PCBBiF was deposited by evaporation to a thickness of 110 nm, and then N-(3',5'-di-tert-butyl-1,1'-biphenyl-4-yl)-N-(9,9-dimethyl-9H-fluoren-4-yl)-9,9-dimethyl-9H-fluoren-2-amine (abbreviation: mmtBuBiFF-02), which is the organic compound of one embodiment of the present invention represented by Structural Formula (101), was deposited by evaporation to a thickness of 40 nm to form the hole-transport layer 912.

Note that the light-emitting device 2-2 is different from the light-emitting device 1-2 in that OCHD-003 is not used for the hole-transport layer 912.

Next, methods for fabricating comparative light-emitting devices are described. Structural formulae of organic compounds used for the comparative light-emitting devices are shown below.

[Chemical Formulae 28]

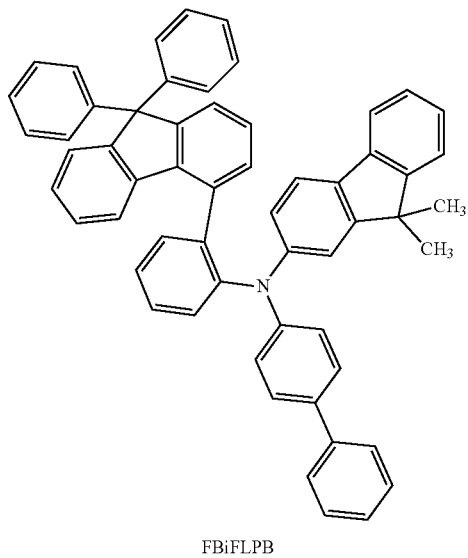

FBiFLPB (ix)

oFBiSF (x)

(Method for Fabricating Comparative Light-Emitting Device 2-1)

A comparative light-emitting device 2-1 was fabricated in the same manner as the light-emitting device 2-1 except that, over the hole-injection layer 911, PCBBiF was deposited by evaporation to a thickness of 115 nm, and then N-[2-(9,9-diphenyl-9H-fluoren-4-yl)phenyl]-N-(1,1'-biphenyl-4-yl)-9,9-dimethyl-9H-fluoren-2-amine (abbreviation: FBiFLPB) represented by Structural Formula (ix) was deposited by evaporation to a thickness of 40 nm to form the hole-transport layer 912.

Note that the comparative light-emitting device 2-1 is different from the comparative light-emitting device 1-1 in that the thickness of PCBBiF is 115 nm and OCHD-003 is not used for the hole-transport layer 912.

(Method for Fabricating Comparative Light-Emitting Device 2-2)

A comparative light-emitting device 2-2 was fabricated in the same manner as the light-emitting device 2-1 except that, over the hole-injection layer 911, PCBBiF was deposited by evaporation to a thickness of 110 nm, and then N-(1,1'-biphenyl-2-yl)-N-(9,9-dimethyl-9H-fluoren-2-yl)-9,9'-spirobi[9H-fluoren]-4-amine (abbreviation: oFBiSF) represented by Structural Formula (x) was deposited by evaporation to a thickness of 40 nm to form the hole-transport layer 912.

Note that the comparative light-emitting device 2-2 is different from the comparative light-emitting device 1-2 in that OCHD-003 is not used for the hole-transport layer 912.

The structures of the light-emitting devices and the comparative light-emitting devices are listed in the following table.

TABLE 4

|  | Thickness | Light-emitting device 2-1 | Light-emitting device 2-2 | Comparative light-emitting device 2-1 | Comparative light-emitting device 2-2 |
|---|---|---|---|---|---|
| Electron-injection layer | 1 nm | LiF | | | |
| Electron-transport layer | 25 nm | mPn-mDMePyPTzn:Liq (0.5:0.5) | | | |
| | 10 nm | mFBPTzn | | | |
| Light-emitting layer | 40 nm | BP-Icz(II)Tzn:βNCCP:Ir(ppy)$_2$(mbfpypy-d$_3$) (0.5:0.5:0.10) | | | |
| Hole-transport layer | 40 nm | mmtBuBiFF | mmtBuBiFF-02 | FBiFLPB | oFBiSF |
| | — | PCBBiF (115 nm) | PCBBiF (110 nm) | PCBBiF (115 nm) | PCBBiF (110 nm) |
| Hole-injection layer | 10 nm | PCBBiF:OCHD-003 (1:0.04) | | | |

The following table lists GSP of the materials used for the hole-transport layer.

TABLE 5

Figure 35:
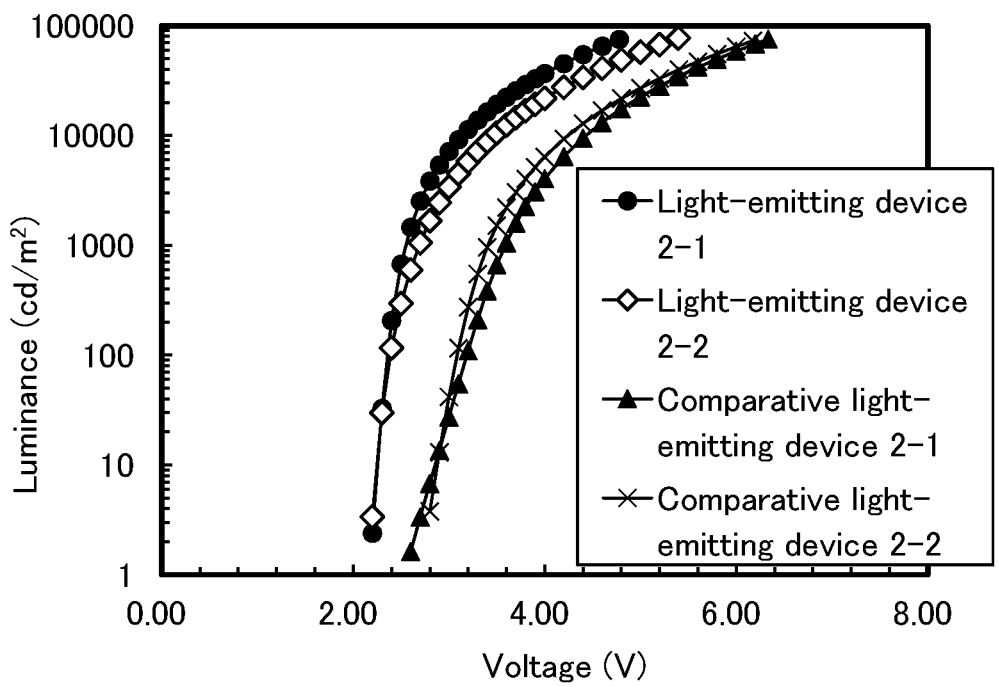
FIG. 35 shows the luminance-voltage characteristics of the light-emitting devices 2-1 and 2-2 and the comparative light-emitting devices 2-1 and 2-2.
Figure 36:
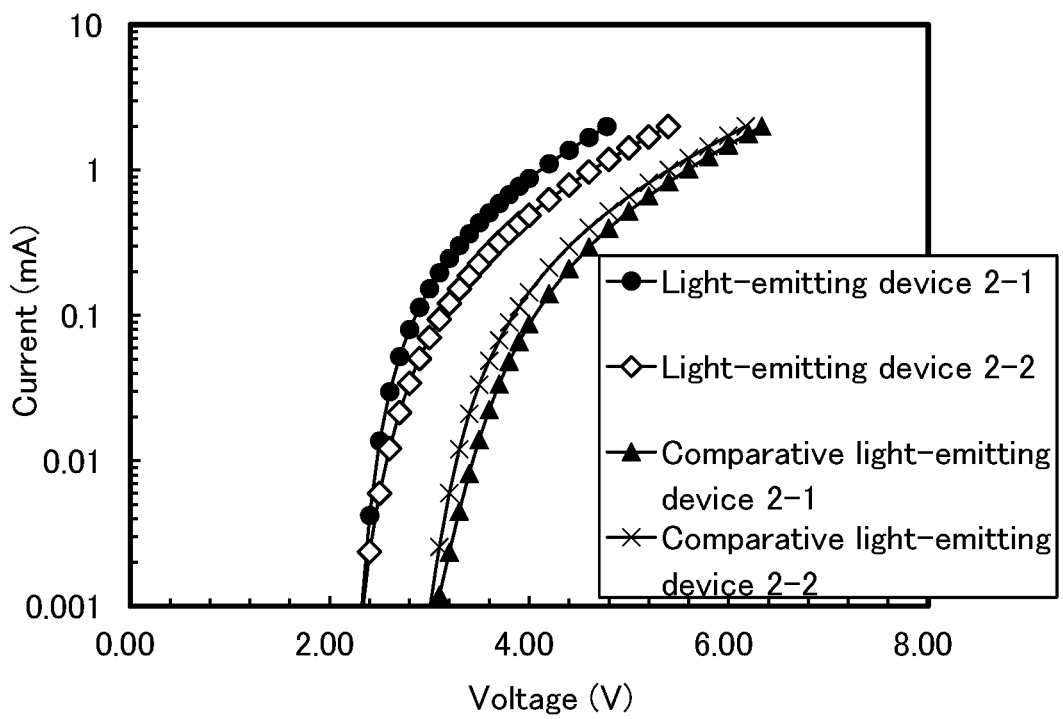
FIG. 36 shows the current-voltage characteristics of the light-emitting devices 2-1 and 2-2 and the comparative light-emitting devices 2-1 and 2-2.
Figure 37:
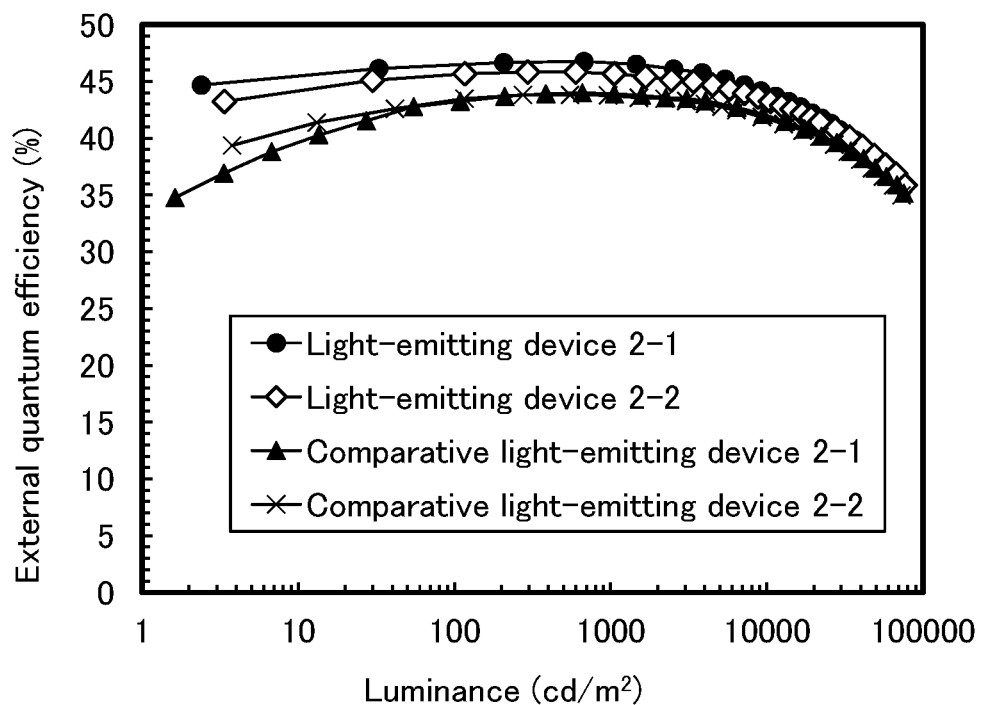
FIG. 37 shows the external quantum efficiency-luminance characteristics of the light-emitting devices 2-1 and 2-2 and the comparative light-emitting devices 2-1 and 2-2.
Figure 38:
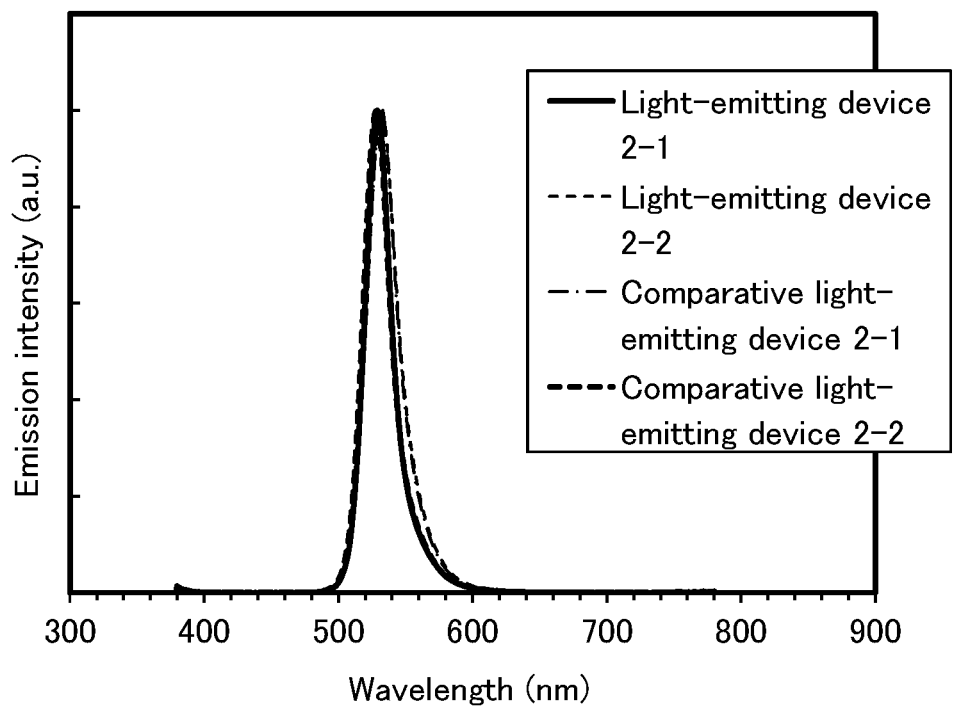
FIG. 38 shows the emission spectra of the light-emitting devices 2-1 and 2-2 and the comparative light-emitting devices 2-1 and 2-2.

| | GSP (mV/nm) |
|---|---|
| mmtBuBiFF | 39.5 |
| mmtBuBiFF-02 | 27.2 |
| FBiFLPB | 18.6 |
| oFBiSF | 11.3 |
| PCBBiF | 17.3 | thereof. FIG. 35 shows the luminance-voltage characteristics thereof. FIG. 36 shows the current-voltage characteristics thereof. FIG. 37 shows the external quantum efficiency-luminance characteristics thereof. FIG. 38 shows the emission spectra thereof. Table 6 shows the main characteristics of the light-emitting devices at a luminance of about 1000 cd/m$^2$. Luminance, CIE chromaticity, and emission spectra were measured with a spectroradiometer (SR-UL1R, produced by TOPCON TECHNOHOUSE CORPORATION). The external quantum efficiency was calculated from the luminance and the emission spectra measured with the spectroradiometer, on the assumption that the light-emitting devices had Lambertian light-distribution characteristics.

TABLE 6

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 2-1 | 2.5 | 0.014 | 0.34 | 0.21 | 0.75 | 197 | 46.8 |
| Light-emitting device 2-2 | 2.7 | 0.021 | 0.54 | 0.24 | 0.73 | 196 | 45.7 |
| Comparative light-emitting device 2-1 | 3.6 | 0.022 | 0.56 | 0.23 | 0.73 | 188 | 43.9 |
| Comparative light-emitting device 2-2 | 3.4 | 0.021 | 0.53 | 0.21 | 0.75 | 182 | 43.8 |

The organic compounds of one embodiment of the present invention used for the hole-transport layers 912 of the light-emitting devices 2-1 and 2-2 each have high GSP exceeding 20 mV/nm. In the hole-transport layer 912 having the stacked-layer structure, GSP is compared between the material used for the layer in contact with the light-emitting layer 913 and the material used for the layer in contact with the hole-injection layer 911. As a result, a difference in GSP between the material used for the layer in contact with the hole-injection layer 911 and the material used for the layer in contact with the light-emitting layer 913 is as small as 1.3 mV/nm in the comparative light-emitting device 2-1. In addition, GSP of the material used for the layer in contact with the light-emitting layer 913 is lower than that of the material used for the layer in contact with the hole-injection layer 911 in the comparative light-emitting device 2-2. By contrast, in each of the light-emitting devices 2-1 and 2-2, GSP of the material used for the layer in contact with the light-emitting layer 913 is higher than that of the material used for the layer in contact with the hole-injection layer 911 by approximately 10 mV/nm or more.

The light-emitting devices and the comparative light-emitting devices were sealed using a glass substrate in a glove box containing a nitrogen atmosphere so as not to be exposed to the air (a sealing material was applied to surround the devices and UV treatment and heat treatment at 80° C. for 1 hour were performed at the time of sealing). Then, the initial characteristics of the light-emitting devices were measured.

Figure 33:
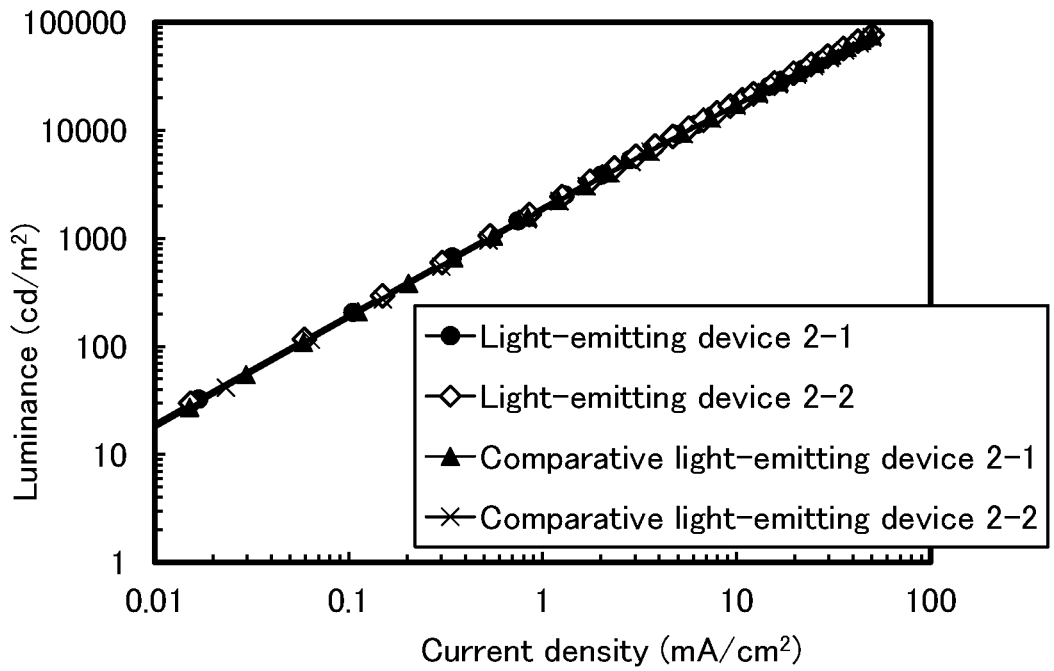
FIG. 33 shows the luminance-current density characteristics of light-emitting devices 2-1 and 2-2 and comparative light-emitting devices 2-1 and 2-2.
Figure 34:
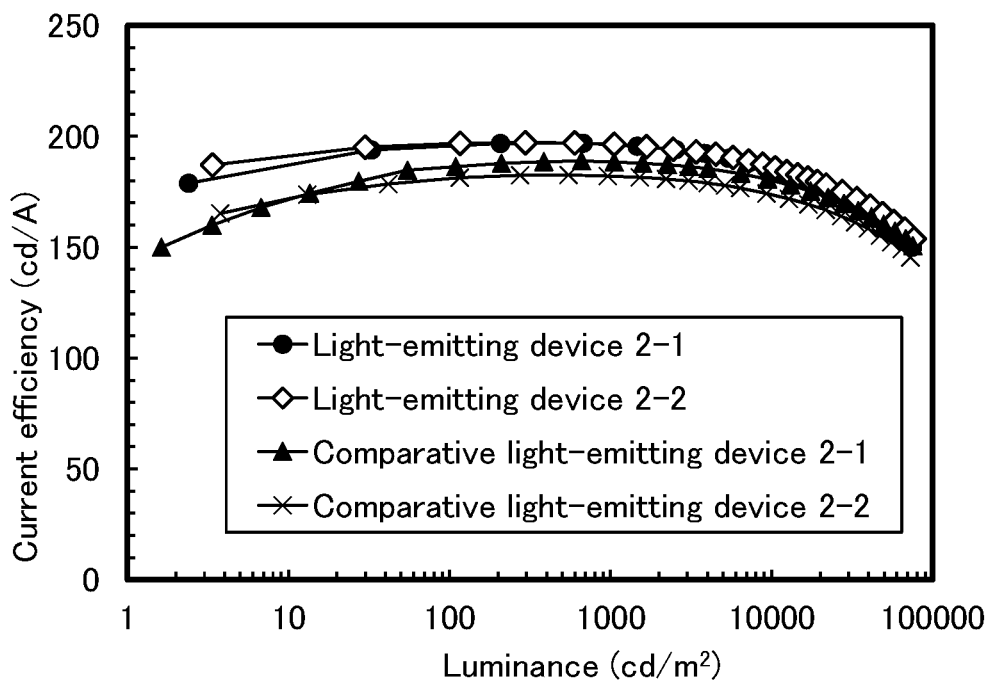
FIG. 34 shows the current efficiency-luminance characteristics of the light-emitting devices 2-1 and 2-2 and the comparative light-emitting devices 2-1 and 2-2.

FIG. 33 shows the luminance-current density characteristics of the light-emitting devices 2-1 and 2-2 and the comparative light-emitting devices 2-1 and 2-2. FIG. 34 shows the current efficiency-luminance characteristics FIG. 33, FIG. 34, FIG. 35, FIG. 36, FIG. 37, and FIG. 38 reveal that the light-emitting devices 2-1 and 2-2 of one embodiment of the present invention have significantly higher emission efficiency than the comparative light-emitting devices 2-1 and 2-2.

The comparison of the device characteristics between the comparative light-emitting devices 2-1 and 2-2 and the comparative light-emitting devices 1-1 and 1-2 described in Example 3 reveals that the luminance-voltage characteristics and current-voltage characteristics of the comparative light-emitting devices 2-1 and 2-2 are lower than those of the comparative light-emitting devices 1-1 and 1-2. This demonstrates that the power consumption of the comparative light-emitting devices increases when OCHD-003 is not used for the hole-transport layer 912.

Meanwhile, the comparison of the characteristics between the light-emitting devices of one embodiment of the present invention reveals that the characteristics of the light-emitting devices 2-1 and 2-2 do not decrease from those of the light-emitting devices 1-1 and 1-2. This demonstrates that the light-emitting devices of one embodiment of the present invention can keep excellent characteristics even without the use of OCHD-003 for the hole-transport layer 912. This is due to high GSP of the organic compounds of one embodiment of the present invention. That is, the use of any of the organic compounds of one embodiment of the present invention with high GSP for the layer, which is in contact with the light-emitting layer 913, in the hole-transport layer 912 having the stacked-layer structure facilitates hole injection at the interface between the stacked layers in the hole-transport layer 912. This allows the light-emitting devices of one embodiment of the present invention to keep excellent characteristics without the use of OCHD-003 for the hole-transport layer 912.

Accordingly, the use of the organic compounds of one embodiment of the present invention can eliminate one layer of the layers in the hole-transport layer 912; thus, a highly productive device can be fabricated.

Figure 39:
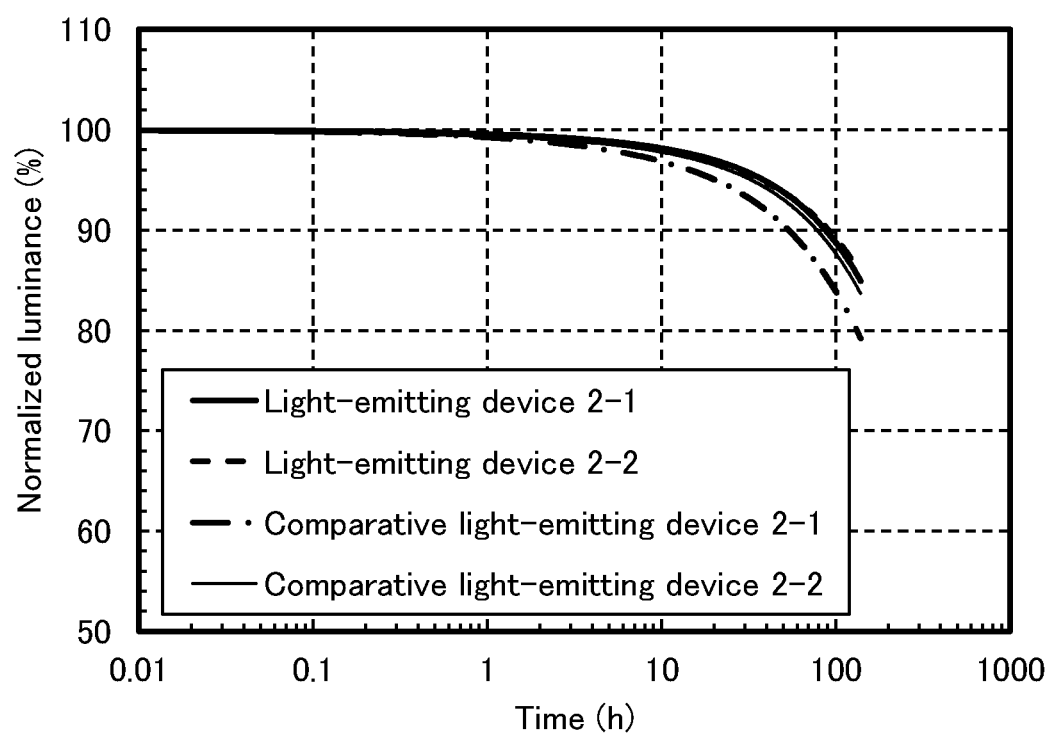
FIG. 39 shows a change in luminance over driving time of the light-emitting devices 2-1 and 2-2 and the comparative light-emitting devices 2-1 and 2-2.

FIG. 39 shows luminance changes over driving time when the light-emitting devices 2-1 and 2-2 and the comparative light-emitting devices 2-1 and 2-2 are driven at a constant current of 2 mA (50 mA/cm$^2$). FIG. 39 shows no big difference in luminance change among the EL devices, which reveals that the light-emitting devices of one embodiment of the present invention have high emission efficiency while keeping a long lifetime.

This application is based on Japanese Patent Application Serial No. 2021-060448 filed with Japan Patent Office on Mar. 31, 2021, the entire contents of which are hereby incorporated by reference.

What is claimed is:

1. An organic compound represented by General Formula (G1):

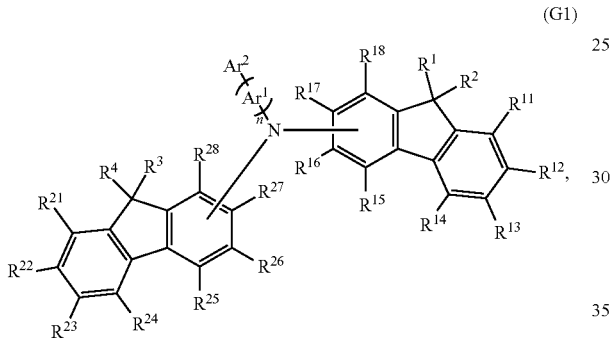

(G1)

wherein Ar$^1$ represents a substituted or unsubstituted arylene group having 6 to 13 carbon atoms in a ring, wherein n represents 1, wherein Ar$^2$ represents an aryl group having 6 to 10 carbon atoms in the ring and substituted with two or more substituents, each of the substituents comprising at least one branched-chain or cyclic alkyl group having 3 to 12 carbon atoms, wherein the total number of carbon atoms of the substituents in Ar$^2$ is more than or equal to 6, wherein R$^1$ to R$^4$ each independently represent an alkyl group having 1 to 6 carbon atoms, wherein R$^{11}$ to R$^{14}$ each independently represent a hydrogen atom or an alkyl group having 1 to 4 carbon atoms, wherein any one of R$^{15}$ to R$^{18}$ represents a bond directly bonded to the nitrogen atom, and the others each independently represent a hydrogen atom or an alkyl group having 1 to 4 carbon atoms, wherein R$^{21}$ to R$^{24}$ each independently represent a hydrogen atom or an alkyl group having 1 to 4 carbon atoms, and wherein any one of R$^{25}$ to R$^{28}$ represents a bond directly bonded to the nitrogen atom, and the others each independently represent a hydrogen atom or an alkyl group having 1 to 4 carbon atoms.

2. An organic compound represented by General Formula (G2):

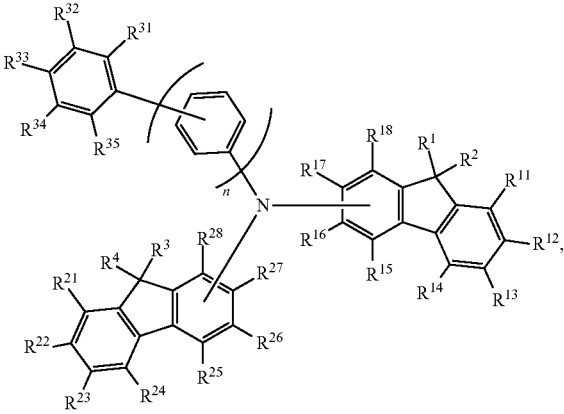

(G2)

wherein R$^1$ to R$^4$ each independently represent an alkyl group having 1 to 6 carbon atoms, wherein R$^{11}$ to R$^{14}$ each independently represent a hydrogen atom or an alkyl group having 1 to 4 carbon atoms, wherein any one of R$^{15}$ to R$^{18}$ represents a bond directly bonded to the nitrogen atom, and the others each independently represent a hydrogen atom or an alkyl group having 1 to 4 carbon atoms, wherein R$^{21}$ to R$^{24}$ each independently represent a hydrogen atom or an alkyl group having 1 to 4 carbon atoms, wherein any one of R$^{25}$ to R$^{28}$ represents a bond directly bonded to the nitrogen atom, and the others each independently represent a hydrogen atom or an alkyl group having 1 to 4 carbon atoms, wherein R$^{31}$ to R$^{35}$ each independently represent a hydrogen atom, a branched-chain alkyl group having 3 to 12 carbon atoms, or a cyclic alkyl group having 3 to 12 carbon atoms, and at least two of R$^{31}$ to R$^{35}$ each independently represent the branched-chain alkyl group having 3 to 12 carbon atoms or the cyclic alkyl group having 3 to 12 carbon atoms, wherein the total number of carbon atoms in R$^{31}$ to R$^{35}$ is more than or equal to 6, and wherein n represents an integer of 0 or 1.

3. An organic compound represented by General Formula (G3):

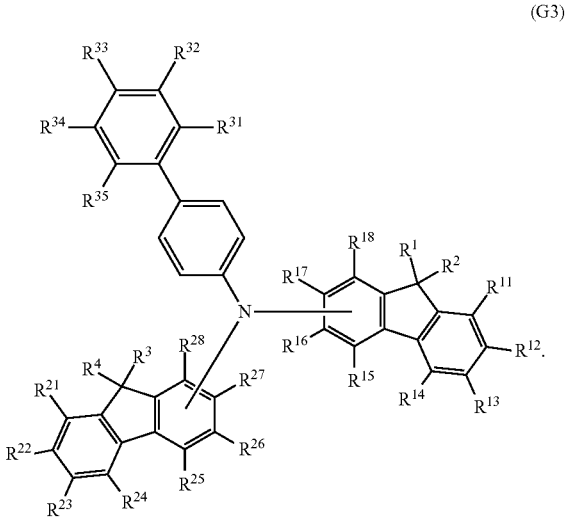

(G3)

wherein $R^1$ to $R^4$ each independently represent an alkyl group having 1 to 6 carbon atoms,
wherein $R^{11}$ to $R^{14}$ each independently represent a hydrogen atom or an alkyl group having 1 to 4 carbon atoms,
wherein any one of $R^{15}$ to $R^{18}$ represents a bond directly bonded to the nitrogen atom, and the others each independently represent a hydrogen atom or an alkyl group having 1 to 4 carbon atoms,
wherein $R^{21}$ to $R^{24}$ each independently represent a hydrogen atom or an alkyl group having 1 to 4 carbon atoms,
wherein any one of $R^{25}$ to $R^{28}$ represents a bond directly bonded to the nitrogen atom, and the others each independently represent a hydrogen atom or an alkyl group having 1 to 4 carbon atoms,
wherein $R^{31}$, $R^{32}$, $R^{34}$, and $R^{35}$ each represent a hydrogen atom, and
wherein $R^{33}$ represents a cyclic alkyl group having 3 to 12 carbon atoms and substituted with a branched-chain alkyl group having 3 to 12 carbon atoms.

4. The organic compound according to claim 1,
wherein $R^{11}$ to $R^{14}$ and $R^{21}$ to $R^{24}$ each represent a hydrogen atom,
wherein any one of $R^{15}$ to $R^{18}$ represents a bond directly bonded to the nitrogen atom, and the others each represent a hydrogen atom, and
wherein any one of $R^{25}$ to $R^{28}$ represents a bond directly bonded to the nitrogen atom, and the others each represent a hydrogen atom.

5. The organic compound according to claim 2,
wherein $R^{11}$ to $R^{14}$ and $R^{21}$ to $R^{24}$ each represent a hydrogen atom,
wherein any one of $R^{15}$ to $R^{18}$ represents a bond directly bonded to the nitrogen atom, and the others each represent a hydrogen atom, and
wherein any one of $R^{25}$ to $R^{28}$ represents a bond directly bonded to the nitrogen atom, and the others each represent a hydrogen atom.

6. The organic compound according to claim 2, wherein the General Formula (G2) is represented by General Formula (G4):

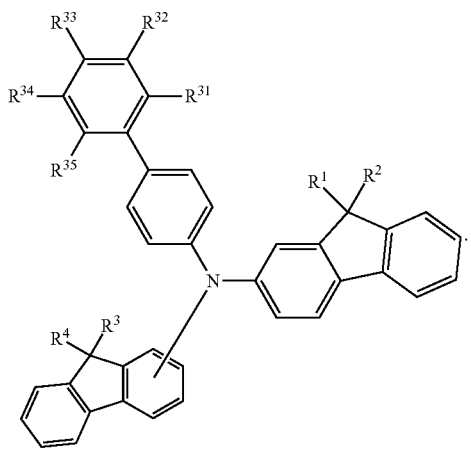

(G4)

7. The organic compound according to claim 2,
wherein at least two of $R^{31}$ to $R^{35}$ each represent a tert-butyl group or a cyclohexyl group.

8. The organic compound according to claim 2,
wherein $R^{31}$, $R^{33}$, and $R^{35}$ each represent a hydrogen atom, and wherein $R^{32}$ and $R^{34}$ each represent a tert-butyl group or a cyclohexyl group.

9. The organic compound according to claim 2, wherein the General Formula (G2) is represented by Structural Formula (100) or (101):

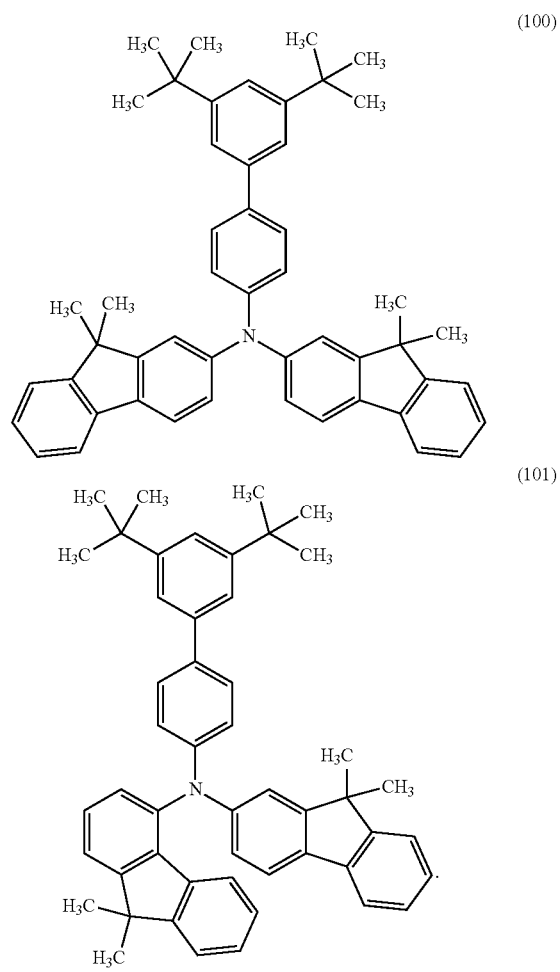

10. A light-emitting device comprising the organic compound according to claim 1.

11. An electronic device comprising:
the light-emitting device according to claim 10; and
at least one of a sensor unit, an input unit, and a communication unit.

12. A light-emitting apparatus comprising:
the light-emitting device according to claim 10; and
at least one of a transistor and a substrate.

13. A lighting device comprising:
the light-emitting device according to claim 10; and
a housing.

14. The organic compound according to claim 3,
wherein $R^{11}$ to $R^{14}$ and $R^{21}$ to $R^{24}$ each represent a hydrogen atom,
wherein any one of $R^{15}$ to $R^{18}$ represents a bond directly bonded to the nitrogen atom, and the others each represent a hydrogen atom, and
wherein any one of $R^{25}$ to $R^{28}$ represents a bond directly bonded to the nitrogen atom, and the others each represent a hydrogen atom.

15. The organic compound according to claim 3, wherein the General Formula (G3) is represented by General Formula (G4):
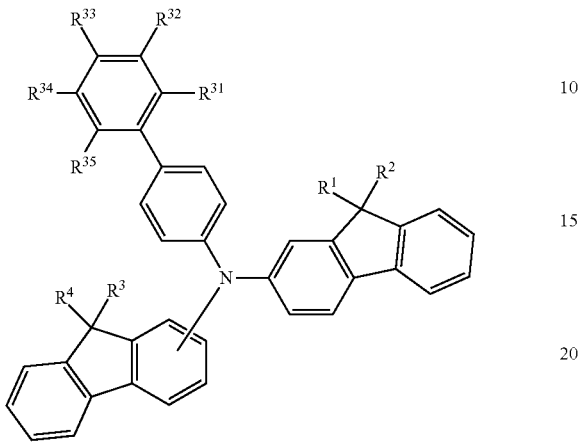
(G4)
16. A light-emitting device comprising the organic compound according to claim 2.
17. A light-emitting device comprising the organic compound according to claim 3.
* * * * *